US012023459B2

(12) United States Patent
Erbey, II et al.

(10) Patent No.: US 12,023,459 B2
(45) Date of Patent: *Jul. 2, 2024

(54) NEGATIVE PRESSURE THERAPY SYSTEM

(71) Applicant: Roivios Limited, Nassau (BS)

(72) Inventors: John R. Erbey, II, Milton, GA (US); Jacob L. Upperco, Atlanta, GA (US); Michael Alan Fisher, Lawrenceville, GA (US); Patrick William Strane, Atlanta, GA (US); Lance Michael Black, Pearland, TX (US)

(73) Assignee: Roivios Limited, Nassau (BS)

( * ) Notice: Subject to any disclaimer, the term of this patent is extended or adjusted under 35 U.S.C. 154(b) by 305 days.

This patent is subject to a terminal disclaimer.

(21) Appl. No.: 17/392,165

(22) Filed: Aug. 2, 2021

(65) Prior Publication Data

US 2021/0361908 A1 Nov. 25, 2021

Related U.S. Application Data

(63) Continuation of application No. 16/036,971, filed on Jul. 17, 2018, now Pat. No. 11,077,284, which is a
(Continued)

(51) Int. Cl.
*A61M 27/00* (2006.01)
*A61F 13/15* (2006.01)
(Continued)

(52) U.S. Cl.
CPC .......... *A61M 27/008* (2013.01); *A61M 1/70* (2021.05); *A61M 1/73* (2021.05); *A61M 1/743* (2021.05);
(Continued)

(58) Field of Classification Search
CPC .. A61M 27/008; A61M 1/73; A61M 25/0017; A61M 25/04; A61M 25/10;
(Continued)

(56) References Cited

U.S. PATENT DOCUMENTS 1,870,942 A    8/1932  Beatty
2,285,980 A    6/1942  Jeckel
(Continued)

FOREIGN PATENT DOCUMENTS

AU    2013332448 A1    4/2015
CA       1243581 A    10/1988
(Continued)

OTHER PUBLICATIONS

Johnson et al., "Clinical Practice Guidelines for Chronic Kidney Disease in Adults: Part I. Definition, Disease Stages, Evaluation, Treatment, and Risk Factors", American Family Physician, Sep. 1, 2004, p. 869-876, vol. 70 Issue 5.
(Continued)

*Primary Examiner* — Adam Marcetich
(74) *Attorney, Agent, or Firm* — The Webb Law Firm

(57) ABSTRACT

Negative pressure therapy systems are provided for increasing urine production, the negative pressure therapy system including: (a) a pump assembly, the pump assembly including: (i) a pump configured to provide negative pressure to a kidney, and (ii) a controller configured to regulate the negative pressure provided by the pump within a pressure range that facilitates increased urine production from the kidney.

21 Claims, 29 Drawing Sheets

Related U.S. Application Data continuation of application No. 15/214,955, filed on Jul. 20, 2016, now Pat. No. 10,307,564.

(60) Provisional application No. 62/300,025, filed on Feb. 25, 2016, provisional application No. 62/278,721, filed on Jan. 14, 2016, provisional application No. 62/260,966, filed on Nov. 30, 2015, provisional application No. 62/194,585, filed on Jul. 20, 2015.

(51) Int. Cl.
| | |
|---|---|
| *A61F 13/20* | (2006.01) |
| *A61M 1/00* | (2006.01) |
| *A61M 25/00* | (2006.01) |
| *A61M 25/02* | (2006.01) |
| *A61M 25/04* | (2006.01) |
| *A61M 25/10* | (2013.01) |
| *A61M 39/12* | (2006.01) |

(52) U.S. Cl.
CPC ............... *A61M 1/80* (2021.05); *A61M 1/84* (2021.05); *A61M 25/0017* (2013.01); *A61M 25/0023* (2013.01); *A61M 25/0026* (2013.01); *A61M 25/04* (2013.01); *A61M 25/10* (2013.01); *A61M 25/1025* (2013.01); *A61M 39/12* (2013.01); *A61F 2013/15146* (2013.01); *A61F 13/2002* (2013.01); *A61M 25/0068* (2013.01); *A61M 25/0074* (2013.01); *A61M 2025/0213* (2013.01); *A61M 2202/0496* (2013.01); *A61M 2205/0266* (2013.01); *A61M 2205/3303* (2013.01); *A61M 2205/3368* (2013.01); *A61M 2205/50* (2013.01); *A61M 2205/52* (2013.01); *A61M 2205/75* (2013.01); *A61M 2210/1085* (2013.01); *A61M 2210/1092* (2013.01); *A61M 2210/1096* (2013.01); *A61M 2230/20* (2013.01); *A61M 2230/50* (2013.01); *A61M 2230/65* (2013.01)

(58) Field of Classification Search
CPC .......... A61M 25/0068; A61M 25/0074; A61M 2202/0496; A61M 2210/1085; A61M 2210/1092; A61M 2210/1096; A61M 2230/20; A61M 2230/50; A61M 2230/65; A61F 2013/15146
See application file for complete search history.

(56) References Cited

U.S. PATENT DOCUMENTS

| | | |
|---|---|---|
| 2,649,092 A | 8/1953 | Wallace |
| 3,108,595 A | 10/1963 | Overment |
| 3,397,699 A | 8/1968 | Kohl |
| 3,561,431 A | 2/1971 | Pannier, Jr. |
| 3,707,967 A | 1/1973 | Kitrilakis |
| 3,875,941 A | 4/1975 | Adair |
| 3,938,529 A | 2/1976 | Gibbons |
| 3,938,530 A | 2/1976 | Santomieri |
| 3,943,929 A | 3/1976 | Patel |
| 4,265,243 A | 5/1981 | Taylor |
| 4,306,557 A | 12/1981 | North |
| 4,324,663 A | 4/1982 | Hirel et al. |
| 4,349,029 A | 9/1982 | Mott |
| 4,425,124 A | 1/1984 | Womack |
| 4,437,856 A | 3/1984 | Valli |
| 4,531,933 A | 7/1985 | Norton et al. |
| 4,568,338 A | 2/1986 | Todd |
| 4,571,241 A | 2/1986 | Christopher |
| 4,575,371 A | 3/1986 | Nordqvist et al. |
| 4,629,015 A | 12/1986 | Fried et al. |
| 4,681,564 A | 7/1987 | Landreneau |
| 4,710,169 A | 12/1987 | Christopher |
| 4,738,667 A | 4/1988 | Galloway |
| 4,813,935 A | 3/1989 | Haber et al. |
| 4,834,724 A | 5/1989 | Geiss et al. |
| 4,932,938 A | 6/1990 | Goldberg et al. |
| 4,935,004 A | 6/1990 | Cruz |
| 4,945,895 A | 8/1990 | Takai et al. |
| 4,950,228 A | 8/1990 | Knapp, Jr. et al. |
| 4,957,479 A | 9/1990 | Roemer |
| 5,009,639 A | 4/1991 | Keymling |
| 5,011,488 A | 4/1991 | Ginsburg |
| 5,041,093 A | 8/1991 | Chu |
| 5,044,902 A | 9/1991 | Malbec |
| 5,059,169 A | 10/1991 | Zilber |
| 5,078,684 A | 1/1992 | Yasuda |
| 5,098,440 A | 3/1992 | Hillstead |
| 5,116,309 A | 5/1992 | Coll |
| 5,141,502 A | 8/1992 | Macaluso, Jr. |
| 5,193,533 A | 3/1993 | Body et al. |
| 5,256,146 A | 10/1993 | Ensminger et al. |
| 5,370,690 A | 12/1994 | Barrett |
| 5,401,257 A | 3/1995 | Chevalier, Jr. et al. |
| 5,451,215 A | 9/1995 | Wolter |
| 5,451,218 A | 9/1995 | Moore |
| 5,505,717 A | 4/1996 | Moore |
| 5,514,112 A | 5/1996 | Chu et al. |
| 5,523,092 A | 6/1996 | Hanson et al. |
| 5,536,274 A | 7/1996 | Neuss |
| 5,540,701 A | 7/1996 | Sharkey et al. |
| 5,554,144 A | 9/1996 | Wallace et al. |
| 5,562,622 A | 10/1996 | Tihon |
| 5,599,291 A | 2/1997 | Balbierz et al. |
| 5,647,843 A | 7/1997 | Mesrobian et al. |
| 5,662,713 A | 9/1997 | Andersen et al. |
| 5,709,874 A | 1/1998 | Hanson et al. |
| 5,727,555 A | 3/1998 | Chait |
| 5,769,821 A | 6/1998 | Abrahamson et al. |
| 5,785,641 A | 7/1998 | Davis |
| 5,795,319 A | 8/1998 | Ali |
| 5,865,764 A | 2/1999 | Moorhead |
| 5,873,865 A | 2/1999 | Horzewski et al. |
| 5,895,398 A | 4/1999 | Wensel et al. |
| 5,902,336 A | 5/1999 | Mishkin |
| 5,915,386 A | 6/1999 | Lloyd et al. |
| 5,957,867 A | 9/1999 | Lloyd et al. |
| 5,972,019 A | 10/1999 | Engelson et al. |
| 5,989,207 A | 11/1999 | Hughes |
| 6,066,113 A | 5/2000 | Overtoom |
| 6,090,069 A | 7/2000 | Walker |
| 6,111,520 A | 8/2000 | Allen et al. |
| 6,200,485 B1 | 3/2001 | Kitaevich et al. |
| 6,214,037 B1 | 4/2001 | Mitchell et al. |
| 6,283,940 B1 | 9/2001 | Mulholland |
| 6,332,892 B1 | 12/2001 | Desmond, III et al. |
| 6,364,868 B1 | 4/2002 | Ikeguchi |
| 6,402,736 B1 | 6/2002 | Brown et al. |
| 6,442,415 B1 | 8/2002 | Bis et al. |
| 6,461,346 B1 | 10/2002 | Buelna |
| 6,478,778 B1 | 11/2002 | Jacobsen et al. |
| 6,482,222 B1 | 11/2002 | Bruckheimer et al. |
| 6,500,158 B1 | 12/2002 | Ikeguchi |
| 6,558,350 B1 | 5/2003 | Hart et al. |
| 6,569,150 B2 | 5/2003 | Teague et al. |
| 6,620,202 B2 | 9/2003 | Bottcher et al. |
| 6,648,863 B2 | 11/2003 | Reever |
| 6,676,623 B2 | 1/2004 | Whitmore, III |
| 6,685,744 B2 | 2/2004 | Gellman et al. |
| 6,699,216 B2 | 3/2004 | Ikeguchi |
| 6,702,834 B1 | 3/2004 | Boylan et al. |
| 6,764,519 B2 | 7/2004 | Whitmore, III |
| 6,780,322 B1 | 8/2004 | Bissler et al. |
| 6,837,868 B1 | 1/2005 | Fajnsztajn |
| 7,025,753 B2 | 4/2006 | Reever |
| 7,037,345 B2 | 5/2006 | Bottcher et al. |
| 7,044,981 B2 | 5/2006 | Liu et al. |
| 7,316,663 B2 | 1/2008 | Whitmore, III |
| 7,329,226 B1 | 2/2008 | Ni et al. |
| 7,396,366 B2 | 7/2008 | Ward |
| 7,507,218 B2 | 3/2009 | Aliski et al. |
| 7,550,978 B2 | 6/2009 | Joy et al. |

(56) References Cited

U.S. PATENT DOCUMENTS

| | | |
|---|---|---|
| 7,603,170 B2 | 10/2009 | Hatlestad et al. |
| 7,682,401 B2 | 3/2010 | Deal |
| 7,722,677 B2 | 5/2010 | Ward |
| 7,727,222 B2 | 6/2010 | Da Silva et al. |
| 7,736,354 B2 | 6/2010 | Gelfand et al. |
| 7,758,562 B2 | 7/2010 | Gelfand et al. |
| 7,758,563 B2 | 7/2010 | Gelfand et al. |
| 7,766,961 B2 | 8/2010 | Patel et al. |
| 7,837,667 B2 | 11/2010 | Gelfand et al. |
| 7,850,704 B2 | 12/2010 | Burnett et al. |
| 7,857,803 B1 | 12/2010 | Salinas et al. |
| 7,879,020 B1 | 2/2011 | Salinas et al. |
| 7,938,817 B2 | 5/2011 | Gelfand et al. |
| 7,972,292 B2 | 7/2011 | Behl et al. |
| 8,007,460 B2 | 8/2011 | Gelfand et al. |
| 8,021,307 B2 | 9/2011 | White et al. |
| 8,075,513 B2 | 12/2011 | Rudko et al. |
| 8,088,170 B2 | 1/2012 | Whitmore, III |
| 8,105,317 B2 | 1/2012 | Reever et al. |
| 8,152,786 B2 | 4/2012 | Shapland et al. |
| 8,157,785 B2 | 4/2012 | Salinas et al. |
| 8,177,741 B2 | 5/2012 | Hammack et al. |
| 8,252,065 B2 | 8/2012 | Ward |
| 8,328,877 B2 | 12/2012 | Gellman |
| 8,444,623 B2 | 5/2013 | Gelfand et al. |
| 8,486,010 B2 | 7/2013 | Nomura |
| 8,512,795 B2 | 8/2013 | Dias et al. |
| 8,568,387 B2 | 10/2013 | Paz |
| 8,585,675 B2 | 11/2013 | Salinas et al. |
| 8,597,260 B2 | 12/2013 | Tucker |
| 8,597,273 B2 | 12/2013 | Salinas et al. |
| 8,747,388 B2 | 6/2014 | Pandey et al. |
| 8,795,305 B2 | 8/2014 | Martin et al. |
| 8,827,924 B2 | 9/2014 | Paz et al. |
| 8,852,289 B2 | 10/2014 | Whitmore, III |
| 8,865,063 B2 | 10/2014 | Burnett |
| 9,014,815 B2 | 4/2015 | Yang et al. |
| 9,060,888 B2 | 6/2015 | Gellman |
| 9,308,348 B2 | 4/2016 | Mulvihill et al. |
| 9,339,636 B1 | 5/2016 | Khan et al. |
| 9,682,220 B2 | 6/2017 | Schertiger et al. |
| 9,744,331 B2 | 8/2017 | Erbey, II et al. |
| 9,750,634 B2 | 9/2017 | Bar-Am |
| 9,788,928 B2 | 10/2017 | Forsell |
| 9,849,224 B2 | 12/2017 | Angwin et al. |
| 9,980,663 B2 | 5/2018 | Wabel et al. |
| 10,182,747 B2 | 1/2019 | Charlez et al. |
| 10,226,606 B2 | 3/2019 | Wan et al. |
| 10,307,566 B2 | 6/2019 | Bishawi |
| 10,307,654 B2 | 6/2019 | Erbey, II et al. |
| 10,449,329 B2 | 10/2019 | Foley et al. |
| 11,040,180 B2 | 6/2021 | Erbey, II et al. |
| 2001/0053936 A1 | 12/2001 | Whitmore, III |
| 2001/0056273 A1 | 12/2001 | Ewers |
| 2002/0052576 A1 | 5/2002 | Massengale |
| 2002/0062148 A1 | 5/2002 | Hart |
| 2002/0068093 A1 | 6/2002 | Trogolo et al. |
| 2002/0082547 A1 | 6/2002 | Deniega et al. |
| 2002/0085951 A1 | 7/2002 | Gelfand et al. |
| 2002/0143292 A1 | 10/2002 | Flinchbaugh |
| 2002/0143389 A1 | 10/2002 | St. Pierre |
| 2002/0177902 A1 | 11/2002 | Rioux et al. |
| 2002/0183852 A1 | 12/2002 | McWeeney |
| 2002/0183853 A1 | 12/2002 | Mitchell et al. |
| 2002/0188246 A1 | 12/2002 | Hayner et al. |
| 2002/0193667 A1 | 12/2002 | McNair |
| 2003/0009132 A1 | 1/2003 | Schwartz et al. |
| 2003/0018291 A1 | 1/2003 | Hill et al. |
| 2003/0060806 A1 | 3/2003 | Ikeguchi |
| 2003/0069534 A1 | 4/2003 | Work et al. |
| 2003/0074082 A1 | 4/2003 | Bottcher et al. |
| 2003/0109930 A1 | 6/2003 | Bluni et al. |
| 2003/0120261 A1 | 6/2003 | Gellman |
| 2003/0135147 A1 | 7/2003 | Rosenberg et al. |
| 2003/0135195 A1 | 7/2003 | Jimenez et al. |
| 2003/0144623 A1 | 7/2003 | Heath et al. |
| 2003/0153970 A1 | 8/2003 | Rao et al. |
| 2003/0171708 A1 | 9/2003 | Segura et al. |
| 2003/0176831 A1 | 9/2003 | Gellman et al. |
| 2003/0181842 A1 | 9/2003 | Gellman |
| 2003/0181887 A1 | 9/2003 | Castillo Deniega et al. |
| 2003/0191452 A1 | 10/2003 | Meglin et al. |
| 2003/0195456 A1 | 10/2003 | Robertson |
| 2003/0195537 A1 | 10/2003 | Dubrul et al. |
| 2003/0199805 A1 | 10/2003 | McWeeney |
| 2003/0216710 A1 | 11/2003 | Hurt |
| 2003/0224033 A1 | 12/2003 | Li et al. |
| 2004/0019358 A1 | 1/2004 | Kear |
| 2004/0054315 A1 | 3/2004 | Levin et al. |
| 2004/0054351 A1 | 3/2004 | Deniega et al. |
| 2004/0057037 A1 | 3/2004 | Ohishi et al. |
| 2004/0073194 A1 | 4/2004 | Olsen et al. |
| 2004/0097891 A1 | 5/2004 | Bolmsjo |
| 2004/0129616 A1 | 7/2004 | Mori et al. |
| 2004/0143209 A1 | 7/2004 | Liu et al. |
| 2004/0147871 A1 | 7/2004 | Burnett |
| 2004/0167415 A1 | 8/2004 | Gelfand et al. |
| 2004/0167634 A1 | 8/2004 | Atala et al. |
| 2004/0193098 A1 | 9/2004 | Wentling et al. |
| 2005/0042240 A1 | 2/2005 | Utterberg et al. |
| 2005/0049575 A1 | 3/2005 | Snell et al. |
| 2005/0049577 A1 | 3/2005 | Snell et al. |
| 2005/0101941 A1 | 5/2005 | Hakky et al. |
| 2005/0107736 A1 | 5/2005 | Landman et al. |
| 2005/0124969 A1 | 6/2005 | Fitzgerald et al. |
| 2005/0124978 A1 | 6/2005 | Kim |
| 2005/0177102 A1 | 8/2005 | Hart et al. |
| 2005/0187564 A1 | 8/2005 | Jayaraman |
| 2005/0240141 A1 | 10/2005 | Aliski et al. |
| 2005/0240280 A1 | 10/2005 | Aliski et al. |
| 2005/0256441 A1 | 11/2005 | Lotan et al. |
| 2005/0256447 A1 | 11/2005 | Richardson et al. |
| 2005/0288722 A1 | 12/2005 | Eigler et al. |
| 2006/0015015 A1 | 1/2006 | Kawamoto et al. |
| 2006/0015089 A1 | 1/2006 | Meglin et al. |
| 2006/0052879 A1 | 3/2006 | Kolb |
| 2006/0074388 A1 | 4/2006 | Dextradeur et al. |
| 2006/0074409 A1 | 4/2006 | Schuermann |
| 2006/0229553 A1 | 10/2006 | Hammack et al. |
| 2006/0229573 A1 | 10/2006 | Lamborne |
| 2006/0259151 A1 | 11/2006 | Ward |
| 2006/0271019 A1 | 11/2006 | Stoller et al. |
| 2007/0010797 A1 | 1/2007 | Nishtala et al. |
| 2007/0010798 A1 | 1/2007 | Stoller et al. |
| 2007/0055198 A1 | 3/2007 | O'Mahony et al. |
| 2007/0073271 A1 | 3/2007 | Brucker et al. |
| 2007/0088333 A1 | 4/2007 | Levin et al. |
| 2007/0112302 A1 | 5/2007 | Yu |
| 2007/0197957 A1 | 8/2007 | Hunter et al. |
| 2007/0208291 A1 | 9/2007 | Patel |
| 2007/0213665 A1 | 9/2007 | Curtin et al. |
| 2007/0219488 A1 | 9/2007 | Francescatti |
| 2007/0255230 A1 | 11/2007 | Gross et al. |
| 2008/0051678 A1 | 2/2008 | Lindahl |
| 2008/0051691 A1 | 2/2008 | Dragoon et al. |
| 2008/0058650 A1 | 3/2008 | Saadat et al. |
| 2008/0097463 A1 | 4/2008 | House |
| 2008/0119907 A1 | 5/2008 | Stahmann |
| 2008/0142023 A1 | 6/2008 | Schmid et al. |
| 2008/0183299 A1 | 7/2008 | Monga et al. |
| 2008/0215247 A1 | 9/2008 | Tonelli et al. |
| 2008/0243091 A1 | 10/2008 | Humphreys et al. |
| 2008/0255550 A1 | 10/2008 | Bell |
| 2008/0281291 A1 | 11/2008 | Tihon et al. |
| 2008/0288082 A1 | 11/2008 | Deal |
| 2008/0312550 A1 | 12/2008 | Nishtala et al. |
| 2009/0024091 A1 | 1/2009 | Li et al. |
| 2009/0030370 A1 | 1/2009 | Nishtala et al. |
| 2009/0030435 A1 | 1/2009 | Burnett et al. |
| 2009/0043229 A1 | 2/2009 | Dunn et al. |
| 2009/0088677 A1 | 4/2009 | Cohen |
| 2009/0093748 A1 | 4/2009 | Patterson et al. |
| 2009/0105719 A1 | 4/2009 | Honey et al. |
| 2009/0143713 A1 | 6/2009 | Van Dam et al. |

(56) References Cited

U.S. PATENT DOCUMENTS

| | | |
|---|---|---|
| 2009/0162530 A1 | 6/2009 | Nesbitt |
| 2009/0171137 A1 | 7/2009 | Farnan et al. |
| 2009/0171241 A1 | 7/2009 | Garcia et al. |
| 2009/0281507 A1 | 11/2009 | Humphreys |
| 2009/0318844 A1 | 12/2009 | Burnett |
| 2010/0057000 A1 | 3/2010 | Melsheimer et al. |
| 2010/0081148 A1 | 4/2010 | Singbartl et al. |
| 2010/0086580 A1 | 4/2010 | Nyman et al. |
| 2010/0121159 A1 | 5/2010 | Burnett et al. |
| 2010/0191183 A1 | 7/2010 | Tanghoej et al. |
| 2010/0204682 A1 | 8/2010 | Tanghoj et al. |
| 2010/0241240 A1 | 9/2010 | Willard et al. |
| 2010/0261985 A1 | 10/2010 | Cohen-Solal et al. |
| 2010/0298857 A1 | 11/2010 | Zook et al. |
| 2010/0312163 A1 | 12/2010 | Forsell |
| 2011/0009799 A1 | 1/2011 | Mullick et al. |
| 2011/0009831 A1 | 1/2011 | Burkholz et al. |
| 2011/0015558 A1 | 1/2011 | Kaye et al. |
| 2011/0089111 A1 | 4/2011 | Mori et al. |
| 2011/0098683 A1 | 4/2011 | Wiita et al. |
| 2011/0118537 A1 | 5/2011 | Wampler |
| 2011/0132838 A1 | 6/2011 | Curtis et al. |
| 2011/0208319 A1 | 8/2011 | Laster |
| 2011/0230950 A1 | 9/2011 | Knapp |
| 2011/0238163 A1 | 9/2011 | Andrews et al. |
| 2011/0269167 A1 | 11/2011 | Bene |
| 2011/0276024 A1 | 11/2011 | Randolph et al. |
| 2011/0282264 A1 | 11/2011 | Hurt |
| 2011/0301553 A1 | 12/2011 | Goral et al. |
| 2011/0301662 A1 | 12/2011 | Bar-Yoseph et al. |
| 2011/0320008 A1 | 12/2011 | Teague et al. |
| 2012/0016335 A1* | 1/2012 | Eshel ................ A61M 3/0208 604/500 |
| 2012/0029937 A1 | 2/2012 | Neftel et al. |
| 2012/0042427 A1 | 2/2012 | Messier |
| 2012/0053700 A1 | 3/2012 | Rickner |
| 2012/0078226 A1 | 3/2012 | Latere Dwan'isa et al. |
| 2012/0083899 A1 | 4/2012 | Whitmore, III |
| 2012/0107420 A1 | 5/2012 | Breit et al. |
| 2012/0136343 A1 | 5/2012 | Burnett |
| 2012/0154264 A1 | 6/2012 | Wang et al. |
| 2012/0165641 A1 | 6/2012 | Burnett et al. |
| 2012/0179144 A1 | 7/2012 | Carleo |
| 2012/0179145 A1 | 7/2012 | Nishtala et al. |
| 2012/0220926 A1 | 8/2012 | Soykan et al. |
| 2012/0238802 A1 | 9/2012 | Knight et al. |
| 2012/0265020 A1 | 10/2012 | Pandey et al. |
| 2012/0277155 A1 | 11/2012 | VanAntwerp et al. |
| 2012/0316656 A1 | 12/2012 | Deal et al. |
| 2013/0030262 A1 | 1/2013 | Burnett et al. |
| 2013/0066166 A1 | 3/2013 | Burnett et al. |
| 2013/0085468 A1 | 4/2013 | Buydenok |
| 2013/0090648 A1 | 4/2013 | Nagale et al. |
| 2013/0131621 A1 | 5/2013 | Van Holten et al. |
| 2013/0138077 A1 | 5/2013 | O'Day |
| 2013/0150828 A1 | 6/2013 | Conway |
| 2013/0172807 A1 | 7/2013 | Cruz |
| 2013/0172881 A1 | 7/2013 | Hill et al. |
| 2013/0184545 A1 | 7/2013 | Blomqvist et al. |
| 2013/0187563 A1 | 7/2013 | Sasai et al. |
| 2013/0197471 A1 | 8/2013 | Williams et al. |
| 2013/0199998 A1 | 8/2013 | Kelly et al. |
| 2013/0218135 A1 | 8/2013 | Dein |
| 2013/0231640 A1 | 9/2013 | Terry et al. |
| 2013/0231752 A1 | 9/2013 | Rosenbaum et al. |
| 2013/0253409 A1 | 9/2013 | Burnett |
| 2013/0267845 A1 | 10/2013 | Howle et al. |
| 2013/0274644 A1 | 10/2013 | Hertz |
| 2013/0274783 A1 | 10/2013 | Wynberg |
| 2013/0303865 A1 | 11/2013 | Rebec et al. |
| 2013/0303961 A1 | 11/2013 | Wolff et al. |
| 2013/0304082 A1 | 11/2013 | Aklog et al. |
| 2013/0317322 A1 | 11/2013 | Andrijauskas |
| 2013/0331824 A1 | 12/2013 | Kim |
| 2013/0338580 A1 | 12/2013 | Yamatani et al. |
| 2013/0345670 A1 | 12/2013 | Rajagopalan et al. |
| 2014/0031773 A1 | 1/2014 | Mikkaichi |
| 2014/0031787 A1 | 1/2014 | Burnes et al. |
| 2014/0039375 A1 | 2/2014 | Jimenez et al. |
| 2014/0058316 A1 | 2/2014 | Gupta et al. |
| 2014/0073926 A1 | 3/2014 | Rajendran et al. |
| 2014/0074144 A1 | 3/2014 | Shrivastava et al. |
| 2014/0135941 A1 | 5/2014 | Smouse et al. |
| 2014/0142539 A1 | 5/2014 | Salinas et al. |
| 2014/0148648 A1 | 5/2014 | Tycast et al. |
| 2014/0148754 A1 | 5/2014 | Soykan et al. |
| 2014/0155818 A1 | 6/2014 | Salinas et al. |
| 2014/0188248 A1 | 7/2014 | Gandhi |
| 2014/0188249 A1 | 7/2014 | Pendleton et al. |
| 2014/0214009 A1 | 7/2014 | Reyes |
| 2014/0228801 A1 | 8/2014 | Keeling |
| 2014/0275984 A1 | 9/2014 | Hermann et al. |
| 2014/0276341 A1 | 9/2014 | Ludin et al. |
| 2014/0276628 A1 | 9/2014 | Gandras et al. |
| 2014/0364820 A1 | 12/2014 | Solazzo et al. |
| 2015/0011855 A1 | 1/2015 | Burnett et al. |
| 2015/0011928 A1 | 1/2015 | Burnett |
| 2015/0017682 A1 | 1/2015 | Adam |
| 2015/0065783 A1 | 3/2015 | Buelna |
| 2015/0080844 A1 | 3/2015 | Donovan et al. |
| 2015/0094548 A1 | 4/2015 | Sabatini et al. |
| 2015/0094644 A1* | 4/2015 | Lenihan ................ A61M 39/24 604/9 |
| 2015/0094696 A1 | 4/2015 | Adams, Jr. et al. |
| 2015/0100009 A1 | 4/2015 | Bearss |
| 2015/0134073 A1 | 5/2015 | Tang et al. |
| 2015/0164370 A1 | 6/2015 | Wabel et al. |
| 2015/0194052 A1 | 7/2015 | Sagan et al. |
| 2015/0223953 A1 | 8/2015 | Pendleton et al. |
| 2015/0224241 A1 | 8/2015 | Fontanazzi et al. |
| 2015/0273120 A1 | 10/2015 | Zamarripa et al. |
| 2015/0283362 A1 | 10/2015 | Shelton et al. |
| 2015/0290411 A1 | 10/2015 | Warrington et al. |
| 2015/0306364 A1 | 10/2015 | Shevgoor |
| 2015/0328027 A1 | 11/2015 | Nishio et al. |
| 2015/0352339 A1 | 12/2015 | Wang |
| 2016/0051176 A1 | 2/2016 | Ramos et al. |
| 2016/0058489 A1 | 3/2016 | Fischell et al. |
| 2016/0183819 A1* | 6/2016 | Burnett ................ A61B 5/0084 600/561 |
| 2016/0213881 A9 | 7/2016 | Adams, Jr. et al. |
| 2016/0303303 A1 | 10/2016 | Rovatti et al. |
| 2016/0310711 A1 | 10/2016 | Luxon et al. |
| 2016/0331294 A1 | 11/2016 | Imran et al. |
| 2016/0367747 A1 | 12/2016 | Loske |
| 2017/0020724 A1 | 1/2017 | Burnett et al. |
| 2017/0021128 A1 | 1/2017 | Erbey et al. |
| 2017/0095323 A1 | 4/2017 | Garcia |
| 2017/0095641 A1 | 4/2017 | Scarpine et al. |
| 2017/0113000 A1 | 4/2017 | Tobescu et al. |
| 2017/0119519 A1 | 5/2017 | Sambusseti et al. |
| 2017/0128639 A1 | 5/2017 | Erbey, II et al. |
| 2017/0128654 A1 | 5/2017 | Feld |
| 2017/0136222 A1 | 5/2017 | Hakim et al. |
| 2017/0196576 A1 | 7/2017 | Long et al. |
| 2017/0197028 A1 | 7/2017 | Goldsmith |
| 2017/0232153 A1 | 8/2017 | Babu et al. |
| 2017/0266414 A1 | 9/2017 | Rocha-Singh et al. |
| 2017/0325927 A1 | 11/2017 | Gobel |
| 2017/0348507 A1 | 12/2017 | Erbey, II et al. |
| 2017/0348512 A1 | 12/2017 | Orr et al. |
| 2017/0367636 A1 | 12/2017 | Mantinband et al. |
| 2018/0001055 A1 | 1/2018 | Utas et al. |
| 2018/0116751 A1 | 5/2018 | Schwartz et al. |
| 2018/0117288 A1 | 5/2018 | Lindsay et al. |
| 2018/0169313 A1 | 6/2018 | Schwammenthal et al. |
| 2018/0177458 A1 | 6/2018 | Burnett |
| 2018/0193618 A1 | 7/2018 | Erbey, II et al. |
| 2018/0207412 A1 | 7/2018 | Malek et al. |
| 2018/0344250 A1 | 12/2018 | McKinney et al. |
| 2019/0030303 A1 | 1/2019 | Holman et al. |
| 2019/0091442 A1 | 3/2019 | Erbey, II et al. |
| 2019/0105465 A1 | 4/2019 | Erbey, II et al. |
| 2019/0201662 A1 | 7/2019 | Lad et al. |

(56) References Cited

U.S. PATENT DOCUMENTS

| | | |
|---|---|---|
| 2019/0240448 A1 | 8/2019 | Murdock |
| 2019/0247615 A1 | 8/2019 | Bishawi |
| 2020/0001045 A1 | 1/2020 | McIntyre |
| 2020/0094017 A1 | 3/2020 | Erbey, II et al. |
| 2021/0178133 A1 | 6/2021 | Walish et al. |

FOREIGN PATENT DOCUMENTS

| | | | |
|---|---|---|---|
| CA | 2363001 C | 9/2000 | |
| CA | 2205473 C | 6/2006 | |
| CA | 2992546 A1 | 1/2017 | |
| CA | 2992322 C | 8/2019 | |
| CN | 2175619 Y | 8/1994 | |
| CN | 2562776 Y | 7/2003 | |
| CN | 2588940 Y | 12/2003 | |
| CN | 1479596 A | 3/2004 | |
| CN | 2753382 Y | 1/2006 | |
| CN | 2928043 Y | 8/2007 | |
| CN | 101224148 A | 7/2008 | |
| CN | 101426540 A | 5/2009 | |
| CN | 201814968 U | 5/2011 | |
| CN | 102176928 A | 9/2011 | |
| CN | 202459720 U | 10/2012 | |
| CN | 202526754 U | 11/2012 | |
| CN | 202802478 U | 3/2013 | |
| CN | 103096964 A | 5/2013 | |
| CN | 103203062 A | 7/2013 | |
| CN | 103841905 A | 6/2014 | |
| CN | 203777060 U | 8/2014 | |
| CN | 203842151 U | 9/2014 | |
| CN | 204158867 U | 2/2015 | |
| CN | 204246651 U | 4/2015 | |
| CN | 204446944 U | 7/2015 | |
| CN | 205126495 U | 4/2016 | |
| CN | 106237417 A | 12/2016 | |
| CN | 106473847 A | 3/2017 | |
| CN | 106693092 A | 5/2017 | |
| CN | 107261294 A | 10/2017 | |
| DE | 102012016049 A1 * | 2/2014 | ............ A61M 1/008 |
| EP | 873760 A1 | 10/1998 | |
| EP | 1011803 B1 | 9/2004 | |
| EP | 1980292 A2 | 10/2008 | |
| EP | 3325076 A2 | 5/2018 | |
| EP | 3470107 A1 | 4/2019 | |
| EP | 3488897 A1 | 5/2019 | |
| EP | 3970775 A1 | 3/2022 | |
| FR | 3052671 A1 | 12/2017 | |
| JP | 59111748 A | 6/1984 | |
| JP | H42361 A | 1/1992 | |
| JP | H10504469 | 5/1998 | |
| JP | 2002510536 A | 4/2002 | |
| JP | 2002291879 A | 10/2002 | |
| JP | 200253888 | 11/2002 | |
| JP | 2002537893 A | 11/2002 | |
| JP | 2003530165 A | 10/2003 | |
| JP | 2004215787 A | 8/2004 | |
| JP | 2006516214 A | 6/2006 | |
| JP | 2006526464 A | 11/2006 | |
| JP | 2009505802 A | 2/2009 | |
| JP | 2009238520 A | 10/2009 | |
| JP | 2009537256 A | 10/2009 | |
| JP | 201005282 A | 1/2010 | |
| JP | 2010508984 A | 3/2010 | |
| JP | 2010119737 A | 6/2010 | |
| JP | 2010230618 A | 10/2010 | |
| JP | 2013149498 A | 1/2012 | |
| JP | 2012505022 A | 3/2012 | |
| JP | 2014136116 A | 7/2014 | |
| JP | 2014176689 A | 9/2014 | |
| RU | 2113245 C1 | 6/1998 | |
| RU | 2300399 C1 | 6/2007 | |
| RU | 149161 U1 | 12/2014 | |
| TW | M540625 U | 5/2017 | |
| WO | 9529716 A1 | 11/1995 | |
| WO | 9716218 A1 | 5/1997 | |
| WO | 9816171 A1 | 4/1998 | |
| WO | 9850088 A1 | 11/1998 | |
| WO | 0054701 A1 | 9/2000 | |
| WO | 0160260 A1 | 8/2001 | |
| WO | 6558350 A1 | 12/2001 | |
| WO | 03017870 A1 | 3/2003 | |
| WO | 2004064681 A1 | 8/2004 | |
| WO | 2006017439 A2 | 2/2006 | |
| WO | 2006023589 A2 | 3/2006 | |
| WO | 2006044621 A2 | 4/2006 | |
| WO | 2007001978 A2 | 1/2007 | |
| WO | 2007027830 A1 | 3/2007 | |
| WO | 2008066625 A1 | 6/2008 | |
| WO | 2010082197 A2 | 7/2010 | |
| WO | 2011109570 A2 | 9/2011 | |
| WO | 2011139498 A1 | 11/2011 | |
| WO | 197896 A1 | 12/2011 | |
| WO | 2013022005 A1 | 2/2013 | |
| WO | 2013029622 A1 | 3/2013 | |
| WO | 2014025367 A1 | 2/2014 | |
| WO | 2014043650 A2 | 3/2014 | |
| WO | 2014062225 A1 | 4/2014 | |
| WO | 2015105916 A1 | 7/2015 | |
| WO | 2015157467 A1 | 10/2015 | |
| WO | 2015198333 A1 | 12/2015 | |
| WO | 2016049654 A1 | 3/2016 | |
| WO | 2016103256 A1 | 6/2016 | |
| WO | 2017015345 A2 | 1/2017 | |
| WO | 2017015351 A2 | 1/2017 | |
| WO | 2017019974 A1 | 2/2017 | |
| WO | 2017087182 A1 | 5/2017 | |
| WO | 2018136603 A1 | 7/2018 | |
| WO | 2018186781 A1 | 10/2018 | |
| WO | 2018200050 A1 | 11/2018 | |
| WO | 2019038730 A1 | 2/2019 | |
| WO | 2020236748 A1 | 11/2020 | |

OTHER PUBLICATIONS

Mordi et al., "Renal and Cardiovascular Effects of sodium-glucose cotransporter 2 (SGLT2) inhibition with loop Diuretics in diabetic patents with Chronic Heart Failure (REEDE-CHF): protocol for a randomised controlled double-blind cross-over trail". BJM open, 2017, vol. 7, pp. 1-9.

Quadra-Coil | Olympus America | Medical, Ureteral Stents, https://www.medical.olympusamerica.com/products/quadra-coil (downloaded from the Internet Aug. 31, 2022) 2 pages.

Stents—Urology | Olympus America | Medical. Ureteral Stents, https://www.medical.olympusamerica.com/products/stents-Urology (downloaded from the Internet Aug. 31, 2022) 2 pages.

Ureteral stent—Quadra-Coil—Olympus Medical Europa, https://www.medicalexpo.com/prod/olympus-medical-europa/product-69587-661607.html (downloaded from the Internet Aug. 31, 2022) 5 pages.

U.S. Pat. No. 10,307,564 / U.S. Appl. No. 15/214,955, "Ureteral and Bladder Catheters and Methods of Inducing Negative Pressure to Increase Renal Perfusion", Jun. 4, 2019 / filed Jul. 20, 2016.

U.S. Pat. No. 9,744,331 / U.S. Appl. No. 15/215,081, "Ureteral and Bladder Catheters and Methods of Inducing Negative Pressure to Increase Renal Perfusion", Aug. 29, 2017 / filed Jul. 20, 2016.

U.S. Pat. No. 10,512,713 / U.S. Appl. No. 15/411,884, "Method of Removing Excess Fluid from a Patient with Hemodilution", Dec. 24, 2019 / filed Jan. 20, 2017.

U.S. Pat. No. 10,601,664 / U.S. Appl. No. 15/673,706, "Ureteral and Bladder Catheters and Methods of Inducing Negative Pressure to Increase Renal Perfusion", Apr. 7, 2020 / filed Aug. 10, 2017.

U.S. Pat. No. 10,765,834 / U.S. Appl. No. 15/687,064, "Ureteral and Bladder Catheters and Methods of Inducing Negative Pressure to Increase Renal Perfusion" Aug. 8, 2020 / filed Aug. 25, 2017.

U.S. Pat. No. 10,926,062 / U.S. Appl. No. 15/687,083, "Ureteral and Bladder Catheters and Methods of Inducing Negative Pressure to Increase Renal Perfusion", Feb. 23, 2021 / filed Aug. 25, 2017.

U.S. Pat. No. 11,040,172/ U.S. Appl. No. 15/879,976, "Ureteral and Bladder Catheters and Methods of Inducing Negative Pressure to Increase Renal Perfusion", Jun. 22, 2021 / filed Jan. 25, 2018.

(56) References Cited

OTHER PUBLICATIONS

U.S. Pat. No. 10,918,827 / U.S. Appl. No. 15/879,869, "Catheter Device and Method for Inducing Negative Pressure in a Patient's Bladder", Frb. 16, 2021 / filed Jan. 25, 2018.
U.S. Appl. No. 15/745,823, "Catheter Device and Method for Inducing Negative Pressure in a Patient's Bladder", filed Jul. 20, 2016.
U.S. Pat. No. 11,040,180/ U.S. Appl. No. 15/879,770, "Systems, Kits and Methods for Inducing Negative Pressure to Increase Renal Function", Jun. 22, 2021 / filed Jan. 25, 2018.
U.S. Pat. No. 10,918,825 / U.S. Appl. No. 16/012,233, "Ureteral and Bladder Catheters and Methods of Inducing Negative Pressure to Increase Renal Perfusion", Feb. 16, 2021 / filed Jun. 19, 2018.
U.S. Pat. No. 11,077,284 / U.S. Appl. No. 16/036,971, "Ureteral and Bladder Catheters and Methods of Inducing Negative Pressure to Increase Renal Perfusion", Aug. 3, 2021 / filed Jul. 17, 2018.
U.S. Appl. No. 16/206,207, "Percutaneous Ureteral Catheter", filed Nov. 30, 2018.
U.S. Appl. No. 16/206,389, "Coated Ureteral Catheter or Ureteral Stent and Method", filed Nov. 30, 2018.
U.S. Pat. No. 10,493,232 / U.S. Appl. No. 16/205,987, "Ureteral Catheters, Bladder Catheters, Systems, Kits and Methods for Inducing Negative Pressure to Increase Renal Function", Dec. 3, 2019 / Nov. 30, 2018.
U.S. Pat. No. 10,426,919 / U.S. Appl. No. 16/257,791, "Systems and Methods for Inducing Negative Pressure in a Portion of a Urinary Tract of a Patient", Oct. 1, 2019 / filed Jan. 25, 2019.
U.S. Appl. No. 16/390,154, "Ureteral and Bladder Catheters and Methods of Inducing Negative Pressure to Increase Renal Perfusion", filed Apr. 22, 2019.
U.S. Appl. No. 16/542,680, "Systems and Methods for Inducing Negative Pressure in a Portion of a Urinary Tract of a Patient", filed Aug. 16, 2019.
U.S. Appl. No. 16/670,249, "Method of Removing Excess Fluids from a Patient with Hemodilution", filed Oct. 31, 2019.
U.S. Pat. No. 10,799,668 / U.S. Appl. No. 16/662,536, "Ureteral Catheters, Bladder Catheters, Systems, Kits and Methods for Inducing Negative Pressure to Increase Renal Function", Oct. 13, 2020 / filed Oct. 24, 2019.
U.S. Appl. No. 16/662,212, "Catheter and Method for Inducing Negative Pressure in a Patient's Bladder", filed Oct. 24, 2019.
U.S. Appl. No. 16/696,026, "Coated and/or Impregnated Ureteral Catheter or Stent and Method", filed Nov. 26, 2019.
U.S. Appl. No. 16/850,052, "Method of Removing Excess Fluid from a Patient with Venous Congestion", filed Apr. 16, 2020.
U.S. Appl. No. 16/820,781, "Ureteral and Bladder Catheters and Methods of Inducing Negative Pressure to Increase Renal Perfusion", filed Mar. 17, 2020.
U.S. Appl. No. 16/640,210, "Indwelling Pump for Facilitating Removal of Urine from the Urinary Tract", filed Aug. 24, 2018.
U.S. Appl. No. 16/817,773, "Ureteral and Bladder Catheters and Methods of Inducing Negative Pressure to Increase Renal Perfusion", filed Mar. 13, 2020.
U.S. Appl. No. 16/826,347, "Ureteral Catheters, Bladder Catheters, Systems, Kits and Methods for Inducing Negative Pressure to Increase Renal Function", filed Mar. 23, 2020.
U.S. Appl. No. 16/835,973, "Catheter Device and Method for Inducing Negative Pressure in a Patient's Bladder", filed Mar. 31, 2020.
U.S. Appl. No. 16/856,339, "Pump Assembly and System for Inducing Negative Pressure in a Portion of a Urinary Tract of a Patient", filed Apr. 23, 2020.
U.S. Appl. No. 16/872,965, "Ureteral and Bladder Catheters and Methods of Inducing Negative Pressure to Increase Renal Perfusion", filed May 12, 2020.
U.S. Appl. No. 17/077,793, "Ureteral and Bladder Catheters and Methods of Inducing Negative Pressure to Increase Renal Perfusion", filed Oct. 22, 2020.

U.S. Appl. No. 17/089,757, "Catheter Device and Method for Inducing Negative Pressure in a Patient's Bladder", filed Nov. 5, 2020.
U.S. Appl. No. 17/154,004, "Negative Pressure Therapy System", filed Jan. 20, 2021.
U.S. Appl. No. 17/152,636, "Systems, Kits and Methods for Inducing Negative Pressure to Increase Renal Function", filed Jan. 19, 2021.
U.S. Appl. No. 17/173,262, "Ureteral and Bladder Catheters and Methods of Inducing Negative Pressure to Increase Renal Perfusion", filed Feb. 11, 2021.
U.S. Appl. No. 17/238,454, "Method of Treatment Using Negative Pressure Renal Therapy and Medicament(s)", filed Apr. 23, 2021.
U.S. Appl. No. 17/340,858, "Ureteral and Bladder Catheters and Methods of Inducing Negative Pressure to Increase Renal Perfusion", filed Jun. 7, 2021.
Bart et al.; "Ultrafiltration in Decompensated Heart Failure with Cardiorenal Syndrome"; N Engl J Med; 2012; p. 2296-2304; vol. 367.
Burr et al.; "Urinary catheter blockage depends on urine pH, calcium and rate of flow"; Spinal Cord; 1997; p. 521-525; vol. 35.
Clinical Practice Guidelines for Chronic Kidney Disease: Evaluation, Classification and Stratification; National Kidney Foundation; Am. J. Kidney Dis.; 2002; p. S1-S266; Suppl. 1.
"The Criteria Committee of the New York Heart Association", (1994), Nomenclature and Criteria for Diagnosis of Diseases of the Heart and Great Vessels, (9th ed.), Boston: Little, Brown Co. p. 253-256 (Abstract).
Harris et al., "Relationship between patients outcomes and the changes in serum creatinine and urine output and RIFLE classification in a large critical care cohort database", Kidney International, 2015, p. 369-377, vol. 88.
Jessup et al.; "The Cardiorenal Syndrome—Do We Need a Change of Strategy or a Change of Tactics"; Journal of the American College of Cardiology; 2009; p. 597-599; vol. 53:7.
Mardis et al., "Comparative Evaluation of Materials Used for Internal Ureteral Stents", Journal of Endourology, 1993, pp. 105-115, vol. 7:2.
Mullens et al.; "Importance of Venous Congestion for Worsening of Renal Function in Advanced Decompensated Heart Failure"; Journal of the American College of Cardiology; 2009; p. 589-596; vol. 53:7.
Peters et al.; "Short and Long-Term Effects of the Angiotensin II Receptor Blocker Irbesartan on Intradialytic Central Hemodynamics: A Randomized Double-Blind Placebo-Controlled One-Year Intervention Trial (the SAFIR Study)"; PLoS ONE; Jun. 1, 2015; p. 1-22.
"Standard Specification for Ureteral Stents", ASTM International, 2014, Designation F1828-97, p. 1-6.
Verbrugge et al.; "The kidney in congestive heart failure: are natriuresis, sodium, and diuretics really the good, the bad and the ugly"; European Journal of Heart Failure; 2014; p. 133-142; vol. 16.
Wolf, Jr. et al.; "Comparative Ureteral Microanatomy"; Journal of Endourology; 1996; p. 527-531; vol. 10:6.
Wolf, Jr. et al.; "Comparative Ureteral Microanatomy"; Journal of Endourology; 1996; p. 527-531; vol. 10:6.
Zelenko et al.; "Normal Ureter Size on Unenhanced Helical CT"; American Journal of Roentgenology; 2004; p. 1039-1041; vol. 182.
Damman et al., "Increased Central Venous Pressure is Associated With Impaired Renal Function and Mortality in a Broad Spectrum of XPatients With Cardiovascular Disease", 2009, Journal of the American College of Cardiology, vol. 53:7, pp. 582-588.
Dixon et al., "The musculature of the human renal calices, pelvis and upper ureter", J, Anat., 1982, vol. 135, pp. 129-137.
Gregersen et al., "Regional Differences Exist in Elastic Wall Properties in the Ureter", SJUN, 1996, vol. 30, pp. 343-348.
Kiil, "Urinary Flow and Ureteral Peristalsis" in: Lutzeyer W., Melchior H. (Eds.) Urodynamics, 1973 Springer, Berlin, Heidelberg (pp. 57-70).
Lala et al., "Relief and Recurrence of Congestion During and After Hospitalization for Acute Heart Failure: Insights from DOSE-AHF and CARRESS-HF", Circ Heart Fail, 2015, vol. 8:4, pp. 741-748.

(56) References Cited

OTHER PUBLICATIONS

Legrand et al. "Association between systemic hemodynamics and septic acute kidney injury in critically ill patients: a retrospective observational study", Critical Care, 2013, vol. 17:R278, pp. 1-8.
Nohria et al., "Cardiorenal Interactions Insights from the ESCAPE Trial", Heart Failure, 2008, vol. 51:13, pp. 1268-1274.
Uthoff et al., "Central venous pressure and impaired renal function in patients with acute heart failure", European Journal of Heart Failure, 2011. vol. 13, pp. 432-439.
Walker, "Annals of Surgery" 1913, Lippincott Williams & Wilkins, p. 58, Figures 3 and 9.
Webb, "Percutaneous Renal Surgery: A Practical Clinical Handbook", 2016, Springer International Publishing, Switzerland, p. 92.
Woodburne et al., "The Uretal Lumen during Peristalsis", Am. J. Anat., 1972. vol. 133, pp. 255-258.

\* cited by examiner

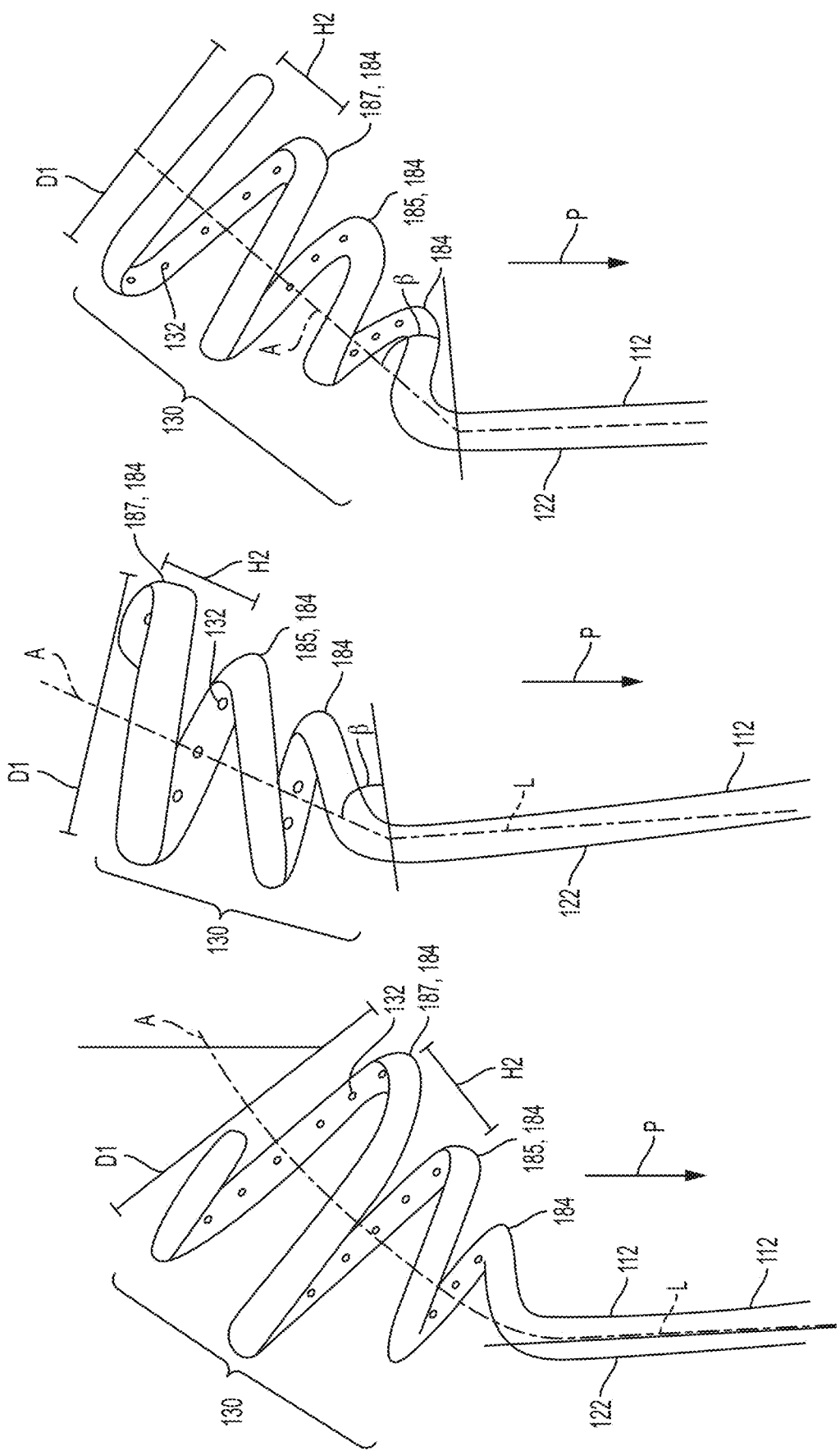

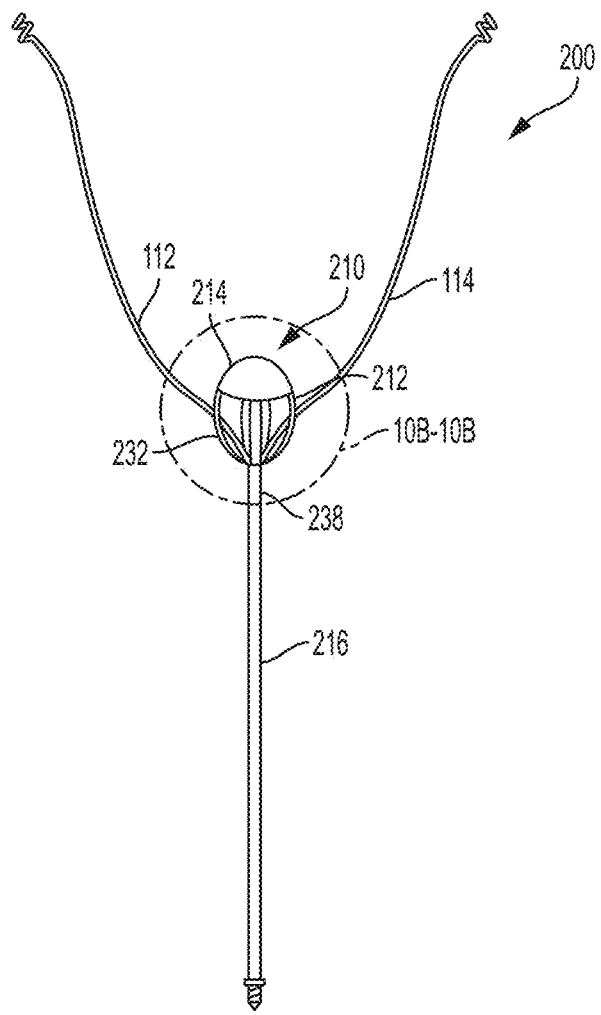
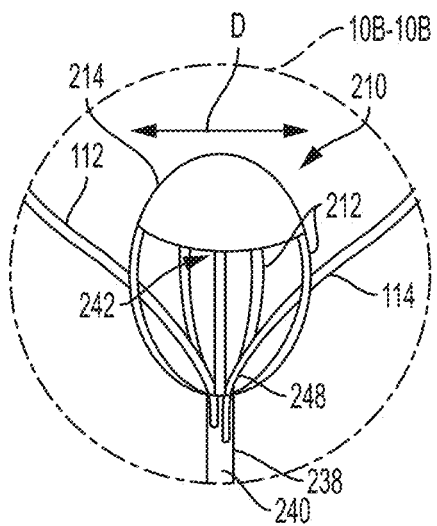
FIG. 10A
FIG. 10B

NEGATIVE PRESSURE THERAPY SYSTEM

CROSS REFERENCE TO RELATED APPLICATIONS

This application is a continuation of U.S. application Ser. No. 16/036,971, filed Jul. 17, 2018, which is a continuation of U.S. application Ser. No. 15/214,955, filed Jul. 20, 2016, now issued as U.S. Pat. No. 10,307,564, which claims the benefit of U.S. Provisional Application No. 62/194,585, filed Jul. 20, 2015, U.S. Provisional Application No. 62/260,966 filed Nov. 30, 2015, U.S. Provisional Application No. 62/278,721, filed Jan. 14, 2016, and U.S. Provisional Application No. 62/300,025 filed Feb. 25, 2016, each of which is incorporated herein by reference in its entirety.

BACKGROUND

Technical Field

The present disclosure relates to methods and devices for treating impaired renal function across a variety of disease states and, in particular, to catheter devices, assemblies, and methods for collection of urine and/or inducement of negative pressure in the ureters and/or kidneys.

Background

The renal or urinary system includes a pair of kidneys, each kidney being connected by a ureter to the bladder, and a urethra for draining urine produced by the kidneys from the bladder. The kidneys perform several vital functions for the human body including, for example, filtering the blood to eliminate waste in the form of urine. The kidneys also regulate electrolytes (e.g., sodium, potassium and calcium) and metabolites, blood volume, blood pressure, blood pH, fluid volume, production of red blood cells, and bone metabolism. Adequate understanding of the anatomy and physiology of the kidneys is useful for understanding the impact that altered hemodynamics other fluid overload conditions have on their function.

In normal anatomy, the two kidneys are located retroperitoneally in the abdominal cavity. The kidneys are bean-shaped encapsulated organs. Urine is formed by nephrons, the functional unit of the kidney, and then flows through a system of converging tubules called collecting ducts. The collecting ducts join together to form minor calyces, then major calyces, which ultimately join near the concave portion of the kidney (renal pelvis). A major function of the renal pelvis is to direct urine flow to the ureter. Urine flows from the renal pelvis into the ureter, a tube-like structure that carries the urine from the kidneys into the bladder. The outer layer of the kidney is called the cortex, and is a rigid fibrous encapsulation. The interior of the kidney is called the medulla. The medulla structures are arranged in pyramids.

Each kidney is made up of approximately one million nephrons. Each nephron includes the glomerulus, Bowman's capsule, and tubules. The tubules include the proximal convoluted tubule, the loop of Henle, the distal convoluted tubule, and the collecting duct. The nephrons contained in the cortex layer of the kidney are distinct from the anatomy of those contained in the medulla. The principal difference is the length of the loop of Henle. Medullary nephrons contain a longer loop of Henle, which, under normal circumstances, allows greater regulation of water and sodium reabsorption than in the cortex nephrons.

The glomerulus is the beginning of the nephron, and is responsible for the initial filtration of blood. Afferent arterioles pass blood into the glomerular capillaries, where hydrostatic pressure pushes water and solutes into Bowman's capsule. Net filtration pressure is expressed as the hydrostatic pressure in the afferent arteriole minus the hydrostatic pressure in Bowman's space minus the osmotic pressure in the efferent arteriole.

Net Filtration Pressure=Hydrostatic Pressure (Afferent Arteriole)−Hydrostatic Pressure (Bowman's Space)−Osmotic Pressure (Efferent Arteriole)  (Equation 1)

The magnitude of this net filtration pressure defined by Equation 1 determines how much ultra-filtrate is formed in Bowman's space and delivered to the tubules. The remaining blood exits the glomerulus via the efferent arteriole. Normal glomerular filtration, or delivery of ultra-filtrate into the tubules, is about 90 ml/min/1.73 m$^2$.

The glomerulus has a three-layer filtration structure, which includes the vascular endothelium, a glomerular basement membrane, and podocytes. Normally, large proteins such as albumin and red blood cells, are not filtered into Bowman's space. However, elevated glomerular pressures and mesangial expansion create surface area changes on the basement membrane and larger fenestrations between the podocytes allowing larger proteins to pass into Bowman's space.

Ultra-filtrate collected in Bowman's space is delivered first to the proximal convoluted tubule. Re-absorption and secretion of water and solutes in the tubules is performed by a mix of active transport channels and passive pressure gradients. The proximal convoluted tubules normally reabsorb a majority of the sodium chloride and water, and nearly all glucose and amino acids that were filtered by the glomerulus. The loop of Henle has two components that are designed to concentrate wastes in the urine. The descending limb is highly water permeable and reabsorbs most of the remaining water. The ascending limb reabsorbs 25% of the remaining sodium chloride, creating a concentrated urine, for example, in terms of urea and creatinine. The distal convoluted tubule normally reabsorbs a small proportion of sodium chloride, and the osmotic gradient creates conditions for the water to follow.

Under normal conditions, there is a net filtration of approximately 14 mmHg. The impact of venous congestion can be a significant decrease in net filtration, down to approximately 4 mmHg. See Jessup M., *The cardiorenal syndrome: Do we need a change of strategy or a change of tactics?*, JACC 53(7):597-600, 2009 (hereinafter "Jessup"). The second filtration stage occurs at the proximal tubules. Most of the secretion and absorption from urine occurs in tubules in the medullary nephrons. Active transport of sodium from the tubule into the interstitial space initiates this process. However, the hydrostatic forces dominate the net exchange of solutes and water. Under normal circumstances, it is believed that 75% of the sodium is reabsorbed back into lymphatic or venous circulation. However, because the kidney is encapsulated, it is sensitive to changes in hydrostatic pressures from both venous and lymphatic congestion. During venous congestion the retention of sodium and water can exceed 85%, further perpetuating the renal congestion. See Verbrugge et al., *The kidney in congestive heart failure: Are natriuresis, sodium, and diruetucs really the good, the bad and the ugly? European Journal of Heart Failure* 2014:16, 133-42 (hereinafter "Verbrugge").

Venous congestion can lead to a prerenal form of acute kidney injury (AKI). Prerenal AKI is due to a loss of perfusion (or loss of blood flow) through the kidney. Many clinicians focus on the lack of flow into the kidney due to shock. However, there is also evidence that a lack of blood flow out of the organ due to venous congestion can be a clinically important sustaining injury. See Damman K, *Importance of venous congestion for worsening renal function in advanced decompensated heart failure, JACC* 17:589-96, 2009 (hereinafter "Damman").

Prerenal AKI occurs across a wide variety of diagnoses requiring critical care admissions. The most prominent admissions are for sepsis and Acute Decompensated Heart Failure (ADHF). Additional admissions include cardiovascular surgery, general surgery, cirrhosis, trauma, burns, and pancreatitis. While there is wide clinical variability in the presentation of these disease states, a common denominator is an elevated central venous pressure. In the case of ADHF, the elevated central venous pressure caused by heart failure leads to pulmonary edema, and, subsequently, dyspnea in turn precipitating the admission. In the case of sepsis, the elevated central venous pressure is largely a result of aggressive fluid resuscitation. Whether the primary insult was low perfusion due to hypovolemia or sodium and fluid retention, the sustaining injury is the venous congestion resulting in inadequate perfusion.

Hypertension is another widely recognized state that creates perturbations within the active and passive transport systems of the kidney(s). Hypertension directly impacts afferent arteriole pressure and results in a proportional increase in net filtration pressure within the glomerulus. The increased filtration fraction also elevates the peritubular capillary pressure, which stimulates sodium and water re-absorption. See Verbrugge.

Because the kidney is an encapsulated organ, it is sensitive to pressure changes in the medullary pyramids. The elevated renal venous pressure creates congestion that leads to a rise in the interstitial pressures. The elevated interstitial pressures exert forces upon both the glomerulus and tubules. See Verburgge. In the glomerulus, the elevated interstitial pressures directly oppose filtration. The increased pressures increase the interstitial fluid, thereby increasing the hydrostatic pressures in the interstitial fluid and peritubular capillaries in the medulla of the kidney. In both instances, hypoxia can ensue leading to cellular injury and further loss of perfusion. The net result is a further exacerbation of the sodium and water re-absorption creating a negative feedback. See Verbrugge, 133-42. Fluid overload, particularly in the abdominal cavity is associated with many diseases and conditions, including elevated intra-abdominal pressure, abdominal compartment syndrome, and acute renal failure. Fluid overload can be addressed through renal replacement therapy. See Peters, C. D., *Short and Long-Term Effects of the Angiotensin II Receptor Blocker Irbesartanon Intradialytic Central Hemodynamics: A Randomized Double-Blind Placebo-Controlled One-Year Intervention Trial* (*the SAFIR Study*), PLoS ONE (2015) 10(6): e0126882. doi:10.1371/journal.pone.0126882 (hereinafter "Peters"). However, such a clinical strategy provides no improvement in renal function for patients with the cardiorenal syndrome. See Bart B, *Ultrafiltration in decompensated heart failure with cardiorenal syndrome, NEJM* 2012; 367:2296-2304 (hereinafter "Bart").

In view of such problematic effects of fluid retention, devices and methods for improving removal of urine from the urinary tract and, specifically for increasing quantity and quality of urine output from the kidneys, are needed.

SUMMARY

In some examples, ureteral catheters are provided comprising: a drainage lumen comprising a proximal portion configured to be positioned in at least a portion of a patient's urethra and a distal portion configured to be positioned in a patient's ureter and/or kidney, the distal portion comprising a coiled retention portion, wherein the retention portion comprises at least a first coil having a first diameter and a second coil having a second diameter, the first diameter being less than the second diameter.

In some examples, a urine collection assembly is provided comprising: at least one ureteral catheter comprising: a drainage lumen comprising a proximal portion configured to be positioned in at least a portion of a patient's urethra and a distal portion configured to be positioned in a patient's ureter and/or kidney, the distal portion comprising a coiled retention portion, wherein the retention portion comprises at least a first coil having a first diameter and a second coil having a second diameter, the first diameter being less than the second diameter; and a bladder catheter for deployment within the patient's bladder, the bladder catheter comprising: a drainage lumen portion defining a drainage lumen and comprising a proximal end, a distal end configured to be positioned in the patient's bladder, and a sidewall extending therebetween; and a deployable anchor portion comprising a seal configured to contact a proximal portion of the bladder wall to essentially or fully seal the urethral opening of the bladder, wherein the drainage lumen portion or the anchor portion comprises at least one drainage port for permitting fluid flow into the drainage lumen.

In some examples, a ureteral catheter is provided comprising: a drainage lumen portion comprising a proximal end, a distal end configured to be positioned in a patient's ureter and/or kidney, and a sidewall extending therebetween; and a retention portion extending radially outwardly from a portion of the distal end of the drainage lumen portion, the retention portion comprising a proximal end having a first diameter, a distal end having a second diameter, and a wall and/or surface extending therebetween, the retention portion being configured to be extended into a deployed position in which the second diameter is greater than the first diameter.

In some examples, a urine collection assembly is provided comprising: at least one ureteral catheter comprising: a drainage lumen portion comprising a proximal end, a distal end configured to be positioned in a patient's ureter and/or kidney, and a sidewall extending therebetween; and a retention portion extending radially outwardly from a portion of the distal end of the drainage lumen portion, the retention portion comprising a proximal end having a first diameter, a distal end having a second diameter, and a wall and/or surface extending therebetween, the retention portion being configured to be extended into a deployed position in which the second diameter is greater than the first diameter; and a bladder catheter for deployment within the patient's bladder, the bladder catheter comprising: a drainage lumen portion defining a drainage lumen and comprising a proximal end, a distal end configured to be positioned in the patient's bladder, and a sidewall extending therebetween; and a deployable anchor portion comprising a seal configured to contact a proximal portion of the bladder wall to seal the urethral opening of the bladder, wherein the drainage lumen portion or the anchor portion comprises at least one drainage port for permitting fluid flow into the drainage lumen.

In some examples, a ureteral catheter is provided comprising: a drainage lumen portion comprising a proximal end, a distal end configured to be positioned in a patient's ureter and/or kidney, and a sidewall extending therebetween, the drainage lumen portion defining a drainage lumen; and a retention portion which, in a deployed position, extends radially outwardly from a portion of the distal end of the drainage lumen portion, the retention portion comprising a plurality of tubes extending between a proximal end of the retention portion and a distal end of the retention portion, wherein each tube defines a lumen in fluid communication with the drainage lumen defined by the drainage lumen portion and wherein each tube comprises a plurality of drainage ports for allowing fluid to enter the lumen.

In some examples, a urine collection assembly is provided comprising: at least one ureteral catheter comprising: a drainage lumen portion comprising a proximal end, a distal end configured to be positioned in a patient's ureter and/or kidney, and a sidewall extending therebetween, the drainage lumen portion defining a drainage lumen; and a retention portion which, in a deployed position, extends radially outward from a portion of the distal end of the drainage lumen portion, the retention portion comprising a plurality of tubes extending between a proximal end of the retention portion and a distal end of the retention portion, wherein each tube defines a lumen in fluid communication with the drainage lumen defined by the drainage lumen portion and wherein each tube comprises a plurality of drainage ports for allowing fluid to enter the lumen; and a bladder catheter for deployment within the patient's bladder, the bladder catheter comprising: a drainage lumen portion defining a drainage lumen and comprising a proximal end, a distal end configured to be positioned in the patient's bladder, and a sidewall extending therebetween; and a deployable anchor portion comprising a seal configured to contact a proximal portion of the bladder wall to seal the urethral opening of the bladder, wherein the drainage lumen portion or the anchor portion comprises at least one drainage port for permitting fluid flow into the drainage lumen.

In some examples, a connector is provided for connecting ureteral catheters configured to be positioned at a patient's ureter and/or kidney to a vacuum source for inducing negative pressure in the ureter and/or kidney and for connecting a bladder catheter to a fluid collection container for fluid collection of urine from the bladder by gravity drainage, the connector comprising: a connector body; first and second ureteral catheter inflow ports extending from the connector body, the inflow ports each being configured to be connected to a ureteral catheter positioned in a patient's ureter and/or kidney; a ureteral catheter outflow port in fluid communication with each inflow port and being configured to be connected to a pump for inducing negative pressure in the respective ureteral catheters; a gravity drainage inflow port configured to be connected to a bladder catheter; and a gravity drainage outflow port in fluid communication with the bladder catheter inflow port and being configured to be connected to a fluid collection container.

In some examples, a urine collection assembly is provided comprising: a first ureteral catheter configured to be positioned in a patient's ureter and/or kidney and a second ureteral catheter configured to be positioned in the patient's other ureter and/or kidney, the ureteral catheters each comprising: a drainage lumen portion defining a drainage lumen and comprising a proximal end, a distal end configured to be positioned in a patient's ureter and/or kidney, and a sidewall extending therebetween; and a retention portion extending radially outward from a portion of the distal end of the drainage lumen portion, and being configured to be extended into a deployed position in which a diameter of the retention portion is greater than a diameter of the drainage lumen portion, wherein at least one of the drainage lumen portion or the retention portion comprises at least one drainage port to permit fluid flow into the drainage lumen; and a bladder catheter for deployment within the patient's bladder, the bladder catheter comprising: a drainage lumen portion defining a drainage lumen and comprising a proximal end, a distal end configured to be positioned in the patient's bladder, and a sidewall extending therebetween; and a deployable anchor portion comprising a seal configured to contact a proximal portion of the bladder wall to seal the urethral opening, wherein at least one of the drainage lumen portion or the anchor portion comprises at least one drainage port for permitting fluid flow into the drainage lumen.

In some examples, a bladder catheter is provided for deployment within the patient's bladder for collecting excess urine not collected by deployed ureteral catheters positioned in the patient's ureter and/or kidney, the bladder catheter comprising: a drainage lumen portion defining a drainage lumen and comprising a proximal end portion, a distal end portion configured to be positioned in the patient's bladder, and a sidewall extending therebetween; and a deployable anchor portion configured to contact a proximal portion of the bladder wall to seal the urethral opening, wherein at least one of the drainage lumen portion or the anchor portion comprises at least one drainage port for permitting fluid flow into the drainage lumen for expelling urine from the bladder.

In some examples, a system is provided for inducing negative pressure in a portion of a urinary tract of a patient, the system comprising: a ureteral catheter comprising: a drainage lumen portion comprising a proximal end, a distal end configured to be positioned in a patient's ureter and/or kidney, and a sidewall extending therebetween; and a retention portion extending radially outward from a portion of the distal end of the drainage lumen portion, and being configured to be extended into a deployed position in which a diameter of the retention portion is greater than a diameter of the drainage lumen portion, wherein at least one of the drainage lumen portion or the retention portion comprises at least one drainage port to permit fluid flow into the drainage lumen; and a pump in fluid communication with a drainage lumen defined by the drainage lumen portion of the ureteral catheter, the pump being configured for inducing a negative pressure in a portion of the urinary tract of the patient to draw fluid through the drainage lumen of the ureteral catheter.

Methods of using the above catheters and assemblies also are provided.

In some examples, a method is provided for extracting urine from a ureter and/or kidney of a patient for effecting interstitial pressure in the kidney, the method comprising: positioning a distal end of a catheter at a fluid collection position within a patient's ureter and/or kidney, the catheter comprising a tube defining a drainage lumen and comprising a helical retention portion and a plurality of drainage ports; inducing a negative pressure within a drainage lumen of the catheter; and extracting urine by drawing urine through the drainage ports into the drainage lumen, thereby altering interstitial pressure within the patient's kidney.

In some examples, a method is provided for inhibiting kidney damage by application of negative pressure to decrease interstitial pressure within tubules of the medullar region to facilitate urine output and to prevent venous congestion-induced nephron hypoxia in the medulla of the kidney, the method comprising: deploying a ureteral catheter in the ureter and/or kidney of a patient such that flow of urine from the ureter and/or kidney is not prevented by occlusion of the ureter and/or kidney by the deployed catheter; and applying negative pressure to the ureter and/or kidney through the catheter for a predetermined period of time to facilitate urine output from the kidney.

In some examples, a method is provided for treatment of acute kidney injury due to venous congestion, the method comprising: deploying a ureteral catheter at a fluid collection position in the ureter and/or kidney of a patient such that the ureter and/or kidney is not occluded by the deployed catheter; and applying negative pressure to the ureter and/or kidney through the catheter for a predetermined period of time, thereby reducing venous congestion in the kidney to treat acute kidney injury.

In some examples, a method is provided for treatment of New York Heart Association (NYHA) Class III and/or Class IV heart failure through reduction of venous congestion in the kidney(s), the method comprising: deploying a ureteral catheter in the ureter and/or kidney of a patient such that flow of urine from the ureter and/or kidney is not prevented by occlusion of the ureter and/or kidney; and applying negative pressure to the ureter and/or kidney through the catheter for a predetermined period of time to treat volume overload in NYHA Class III and/or Class IV heart failure.

In some examples, a method is provided for treatment of Stage 4 and/or Stage 5 chronic kidney disease through reduction of venous congestion in the kidney(s), the method comprising: deploying a ureteral catheter in the ureter and/or kidney of a patient such that flow of urine from the ureter and/or kidney is not prevented by occlusion of the ureter and/or kidney; and applying negative pressure to the ureter and/or kidney through the catheter for a predetermined period of time to treat Stage 4 and/or Stage 5 chronic kidney disease.

Non-limiting examples, aspects or embodiments of the present invention will now be described in the following numbered clauses:

Clause 1: A ureteral catheter comprising: a drainage lumen comprising a proximal portion configured to be positioned in at least a portion of a patient's urethra and a distal portion configured to be positioned in a patient's ureter and/or kidney, the distal portion comprising a coiled retention portion, wherein the retention portion comprises at least a first coil having a first diameter and a second coil having a second diameter, the first diameter being less than the second diameter.

Clause 2: The ureteral catheter of clause 1, wherein the first coil is proximal to the second coil.

Clause 3: The ureteral catheter of any of clause 1 or clause 2, wherein, prior to insertion into a patient's urinary tract, a portion of the drainage lumen that is proximal to the retention portion defines a straight or curvilinear central axis, and wherein the first coil and the second coil of the retention portion extend about an axis that is at least partially coextensive with the straight or curvilinear central axis of the portion of the drainage lumen.

Clause 4: The ureteral catheter of clause 1 or clause 2, wherein, prior to insertion to the patient's urinary tract, a portion of the drainage lumen that is proximal to the retention portion defines a straight or curvilinear central axis, and wherein the first coil and the second coil of the retention portion extend about an axis that is essentially coextensive with the straight or curvilinear central axis of the portion of the drainage lumen.

Clause 5: The ureteral catheter of clause 3 or clause 4, wherein the axis of the retention portion is curved relative to the central axis of the drainage lumen.

Clause 6: The ureteral catheter of any of clauses 1 to 5, wherein a portion of the drainage lumen that is proximal to the retention portion defines a straight or curvilinear central axis, and wherein the first coil and the second coil of the retention portion extend about an axis of the retention portion, the axis of the retention portion being positioned at an angle from the central axis ranging from about 15 degrees to about 75 degrees.

Clause 7: The ureteral catheter of any of clauses 1 to 6, wherein the catheter is transitionable between a contracted configuration for insertion into the patient's ureter and a deployed configuration for deployment within the ureter.

Clause 8: The ureteral catheter of any of clauses 1 to 7, wherein the retention portion further comprises a third coil, the third coil having a diameter greater than or equal to either the first diameter or the second diameter.

Clause 9: The ureteral catheter of any of clauses 1 to 8, wherein the retention portion comprises a tube comprising perforations for permitting fluid to be received within the lumen of the tube.

Clause 10: The ureteral catheter of clause 9, wherein, in the retention portion, the tube comprises a radially inwardly facing side and a radially outwardly facing side, and wherein a total surface area for perforations on the radially inwardly facing side is greater than a total surface area of perforations on the radially outwardly facing side.

Clause 11: The ureteral catheter of clause 9, wherein, in the retention portion, the tube comprises a radially inwardly facing side and a radially outwardly facing side, and wherein the perforations are disposed on the radially inwardly facing side, and wherein the radially outwardly facing side of the tube is essentially free of perforations.

Clause 12: The ureteral catheter of clause 11, wherein the radially outwardly facing side of the tube is free of perforations.

Clause 13: The ureteral catheter of any of clauses 1 to 12, wherein the tube is formed, at least in part, from one or more of copper, silver, gold, nickel-titanium alloy, stainless steel, titanium, polyurethane, polyvinyl chloride, polytetrafluoroethylene (PTFE), latex, and silicone.

Clause 14: A urine collection assembly comprising: at least one ureteral catheter comprising: a drainage lumen comprising a proximal portion configured to be positioned in at least a portion of a patient's urethra and a distal portion configured to be positioned in a patient's ureter and/or kidney, the distal portion comprising a coiled retention portion, wherein the retention portion comprises at least a first coil having a first diameter and a second coil having a second diameter, the first diameter being less than the second diameter; and a bladder catheter for deployment within the patient's bladder, the bladder catheter comprising: a drainage lumen portion defining a drainage lumen and comprising a proximal end, a distal end configured to be positioned in the patient's bladder, and a sidewall extending therebetween; and a deployable anchor portion comprising a seal configured to contact a proximal portion of the bladder wall to essentially or fully seal the urethral opening of the bladder, wherein the drainage lumen portion or the anchor portion comprises at least one drainage port for permitting fluid flow into the drainage lumen.

Clause 15: The assembly of clause 14, wherein the drainage lumen portion of the at least one ureteral catheter is removably received through the drainage port of the bladder catheter, such that the proximal end of the at least one ureteral catheter is disposed within the drainage lumen of the bladder catheter.

Clause 16: The assembly of any of clauses 14 or 15, wherein the deployable anchor portion of the bladder catheter comprises an inflatable element or balloon in fluid communication with an inflation lumen defined by the drainage lumen portion of the bladder catheter.

Clause 17: The assembly of any of clauses 14 to 16, wherein the at least one drainage port is disposed on a sidewall of the bladder catheter at a position proximal to the deployable anchor portion.

Clause 18: The assembly of any of clauses 14 to 17, wherein the deployable anchor portion comprises an expandable cage comprising a plurality of flexible members extending radially and longitudinally from the drainage lumen portion of the bladder catheter.

Clause 19: The assembly of any of clauses 14 to 18, wherein the deployable anchor portion comprises a plurality of longitudinally extending members that, in a deployed position, extend radially and longitudinally outwardly from a portion of the distal end of the bladder catheter, thereby forming a cage.

Clause 20: The assembly of clause 18, wherein the deployable anchor further comprises a flexible cover extending about an upper portion of the cage.

Clause 21: The assembly of clause 20, wherein the cover extends over at least about the upper half, or at about least the upper ⅔, of the cage.

Clause 22: The assembly of any of clauses 14 to 21, wherein the drainage lumen of the at least one ureteral catheter is separate from the drainage lumen of the bladder along an entire length of the catheters.

Clause 23: A ureteral catheter comprising: a drainage lumen portion comprising a proximal end, a distal end configured to be positioned in a patient's ureter and/or kidney, and a sidewall extending therebetween; and a retention portion extending radially outwardly from a portion of the distal end of the drainage lumen portion, the retention portion comprising a proximal end having a first diameter, a distal end having a second diameter, and a wall and/or surface extending therebetween, the retention portion being configured to be extended into a deployed position in which the second diameter is greater than the first diameter.

Clause 24: The ureteral catheter of clause 23, wherein the retention portion comprises an expandable element or balloon in fluid communication with an inflation lumen extending along the drainage lumen portion.

Clause 25: The ureteral catheter of clause 23 or clause 24, wherein the retention portion comprises a coiled tube extending from the distal end of the drainage lumen portion, the tube defining a lumen in fluid communication with the drainage lumen defined by the drainage lumen portion.

Clause 26: The ureteral catheter of any of clauses 23 to 25, wherein the coiled tube comprises perforations extending through a sidewall of the tube for permitting fluid to be received within the lumen.

Clause 27: The ureteral catheter of clause 26, wherein the perforations are disposed on a radially inwardly facing portion of the tube, and wherein an opposing radially outwardly facing portion of the tube is essentially free of perforations.

Clause 28: The ureteral catheter of clause 27, wherein the opposing radially outwardly facing portion of the tube is free of perforations.

Clause 29: The ureteral catheter of any of clauses 23 to 28, wherein the drainage lumen portion and the retention portion are formed, at least in part, from one or more of copper, silver, gold, nickel-titanium alloy, stainless steel, titanium, polyurethane, polyvinyl chloride, polytetrafluoroethylene (PTFE), latex, and silicone.

Clause 30: The ureteral catheter of clause 23, wherein the retention portion comprises a wedge or funnel-shaped extension formed from a compressible and/or porous material.

Clause 31: The ureteral catheter of any of clauses 23 to 30, wherein the retention portion is integrally formed with the drainage lumen portion.

Clause 32: The ureteral catheter of any of clauses 23 to 31, wherein the retention portion further comprises a tapered inner surface configured to direct fluid towards the drainage lumen defined by the drainage lumen portion.

Clause 33: The ureteral catheter of any of clauses 23 to 32, wherein the drainage lumen of the catheter is configured to be pressurized to a negative pressure for fluid collection from the ureter and/or kidney.

Clause 34: A urine collection assembly comprising: at least one ureteral catheter comprising: a drainage lumen portion comprising a proximal end, a distal end configured to be positioned in a patient's ureter and/or kidney, and a sidewall extending therebetween; and a retention portion extending radially outwardly from a portion of the distal end of the drainage lumen portion, the retention portion comprising a proximal end having a first diameter, a distal end having a second diameter, and a wall and/or surface extending therebetween, the retention portion being configured to be extended into a deployed position in which the second diameter is greater than the first diameter; and a bladder catheter for deployment within the patient's bladder, the bladder catheter comprising: a drainage lumen portion defining a drainage lumen and comprising a proximal end, a distal end configured to be positioned in the patient's bladder, and a sidewall extending therebetween; and a deployable anchor portion comprising a seal configured to contact a proximal portion of the bladder wall to seal the urethral opening of the bladder, wherein the drainage lumen portion or the anchor portion comprises at least one drainage port for permitting fluid flow into the drainage lumen.

Clause 35: The assembly of clause 34, wherein the drainage lumen portion of the at least one ureteral catheter is removably received through the drainage port of the bladder catheter, such that the proximal end of the at least one ureteral catheter is disposed within the drainage lumen of the bladder catheter.

Clause 36: The assembly of clause 34 or clause 35, wherein the deployable anchor portion of the bladder catheter comprises an inflatable element or balloon in fluid communication with an inflation lumen defined by the drainage lumen portion of the bladder catheter.

Clause 37: The assembly of any of clauses 34 to 36, wherein the at least one drainage port is disposed on a sidewall of the bladder catheter at a position proximal to the deployable anchor portion.

Clause 38: The assembly of clause 34, wherein the deployable anchor portion comprises an expandable cage comprising a plurality of flexible members extending radially and longitudinally from the drainage lumen portion of the bladder catheter.

Clause 39: The assembly of clause 34, wherein the deployable anchor portion comprises a plurality of longitudinally extending members that, in a deployed position, extend radially and longitudinally outward from a portion of the distal end of the bladder catheter, thereby forming a cage.

Clause 40: The assembly of clause 38 or clause 39, wherein the deployable anchor further comprises a flexible cover extending about an upper portion of the cage.

Clause 41: The assembly of clause 40, wherein the cover extends over at least about the upper half, or at least about the upper ⅔, of the cage.

Clause 42: A ureteral catheter comprising: a drainage lumen portion comprising a proximal end, a distal end configured to be positioned in a patient's ureter and/or kidney, and a sidewall extending therebetween, the drainage lumen portion defining a drainage lumen; and a retention portion which, in a deployed position, extends radially outwardly from a portion of the distal end of the drainage lumen portion, the retention portion comprising a plurality of tubes extending between a proximal end of the retention portion and a distal end of the retention portion, wherein each tube defines a lumen in fluid communication with the drainage lumen defined by the drainage lumen portion and wherein each tube comprises a plurality of drainage ports for allowing fluid to enter the lumen.

Clause 43: The ureteral catheter of clause 42, wherein each tube comprises a radially inwardly facing side and a radially outwardly facing side, and wherein the drainage ports are disposed on the radially inwardly facing side of each tube.

Clause 44: The ureteral catheter of clause 43, wherein the radially outwardly facing side of each tube is essentially free of drainage ports.

Clause 45: The ureteral catheter of clause 43, wherein the radially outwardly facing side of each tube is free of drainage ports.

Clause 46: The ureteral catheter of any of clauses 42 to 45, wherein the retention portion is transitionable from a contracted position, in which each of the plurality of tubes is substantially parallel to a longitudinal axis of the drainage lumen portion and the deployed position in which portions of the tubes extend radially outwardly from the drainage lumen portion.

Clause 47: The ureteral catheter of any of clauses 42 to 46, wherein in the deployed position the tubes define a spherical or ellipsoidal cavity, and wherein the drainage lumen portion extends at least partially into the cavity.

Clause 48: The ureteral catheter of any of clauses 42 to 47, wherein the drainage lumen portion and the retention portion are formed, at least in part, from one or more of copper, silver, gold, nickel-titanium alloy, stainless steel, titanium, polyurethane, polyvinyl chloride, polytetrafluoroethylene (PTFE), latex, and silicone.

Clause 49: The ureteral catheter of any of clauses 42 to 48, wherein the retention portion is integrally formed with the drainage lumen portion.

Clause 50: The ureteral catheter of any of clauses 42 to 49, wherein the drainage lumen of the catheter is configured to be pressurized to a negative pressure for fluid collection from the ureter and/or kidney.

Clause 51: A urine collection assembly comprising: at least one ureteral catheter comprising: a drainage lumen portion comprising a proximal end, a distal end configured to be positioned in a patient's ureter and/or kidney, and a sidewall extending therebetween, the drainage lumen portion defining a drainage lumen; and a retention portion which, in a deployed position, extends radially outward from a portion of the distal end of the drainage lumen portion, the retention portion comprising a plurality of tubes extending between a proximal end of the retention portion and a distal end of the retention portion, wherein each tube defines a lumen in fluid communication with the drainage lumen defined by the drainage lumen portion and wherein each tube comprises a plurality of drainage ports for allowing fluid to enter the lumen; and a bladder catheter for deployment within the patient's bladder, the bladder catheter comprising: a drainage lumen portion defining a drainage lumen and comprising a proximal end, a distal end configured to be positioned in the patient's bladder, and a sidewall extending therebetween; and a deployable anchor portion comprising a seal configured to contact a proximal portion of the bladder wall to seal the urethral opening of the bladder, wherein the drainage lumen portion or the anchor portion comprises at least one drainage port for permitting fluid flow into the drainage lumen.

Clause 52: The assembly of clause 51, wherein the drainage lumen portion of the at least one ureteral catheter is removably received through the drainage port of the bladder catheter, such that the proximal end of the at least one ureteral catheter is disposed within the drainage lumen of the bladder catheter.

Clause 53: The assembly of clause 51 or clause 52, wherein the deployable anchor portion of the bladder catheter comprises an inflatable element or balloon in fluid communication with an inflation lumen defined by the drainage lumen portion of the bladder catheter.

Clause 54: The assembly of any of clauses 51 to 53, wherein the at least one drainage port is disposed on a sidewall of the bladder catheter at a position proximal to the deployable anchor portion.

Clause 55: The assembly of clause 51 or clause 52, wherein the deployable anchor portion comprises an expandable cage comprising a plurality of flexible members extending radially and longitudinally from the drainage lumen portion of the bladder catheter.

Clause 56: The assembly of clause 51 or clause 52, wherein the deployable anchor portion comprises a plurality of longitudinally extending members that, in a deployed position, extend radially and longitudinally outward from a portion of the distal end of the bladder catheter, thereby forming a cage.

Clause 57: The assembly of clause 55 or clause 56, wherein the deployable anchor further comprises a flexible cover extending about an upper portion of the cage.

Clause 58: The assembly of clause 57, wherein the cover extends over at least about the upper half, or about the upper ⅔, of the cage.

Clause 59: A connector for connecting ureteral catheters configured to be positioned at a patient's ureter and/or kidney to a vacuum source for inducing negative pressure in the ureter and/or kidney and for connecting a bladder catheter to a fluid collection container for fluid collection of urine from the bladder by gravity drainage, the connector comprising: a connector body; first and second ureteral catheter inflow ports extending from the connector body, the inflow ports each being configured to be connected to a ureteral catheter positioned in a patient's ureter and/or kidney; a ureteral catheter outflow port in fluid communication with each inflow port and being configured to be connected to a pump for inducing negative pressure in the respective ureteral catheters; a gravity drainage inflow port configured to be connected to the bladder catheter; and a gravity drainage outflow port in fluid communication with the bladder catheter inflow port and being configured to be connected to a fluid collection container.

Clause 60: The connector of clause 59, wherein the connector body defines a fluid conduit extending from the at least two ureteral catheter inflow ports to the single ureteral catheter outflow port.

Clause 61: The connector of clause 59 or clause 60, wherein the inflow ports are configured to removably receive ends of the respective catheters.

Clause 62: The connector of any of clauses 59 to 61, wherein the vacuum outflow port and the gravity drainage outflow port are positioned for connection to a single socket for establishing fluid connection with the pump and fluid connection container.

Clause 63: A urine collection assembly comprising: a first ureteral catheter configured to be positioned in a patient's ureter and/or kidney and a second ureteral catheter configured to be positioned in the patient's other ureter and/or kidney, the ureteral catheters each comprising: a drainage lumen portion defining a drainage lumen and comprising a proximal end, a distal end configured to be positioned in a patient's ureter and/or kidney, and a sidewall extending therebetween; and a retention portion extending radially outward from a portion of the distal end of the drainage lumen portion, and being configured to be extended into a deployed position in which a diameter of the retention portion is greater than a diameter of the drainage lumen portion, wherein at least one of the drainage lumen portion or the retention portion comprises at least one drainage port to permit fluid flow into the drainage lumen; and a bladder catheter for deployment within the patient's bladder, the bladder catheter comprising: a drainage lumen portion defining a drainage lumen and comprising a proximal end, a distal end configured to be positioned in the patient's bladder, and a sidewall extending therebetween; and a deployable anchor portion comprising a seal configured to contact a proximal portion of the bladder wall to seal the urethral opening, wherein at least one of the drainage lumen portion or the anchor portion comprises at least one drainage port for permitting fluid flow into the drainage lumen.

Clause 64: The assembly of clause 63, further comprising a connector for connecting proximal ends of the ureteral catheters to a vacuum source and for connecting the proximal end of the bladder catheter to a fluid collection container for fluid collection by gravity drainage.

Clause 65: The assembly of clause 64, wherein the connector comprises: at least two ureteral catheter inflow ports for connection to the respective proximal ends of the first ureteral catheter and the second ureteral catheter; a ureteral catheter outflow port in fluid communication with each inflow port and being configured to be connected to a pump for inducing negative pressure in the respective ureteral catheters; a gravity drainage inflow port configured to be connected to the proximal end of the bladder catheter; and an outflow port in fluid communication with the bladder catheter inflow port and being configured to be connected to a fluid collection container.

Clause 66: The assembly of clause 65, wherein the connector further comprises conduit extending from the at least two ureteral catheter inflow ports to the single ureteral catheter outflow port.

Clause 67: The assembly of clause 65 or clause 66, wherein the proximal ends of the respective catheters are removably connected to their respective inflow ports.

Clause 68: The assembly of any clauses 63 to 67, wherein the deployable anchor portion of the bladder catheter comprises an inflatable element or balloon in fluid communication with an inflation lumen defined by the drainage lumen portion of the bladder catheter.

Clause 69: The assembly of clause 63, wherein the deployable anchor portion comprises an expandable cage comprising a plurality of flexible members extending radially and longitudinally from the drainage lumen portion of the bladder catheter and a cover enclosing at least a portion of the cage.

Clause 70: The assembly of clause 68 or clause 69, wherein the deployable anchor further comprises a flexible cover extending about an upper portion of the cage.

Clause 71: The assembly of clause 70, wherein the cover extends over at least about the upper half, or at least about the upper ⅔, of the cage.

Clause 72: A bladder catheter for deployment within the patient's bladder for collecting excess urine not collected by deployed ureteral catheters positioned in the patient's ureter and/or kidney, the bladder catheter comprising: a drainage lumen portion defining a drainage lumen and comprising a proximal end portion, a distal end portion configured to be positioned in the patient's bladder, and a sidewall extending therebetween; and a deployable anchor portion configured to contact a proximal portion of the bladder wall to seal the urethral opening, wherein at least one of the drainage lumen portion or the anchor portion comprises at least one drainage port for permitting fluid flow into the drainage lumen for expelling urine from the bladder.

Clause 73: The bladder catheter of clause 72, wherein the deployable anchor portion comprises an inflatable element or balloon in fluid communication with an inflation lumen defined by the drainage lumen portion of the bladder catheter.

Clause 74: The bladder catheter of clause 73, wherein the inflatable element or balloon comprises an upper portion configured to be positioned in the patient's bladder and a lower portion configured to be positioned in the patient's urethra.

Clause 75: The bladder catheter of any of clauses 62 to 74, wherein the at least one drainage port is disposed on a sidewall of the bladder catheter at a position proximal to the anchor portion.

Clause 76: The bladder catheter of clause 72, wherein the deployable anchor portion comprises an expandable cage comprising a plurality of flexible members extending radially and longitudinally from the drainage lumen portion of the bladder catheter and a cover enclosing at least a portion of the cage.

Clause 77: The bladder catheter of clause 76, wherein the deployable anchor portion further comprises a flexible cover extending about an upper portion of the cage.

Clause 78: The bladder catheter of clause 77, wherein the cover extends over at least about the upper half, or at least about the upper ⅔, of the cage.

Clause 79: A system for inducing negative pressure in a portion of a urinary tract of a patient, the system comprising: a ureteral catheter comprising: a drainage lumen portion comprising a proximal end, a distal end configured to be positioned in a patient's ureter and/or kidney, and a sidewall extending therebetween; and a retention portion extending radially outward from a portion of the distal end of the drainage lumen portion, and being configured to be extended into a deployed position in which a diameter of the retention portion is greater than a diameter of the drainage lumen portion, wherein at least one of the drainage lumen portion or the retention portion comprises at least one drainage port to permit fluid flow into the drainage lumen; and a pump in fluid communication with a drainage lumen defined by the drainage lumen portion of the ureteral catheter, the pump being configured for inducing a negative pressure in a portion of the urinary tract of the patient to draw fluid through the drainage lumen of the ureteral catheter.

Clause 80: The system of clause 79, further comprising: a bladder catheter for deployment within the patient's bladder, the bladder catheter comprising: a drainage lumen portion defining a drainage lumen and comprising a proximal end, a distal end configured to be positioned in the patient's bladder, and a sidewall extending therebetween; and a deployable anchor portion comprising a seal configured to contact a proximal portion of the bladder wall to seal the urethral opening, wherein at least one of the drainage lumen portion or the anchor portion comprises at least one drainage port for permitting fluid flow into the drainage lumen for expelling urine from the bladder.

Clause 81: The system of clause 80, further comprising an external fluid collection container in fluid communication with the drainage lumen of the bladder catheter for gravity drainage of fluid through the bladder catheter.

Clause 82: The system of any of clauses 79 to 81, further comprising one or more sensors in fluid communication with the drainage lumen, the one or more sensors being configured to determine information comprising at least one of capacitance, analyte concentration, and temperature of urine within the respective drainage lumen; and a processor comprising computer readable memory including programming instructions that, when executed, cause the processor to: receive the information from the one or more sensors and adjust an operating parameter of the pump based, at least in part, on the information received from the one or more sensors to increase or decrease vacuum pressure in the drainage lumen of the at least one ureteral catheter to adjust flow of urine through the drainage lumen.

Clause 83: The system of clause 82, further comprising a data transmitter in communication with the processor, the data transmitter being configured to provide the information from the one or more sensors to an external source.

Clause 84: The system of any of clauses 80 to 83, wherein the pump provides a sensitivity of 10 mmHg or less.

Clause 85: The system of any of clauses 80 to 84, wherein the pump is capable of continuous operation for a time period ranging from about 8 to about 24 hours per day.

Clause 86: They system of any of clauses 80 to 85, wherein the pump is configured to provide intermittent negative pressure.

Clause 87: The system of any of clauses 80 to 86, wherein the pump is configured to apply negative pressure independently to each catheter such that the pressure in each catheter can be the same or different from the other catheter(s).

Clause 88: The system of any of clauses 80 to 86, wherein the pump is configured to alternate between providing negative pressure and providing positive pressure.

Clause 89: The system of any of clauses 80 to 86, wherein the pump is configured to alternate between providing negative pressure and equalizing pressure to atmosphere.

Clause 90: The system of clause 88, wherein the negative pressure is provided within a range of 5 mmHg to 50 mmHg, and/or wherein the positive pressure is provided within a range of 5 mmHg to 20 mmHg.

Clause 91: The system of any of clauses 80 to 90, wherein the pump is configured to alternate between two or more different pressure levels.

Clause 92: The system of clause 91, wherein the pump is configured to adjust the pressure levels at a regular or irregular frequency based, at least in part, on a predetermined algorithm.

Clause 93: The system of clause 92, wherein the predetermined algorithm is based in part on demographic data and/or patient-specific variables.

Clause 94: The system of clause 93, wherein the demographic data and/or patient-specific variables comprise one or more of anatomical, genetic, physiological, and pathophysiological factors.

Clause 95: The system of clause 92, wherein the predetermined algorithm is based, in part, on continuously or non-continuously changing patient values, the patient values comprising one or more of urine output rate, peristaltic activity of renal and/or urological system, heart rate, cardiac output, blood pressure, respiration rate, renal blood flow, renal plasma flow, and biomarkers.

Clause 96: A method for extracting urine from a ureter and/or kidney of a patient for effecting interstitial pressure in the kidney, the method comprising: positioning a distal end of a catheter at a fluid collection position within a patient's ureter and/or kidney, the catheter comprising a tube defining a drainage lumen and comprising a helical retention portion and a plurality of drainage ports; inducing a negative pressure within a drainage lumen of the catheter; and extracting urine by drawing urine through the drainage ports into the drainage lumen, thereby altering interstitial pressure within the patient's kidney.

Clause 97: The method of clause 96, wherein positioning the catheter comprises deploying the catheter by expanding the helical retention portion at the fluid collection position.

Clause 98: The method of clause 96 or clause 97, further comprising positioning a distal end of the bladder catheter in the patient's bladder and deploying an anchor within the bladder, such that the anchor essentially or fully seals the urethral sphincter of the bladder.

Clause 99: The method of clause 98, wherein positioning the bladder catheter in the bladder comprises advancing the bladder catheter over a guidewire used for positioning of the ureteral catheter.

Clause 100: A method of inhibiting kidney damage by application of negative pressure to decrease interstitial pressure within tubules of the medullar region to facilitate urine output and to prevent venous congestion-induced nephron hypoxia in the medulla of the kidney, the method comprising: deploying a ureteral catheter in the ureter and/or kidney of a patient such that flow of urine from the ureter and/or kidney is not prevented by occlusion of the ureter and/or kidney by the deployed catheter; and applying negative pressure to the ureter and/or kidney through the catheter for a period of time sufficient to facilitate urine output from the kidney.

Clause 101: The method of clause 100, further comprising positioning a bladder catheter in the patient's bladder, such that an anchor of the bladder catheter essentially or fully seals the urethral sphincter of the bladder.

Clause 102: The method of clause 101, further comprising causing drainage of urine from the bladder through the bladder catheter for a period of time.

Clause 103: The method of clause 100, wherein deploying the catheter comprises accessing the ureter and/or kidney through an incision or orifice other than the urethral orifice.

Clause 104: A method for treatment of acute kidney injury due to venous congestion, the method comprising: deploying a ureteral catheter in the ureter and/or kidney of a patient such that flow of urine from the ureter and/or kidney is not prevented by occlusion of the ureter and/or kidney; and applying negative pressure to the ureter and/or kidney through the catheter for a period of time sufficient to treat acute kidney injury due to venous congestion.

Clause 105: A method for treatment of NYHA Class III and/or Class IV heart failure through reduction of venous congestion in the kidney(s), the method comprising: deploying a ureteral catheter in the ureter and/or kidney of a patient such that flow of urine from the ureter and/or kidney is not prevented by occlusion of the ureter and/or kidney; and applying negative pressure to the ureter and/or kidney through the catheter for a period of time sufficient to treat NYHA Class III and/or Class IV heart failure.

Clause 106: A method for treatment of NYHA Class II, Class III, and/or Class IV heart failure through reduction of venous congestion in the kidney(s), the method comprising: deploying a catheter in a bladder of a patient such that flow of urine into the bladder from a ureter and/or kidney is not prevented by occlusion; and applying negative pressure to the bladder through the catheter for a period of time sufficient to treat NYHA Class II, Class III, and/or Class IV heart failure.

Clause 107: A method for treatment of Stage 4 and/or Stage 5 chronic kidney disease through reduction of venous congestion in the kidney(s), the method comprising: deploying a ureteral catheter in a ureter and/or kidney of a patient such that flow of urine from the ureter and/or kidney is not prevented by occlusion of the ureter and/or kidney; and applying negative pressure to the ureter and/or kidney through the catheter for a period of time sufficient to treat Stage 4 and/or Stage 5 chronic kidney disease.

Clause 108: A method for treatment of Stage 3, Stage 4, and/or Stage 5 chronic kidney disease through reduction of venous congestion in the kidney(s), the method comprising: deploying a catheter in a bladder of a patient such that flow of urine from a ureter and/or kidney is not prevented by occlusion; and applying negative pressure to the bladder through the catheter for a period of time sufficient to treat Stage 3, Stage 4, and/or Stage 5 chronic kidney disease.

Clause 109: A ureteral catheter, comprising: a drainage lumen comprising a proximal portion configured to be positioned in at least a portion of a patient's urethra and a distal portion configured to be positioned in a patient's ureter and/or kidney, the distal portion comprising a coiled retention portion, the coiled retention portion comprising: at least a first coil having a first diameter; at least a second coil having a second diameter, the first diameter being less than the second diameter; and one or more perforations on a sidewall of the drainage lumen for permitting fluid flow into the drainage lumen, wherein, prior to insertion into a patient's urinary tract, a portion of the drainage lumen that is proximal to the retention portion defines a straight or curvilinear central axis, and wherein, when deployed, the first coil and the second coil of the retention portion extend about an axis of the retention portion that is at least partially coextensive with the straight or curvilinear central axis of the portion of the drainage lumen.

Clause 110: The ureteral catheter of clause 109, wherein the axis of the retention portion is curved relative to the central axis of the drainage lumen.

Clause 111: The ureteral catheter of clause 109 or clause 110, wherein at least a portion of the axis of the retention portion extends at an angle from the central axis ranging from about 15 degrees to about 75 degrees.

Clauses 112: The ureteral catheter of any of clauses 109 to 111, wherein the catheter is transitionable between a contracted configuration for insertion into the patient's ureter and a deployed configuration for deployment within the ureter.

Clause 113: The ureteral catheter of any of clauses 109 to 112, wherein the retention portion further comprises a third coil extending about the axis of the retention portion, the third coil having a diameter greater than or equal to either the first diameter or the second diameter.

Clause 114: The ureteral catheter of any of clauses 109 to 113, wherein, the retention portion of the drainage lumen comprises a sidewall comprising a radially inwardly facing side and a radially outwardly facing side, and wherein a total surface area of perforations on the radially inwardly facing side is greater than a total surface area of perforations on the radially outwardly facing side.

Clause 115: The ureteral catheter of any of clauses 109 to 114, wherein, the retention portion of the drainage lumen comprises a sidewall comprising a radially inwardly facing side and a radially outwardly facing side, and wherein the one or more perforations are disposed on the radially inwardly facing side, and wherein the radially outwardly facing side is essentially free of perforations.

Cause 116: The ureteral catheter of clause any of clauses 109 to 116, wherein the drainage lumen is formed, at least in part, from one or more of copper, silver, gold, nickel-titanium alloy, stainless steel, titanium, polyurethane, polyvinyl chloride, polytetrafluoroethylene (PTFE), latex, and silicone.

Clause 117: The ureteral catheter of any of clauses 109 to 116, wherein the retention portion of the drainage lumen further comprises an open distal end for permitting fluid flow into the drainage lumen.

Clause 118: The ureteral catheter of any of clauses 109 to 117, wherein each of the one or more perforations has a diameter of about 0.7 to 0.9 mm.

Clause 119: The ureteral catheter of any of clauses 109 to 118, wherein the first diameter is about 8 mm to 10 mm and the second dimeter is about 16 mm to 20 mm.

Clause 120: A system for inducing negative pressure in a portion of a urinary tract of a patient, the system comprising: at least one urine collection catheter comprising a drainage lumen comprising a proximal portion configured to be positioned in at least a portion of a patient's urethra and a distal portion configured to be positioned in a patient's ureter and/or kidney, the distal portion comprising a coiled retention portion, the coiled retention portion comprising: at least a first coil having a first diameter; at least a second coil having a second diameter, the first diameter being less than the second diameter; and one or more perforations on a sidewall of the drainage lumen for permitting fluid flow into the drainage lumen, wherein, prior to insertion into a patient's urinary tract, a portion of the drainage lumen that is proximal to the retention portion defines a straight or curvilinear central axis, and wherein, when deployed, the first coil and the second coil of the retention portion extend about an axis of the retention portion that is at least partially coextensive with the straight or curvilinear central axis of the portion of the drainage lumen; and a pump in fluid communication with the drainage lumen of the at least one ureteral catheter, the pump being configured for inducing a negative pressure in a portion of the urinary tract of the patient to draw fluid through the drainage lumen of the ureteral catheter.

Clause 121: The system of clause 120, further comprising: one or more sensors in fluid communication with the drainage lumen, the one or more sensors being configured to determine information comprising at least one of capacitance, analyte concentration, and temperature of urine within the respective drainage lumen; and a controller comprising computer readable memory including programming instructions that, when executed, cause the controller to: receive the information from the one or more sensors and adjust an operating parameter of the pump based, at least in part, on the information received from the one or more sensors to increase or decrease vacuum pressure in the drainage lumen of the at least one ureteral catheter to adjust flow of urine through the drainage lumen.

Clause 122: The system of clause 120 or clause 121, further comprising a data transmitter in communication with the controller, the data transmitter being configured to provide the information from the one or more sensors to an external source.

Clause 123: The system of any of clauses 120 to 122, wherein the pump provides a sensitivity of 10 mmHg or less.

Clause 124: The system of any of clauses 120 to 122, wherein the pump is configured to alternate between providing negative pressure and providing positive pressure.

Clause 125: The system of clause 124, wherein the negative pressure is provided within a range of 5 mmHg to 50 mmHg, and wherein the positive pressure is provided within a range of 5 mmHg to 20 mmHg.

Clause 126: A method of inhibiting kidney damage by application of negative pressure to decrease interstitial pressure within tubules of the medullar region to facilitate urine output and to prevent venous congestion-induced nephron hypoxia in the medulla of the kidney, the method comprising: deploying a ureteral catheter in the ureter and/or kidney of a patient such that flow of urine from the ureter and/or kidney is not prevented by occlusion of the ureter and/or kidney by the deployed catheter; and applying negative pressure to the ureter and/or kidney through the catheter for a period of time sufficient to facilitate urine output from the kidney, wherein the ureteral catheter comprises a drainage lumen comprising a proximal portion configured to be positioned in at least a portion of a patient's urethra and a distal portion configured to be positioned in a patient's ureter and/or kidney, the distal portion comprising a coiled retention portion, the coiled retention portion comprising: at least a first coil having a first diameter; at least a second coil having a second diameter, the first diameter being less than the second diameter; and one or more perforations on a sidewall of the drainage lumen for permitting fluid flow into the drainage lumen, wherein, prior to deployment, a portion of the drainage lumen that is proximal to the retention portion defines a straight or curvilinear central axis, and wherein, upon deployment, the first coil and the second coil of the retention portion extend about an axis of the retention portion that is at least partially coextensive with the straight or curvilinear central axis of the portion of the drainage lumen.

Clause 127: The method of clause 126, further comprising, upon application of negative pressure to the ureter and/or kidney, extracting urine by drawing urine through the one or more perforations into the drainage lumen, thereby altering interstitial pressure within the patient's kidney.

Clause 128: The method of clause 126 or clause 127, wherein application of negative pressure to the ureter and/or kidney through the catheter is provided for a period of time sufficient to treat acute kidney injury due to venous congestion.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which:

FIG. 3C is a schematic drawing of another example of a retention portion for a ureteral catheter according to an example of the present invention;

FIG. 3D is a schematic drawing of another example of a retention portion for a ureteral catheter according to an example of the present invention;

FIG. 3E is a schematic drawing of another example of a retention portion for a ureteral catheter according to an example of the present invention;

FIG. 10A is a schematic drawing of another example of a urine collection assembly according to an example of the present invention;

FIG. 10B is a schematic drawing taken along section 10B-10B of the bladder anchor portion of the assembly of FIG. 10A;

DETAILED DESCRIPTION OF THE INVENTION

Figure 1:
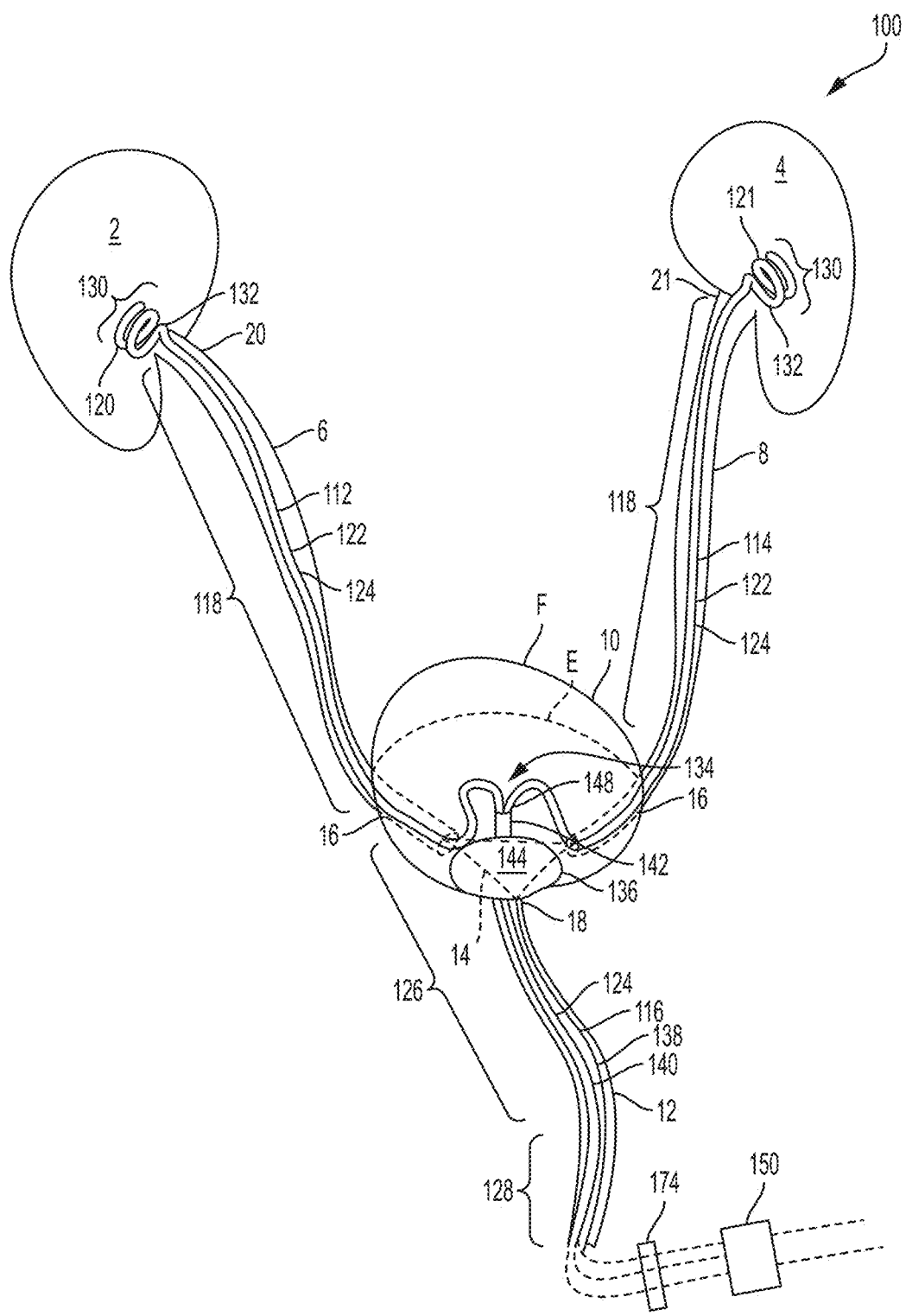
FIG. 1 is a schematic drawing of an indwelling portion of a urine collection assembly deployed in a urinary tract of a patient, according to an example of the present invention.

As used herein, the singular form of "a", "an", and "the" include plural referents unless the context clearly states otherwise.

As used herein, the terms "right", "left", "top", and derivatives thereof shall relate to the invention as it is oriented in the drawing figures. The term "proximal" refers to the portion of the catheter device that is manipulated or contacted by a user and/or to a portion of an indwelling catheter nearest to the urinary tract access site. The term "distal" refers to the opposite end of the catheter device that is configured to be inserted into a patient and/or to the portion of the device that is inserted farthest into the patient's urinary tract. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Fluid retention and venous congestion are central problems in the progression to advanced renal disease. Excess sodium ingestion coupled with relative decreases in excretion leads to isotonic volume expansion and secondary compartment involvement. In some examples, the present invention is generally directed to devices and methods for facilitating drainage of urine or waste from the bladder, ureter, and/or kidney(s) of a patient. In some examples, the present invention is generally directed to devices and methods for inducing a negative pressure in the bladder, ureter, and/or kidney(s) of a patient. While not intending to be bound by any theory, it is believed that applying a negative pressure to the bladder, ureter, and/or kidney(s) can offset the medullary nephron tubule re-absorption of sodium and water in some situations. Offsetting re-absorption of sodium and water can increase urine production, decrease total body sodium, and improve erythrocyte production. Since the intra-medullary pressures are driven by sodium and, therefore, volume overload, the targeted removal of excess sodium enables maintenance of volume loss. Removal of volume restores medullary hemostasis. Normal urine production is 1.48-1.96 L/day (or 1-1.4 ml/min).

Fluid retention and venous congestion are also central problems in the progression of prerenal Acute Kidney Injury (AKI). Specifically, AKI can be related to loss of perfusion or blood flow through the kidney(s). Accordingly, in some examples, the present invention facilitates improved renal hemodynamics and increases urine output for the purpose of relieving or reducing venous congestion. Further, it is anticipated that treatment and/or inhibition of AKI positively impacts and/or reduces the occurrence of other conditions, for example, reduction or inhibition of worsening renal function in patients with NYHA Class III and/or Class IV heart failure. Classification of different levels of heart failure are described in *The Criteria Committee of the New York Heart Association*, (1994), *Nomenclature and Criteria for Diagnosis of Diseases of the Heart and Great Vessels*, (9th ed.), Boston: Little, Brown & Co. pp. 253-256, the disclosure of which is incorporated by reference herein in its entirety. Reduction or inhibition of episodes of AKI and/or chronically decreased perfusion may also be a treatment for Stage 4 and/or Stage 5 chronic kidney disease. Chronic kidney disease progression is described in National Kidney Foundation, K/DOQI *Clinical Practice Guidelines for Chronic Kidney Disease: Evaluation, Classification and Stratification*. Am. J. Kidney Dis. 39:S1-S266, 2002 (Suppl. 1), the disclosure of which is incorporated by reference herein in its entirety.

With reference to FIG. 1, the urinary tract comprises a patient's right kidney 2 and left kidney 4. As discussed above, the kidneys 2, 4 are responsible for blood filtration and clearance of waste compounds from the body through urine. Urine produced by the right kidney 2 and the left kidney 4 is drained into a patient's bladder 10 through tubules, namely a right ureter 6 and a left ureter 8. For example, urine may be conducted through the ureters 6, 8 by peristalsis of the ureter walls, as well as by gravity. The ureters 6, 8 enter the bladder 10 through a ureter orifice or opening 16. The bladder 10 is a flexible and substantially hollow structure adapted to collect urine until the urine is excreted from the body. The bladder 10 is transitionable from an empty position (signified by reference line E) to a full position (signified by reference line F). Normally, when the bladder 10 reaches a substantially full state, urine is permitted to drain from the bladder 10 to a urethra 12 through a urethral sphincter or opening 18 located at a lower portion of the bladder 10. Contraction of the bladder 10 can be responsive to stresses and pressure exerted on a trigone region 14 of the bladder 10, which is the triangular region extending between the ureteral openings 16 and the urethral opening 18. The trigone region 14 is sensitive to stress and pressure, such that as the bladder 10 begins to fill, pressure on the trigone region 14 increases. When a threshold pressure on the trigone region 14 is exceeded, the bladder 10 begins to contract to expel collected urine through the urethra 12.

Exemplary Ureteral Catheters:

As shown in FIG. 1, a urine collection assembly 100 including ureteral catheters 112, 114 configured to be positioned within the urinary tract of a patient is illustrated. For example, distal ends 120, 121 of the ureteral catheters 112, 114 can be configured to be deployed in the patient's ureters 2, 4 and, in particular, in a renal pelvis 20, 21 area of the kidneys 6, 8.

In some examples, the urine collection assembly 100 can comprise two separate ureteral catheters, such as a first catheter 112 disposed in or adjacent to the renal pelvis 20 of the right kidney 2 and a second catheter 114 disposed in or adjacent to the renal pelvis 21 of the left kidney 4. The catheters 112, 114 can be separate for their entire lengths, or can be held in proximity to one another by a clip, ring, clamp, or other type of connection mechanism (e.g., connector 150) to facilitate placement or removal of the catheters 112, 114. In some examples, catheters 112, 114 can merge or be connected together to form a single drainage lumen. In other examples, the catheters 112, 114 can be inserted through or enclosed within another catheter, tube, or sheath along portions or segments thereof to facilitate insertion and retraction of the catheters 112, 114 from the body. For example, a bladder catheter 116 can be inserted over and/or along the same guidewire as the ureteral catheters 112, 114, thereby causing the ureteral catheters 112, 114 to extend from the distal end of the bladder catheter 116.

Figure 2A:
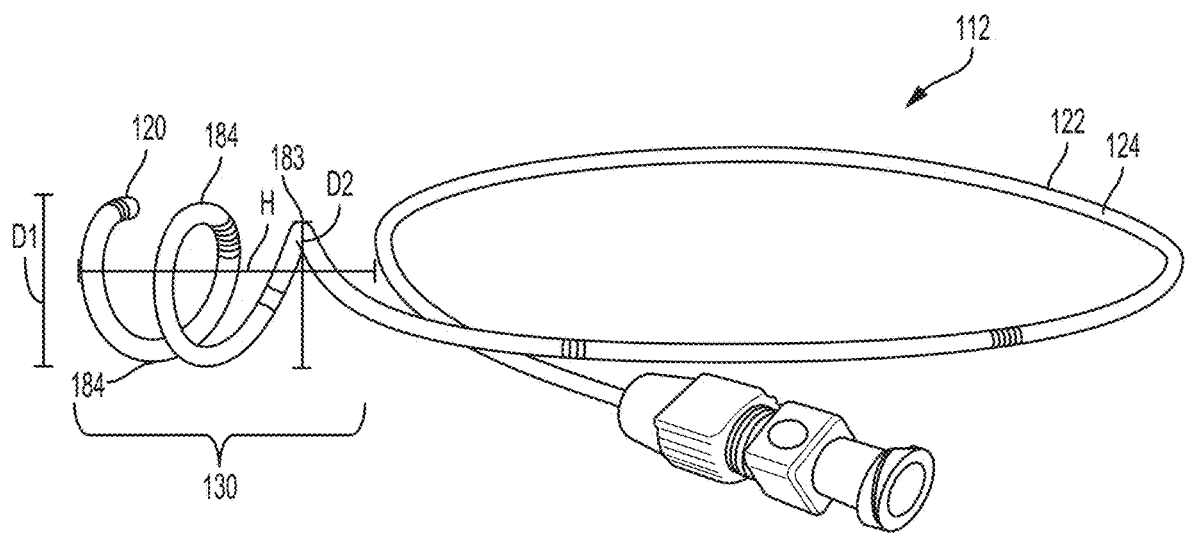
FIG. 2A is a perspective view of an exemplary ureteral catheter according to an example of the disclosure.
Figure 2B:
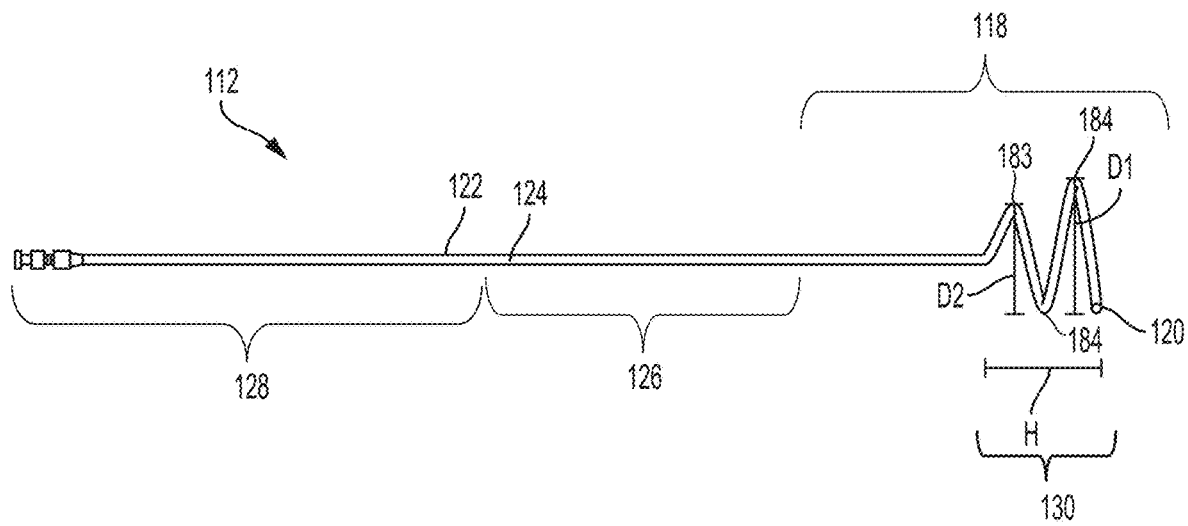
FIG. 2B is a front view of the ureteral catheter of FIG. 2A.

With reference to FIGS. 1, 2A, and 2B, an exemplary ureteral catheter 112 can comprise at least one elongated body or tube 122, the interior of which defines or comprises one or more drainage channel(s) or lumen(s), such as drainage lumen 124. The tube 122 size can range from about 1 Fr to about 9 Fr (French catheter scale). In some examples, the tube 122 can have an external diameter ranging from about 0.33 to about 3 mm, and an internal diameter ranging from about 0.165 to about 2.39 mm. In one preferable example, the tube 122 is 6 Fr and has an outer diameter of 2.0±0.1 mm. The length of the tube 122 can range from about 30 cm to about 120 cm depending on the age (e.g., pediatric or adult) and gender of the patient.

The tube 122 can be formed from a flexible and/or deformable material to facilitate advancing and/or positioning the tube 122 in the bladder 10 and ureters 6, 8 (shown in FIG. 1). The catheter material should be flexible and soft enough to avoid or reduce irritation of the renal pelvis and ureter, but should be rigid enough that the tube 122 does not collapse when the renal pelvis or other portions of the urinary tract exert pressure on the exterior of the tube 122, or when the renal pelvis and/or ureter are drawn against the tube 122 during inducement of negative pressure. For example, the tube 122 can be formed from materials including biocompatible polymers, polyvinyl chloride, polytetrafluoroethylene (PTFE) such as Teflon®, silicon coated latex, or silicon. In one preferable example, the tube 122 is formed from a thermoplastic polyurethane. At least a portion or all of the catheter 112, such as the tube 122, can be coated with a hydrophilic coating to facilitate insertion and/or removal, and/or to enhance comfort. In some examples, the coating is a hydrophobic and/or lubricious coating. For example, suitable coatings can comprise ComfortCoat® hydrophilic coating which is available from Koninklijke DSM N.V. or hydrophilic coatings comprising polyelectrolyte(s) such as are disclosed in U.S. Pat. No. 8,512,795, which is incorporated herein by reference.

In some examples, the tube 122 can comprise: a distal portion 118 (e.g., a portion of the tube 122 configured to be positioned in the ureter 6, 8 and renal pelvis 20, 21); a middle portion 126 (e.g., a portion of the tube 122 configured to extend from the distal portion through the ureteral openings 16 into the patient's bladder 10 and urethra 12); and a proximal portion 128 (e.g., a portion of the tube 122 extending from the urethra 12 to an external fluid collection container and/or pump assembly). In one preferred example, the combined length of the proximal portion 128 and the middle portion 126 of the tube 122 is about 54±2 cm. In some examples, the tube 122 terminates in another indwelling catheter and/or drainage lumen, such as in a drainage lumen of the bladder catheter 116. In that case, fluid drains from the proximal end of the ureteral catheter 112, 114 and is directed from the body through the additional indwelling catheter and/or drainage lumen.

Exemplary Ureteral Retention Portions:

With continued reference to FIGS. 1, 2A, and 2B, the distal portion 118 of the ureteral catheter 112 comprises a retention portion 130 for maintaining the distal end 120 of the catheter 112 at a desired fluid collection position proximate to or within the renal pelvis 20, 21 of the kidney 2, 4. In some examples, the retention portion 130 is configured to be flexible and bendable to permit positioning of the retention portion 130 in the ureter and/or renal pelvis. The retention portion 130 is desirably sufficiently bendable to absorb forces exerted on the catheter 112 and to prevent such forces from being translated to the ureters. For example, if the retention portion 130 is pulled in the proximal direction P (shown in FIG. 3A) toward the patient's bladder, the retention portion 130 can be sufficiently flexible to begin to unwind or be straightened so that it can be drawn through the ureter. Similarly, when the retention portion 130 can be reinserted into the renal pelvis or other suitable region within the ureter, it can be biased to return to its deployed configuration.

Figure 4A:
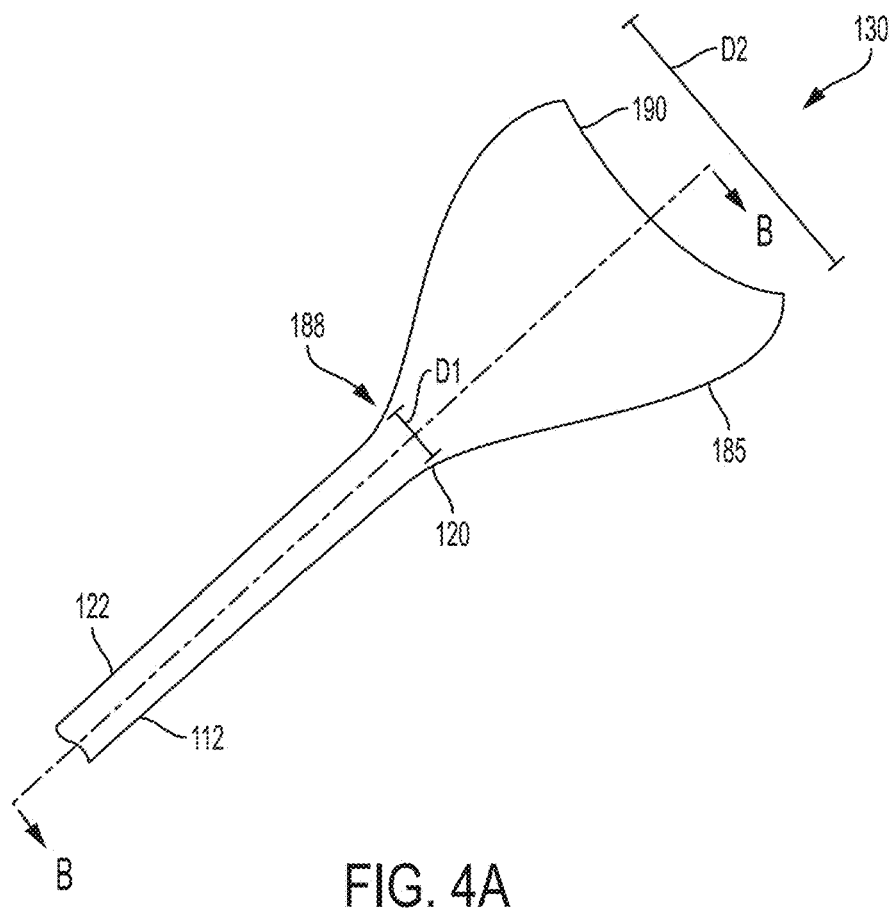
FIG. 4A is a schematic drawing of another example of a retention portion for a ureteral catheter according to an example of the present invention.
Figure 4B:
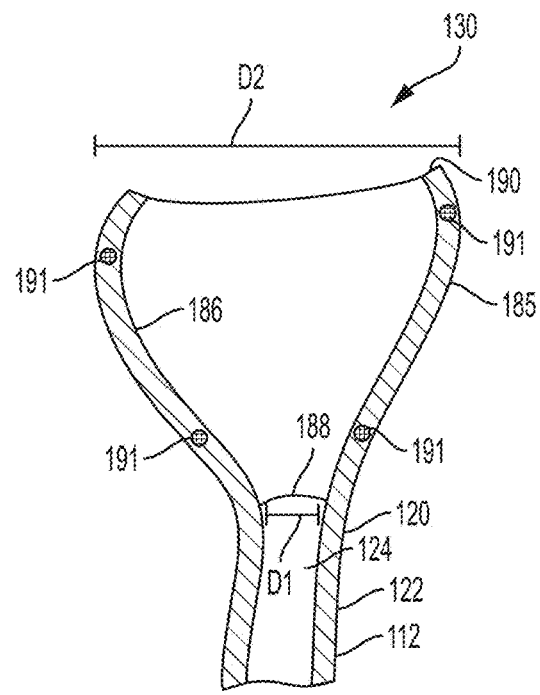
FIG. 4B is a schematic drawing of a cross-sectional view of a portion of the retention portion of FIG. 4A, taken along lines B-B of FIG. 4A.

In some examples, the retention portion 130 is integral with the tube 122. In that case, the retention portion 130 can be formed by imparting a bend or curl to the catheter body 122 that is sized and shaped to retain the catheter at a desired fluid collection location. Suitable bends or coils can include a pigtail coil, corkscrew coil, and/or helical coil. For example, the retention portion 130 can comprise one or more radially and longitudinally extending helical coils configured to contact and passively retain the catheter 112 within the ureter 6, 8 proximate to or within the renal pelvis 20, 21. In other examples, the retention portion 130 is formed from a radially flared or tapered portion of the catheter body 122. For example, the retention portion 130 can further comprise a fluid collecting portion, as shown in FIGS. 4A and 4B, such as a tapered or funnel-shaped inner surface 186. In other examples, the retention portion 130 can comprise a separate element connected to and extending from the catheter body or tube 122.

The retention portion 130 can further comprise one or more perforated sections, such as drainage holes or ports 132 (shown in FIGS. 3A-3E). A drainage port can be located, for example, at the open distal end 120, 121 of the tube 122. In other examples, perforated sections and/or drainage ports 132 are disposed along the sidewall of the distal portion 118 of the catheter tube 122. The drainage ports or holes can be used for assisting in fluid collection. In other examples, the retention portion 130 is solely a retention structure and fluid collection and/or imparting negative pressure is provided by structures at other locations on the catheter tube 122.

Referring now to FIGS. 2A, 2B, and 3A-3E, exemplary retention portions 130 comprising a plurality of helical coils, such as one or more full coils 184 and one or more half or partial coils 183, are illustrated. The retention portion 130 is capable of moving between a contracted position and the deployed position with the plurality of helical coils. For example, a substantially straight guidewire can be inserted through the retention portion 130 to maintain the retention portion 130 in a substantially straight contracted position. When the guidewire is removed, the retention portion 130 can transition to its coiled configuration. In some examples, the coils 183, 184 extend radially and longitudinally from the distal portion 118 of the tube 122. With specific reference to FIGS. 2A and 2B, in a preferred exemplary embodiment, the retention portion 130 comprises two full coils 184 and one half coil 183. The outer diameter of the full coils 184, shown by line D1, can be about 18±2 mm. The half coil 183 diameter D2 can be about 14 mm. The coiled retention portion 130 has a height H of about 16±2 mm. The retention portion 130 can further comprise the one or more drainage holes 132 (shown in FIGS. 3A-3E) configured to draw fluid into an interior of the catheter tube 122. In some examples, the retention portion 130 can comprise six drainage holes, plus an additional hole at the distal tip 120 of the retention portion. The diameter of each of the drainage holes 132 (shown in FIGS. 3A-3E) can range from about 0.7 mm to 0.9 mm and, preferably, is about 0.83±0.01 mm. The distance between adjacent drainage holes 132, specifically the linear distance between drainage holes 132 when the coils are straightened, can be about 22.5±2.5 mm.

Figure 3A:
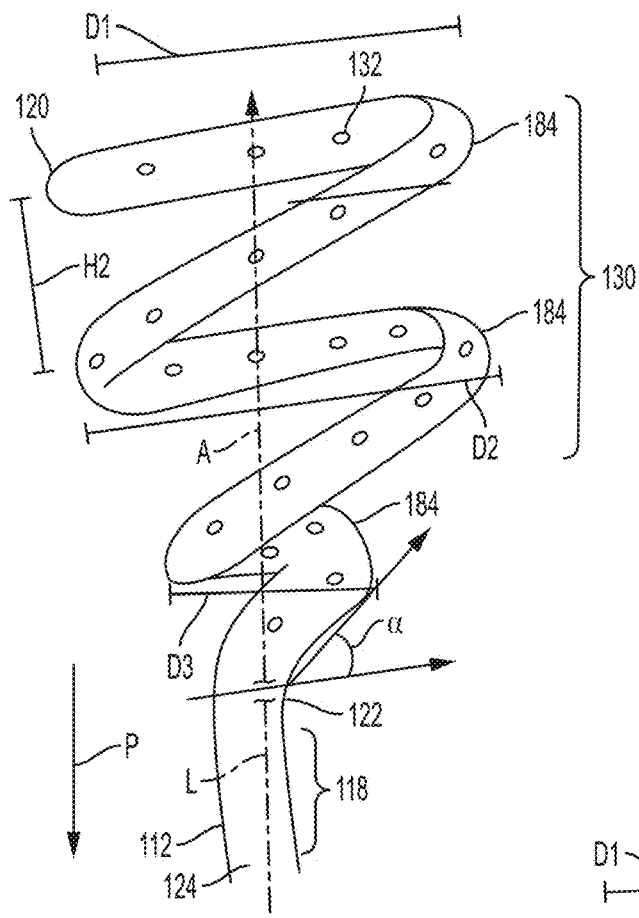
FIG. 3A is a schematic drawing of an example of a retention portion for a ureteral catheter according to an example of the present invention.
Figure 3B:
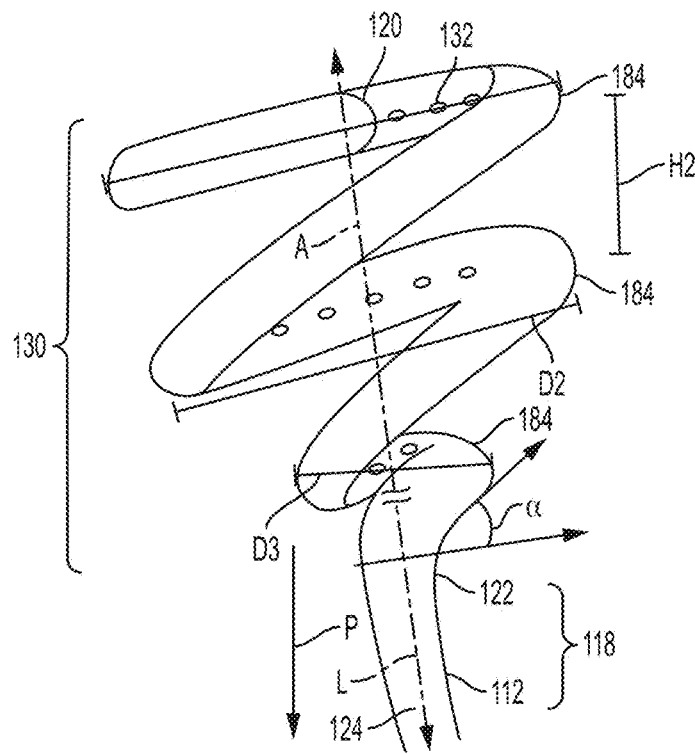
FIG. 3B is a schematic drawing of another example of a retention portion for a ureteral catheter according to an example of the present invention.

As shown in FIGS. 3A-3E, in another exemplary embodiment, the distal portion 118 of the drainage lumen proximal to the retention portion 130 defines a straight or curvilinear central axis L. In some examples, at least a half or first coil 183 and a full or second coil 184 of the retention portion 130 extend about an axis A of the retention portion 130. The first coil 183 initiates or begins at a point where the tube 122 is bent at an angle α ranging from about 15 degrees to about 75 degrees from the central axis L, as indicated by angle α, and preferably about 45 degrees. As shown in FIGS. 3A and 3B, prior to insertion in the body, the axis A can be coextensive with the longitudinal central axis L. In other examples, as shown in FIGS. 3C-3E, prior to insertion in the body, the axis A extends from and is curved or angled, for example at angle (3, relative to the central longitudinal axis L.

In some examples, multiple coils 184 can have the same inner and/or outer diameter D and height H2. In that case, the outer diameter D1 of the coils 184 may range between 10 mm and 30 mm. The height H2 between coils 184 may be about 3 mm to 10 mm.

In other examples, the retention portion 130 is configured to be inserted in the tapered portion of the renal pelvis. For example, the outer diameter D1 of the coils 184 can increase toward the distal end 120 of the tube 122, resulting in a helical structure having a tapered or partially tapered configuration. For example, the distal or maximum outer diameter D1 of the tapered helical portion ranges from about 10 mm to about 30 mm, which corresponds to the dimensions of the renal pelvis. The height H2 of the retention portion 130 ranges from about 10 mm to about 30 mm.

In some examples, the outer diameter D1 and/or height H2 of the coils 184 can vary in a regular or irregular fashion. For example, the outer diameter D1 of coils or height H2 between coils can increase or decrease by a regular amount (e.g., about 10% to about 25% between adjacent coils 184). For example, for a retention portion 130 having three coils (as shown, for example, in FIGS. 3A and 3B) an outer diameter D3 of a proximal-most coil or first coil 183 can be about 6 mm to 18 mm, an outer diameter D2 of a middle coil or second coil 185 can be about 8 mm to about 24 mm, and an outer diameter D1 of a distal-most or third coil 187 can be between about 10 mm and about 30 mm.

The retention portion 130 can further comprise the drainage ports 132 or holes disposed on or through the sidewall of the catheter tube 122 on or adjacent to the retention portion 130 to permit urine waste to flow from the outside of the catheter tube 122 to the inside of the catheter tube 122. The position and size of the drainage ports 132 can vary depending upon the desired flow rate and configuration of the retention portion. The diameter of the drainage ports 132 can range from about 0.005 mm to about 1.0 mm. The spacing between the drainage ports 132 can range from about 1.5 mm to about 5 mm. The drainage ports 132 can be spaced in any arrangement, for example, linear or offset. In some examples, the drainage ports 132 can be non-circular, and can have a surface area of about 0.00002 to 0.79 mm$^2$.

In some examples, as shown in FIG. 3A, the drainage ports 132 are located around the entire periphery of the sidewall of the catheter tube 122 to increase an amount of fluid that can be drawn into the drainage lumen 124 (shown in FIGS. 1, 2A, and 2B). In other examples, as shown in FIGS. 3B-3E, the drainage ports 132 can be disposed essentially only or only on the radially inwardly facing side of the coils 184 to prevent occlusion or blockage of the drainage ports 132, and the outwardly facing side of the coils may be essentially free of drainage ports 132 or free of drainage ports 132. For example, when negative pressure is induced in the ureter and/or renal pelvis, mucosal tissue of the ureter and/or kidney may be drawn against the retention portion 130 and may occlude some drainage ports 132 on the outer periphery of the retention portion 130. Drainage ports 132 located on the radially inward side of the retention structure would not be appreciably occluded when such tissues contact the outer periphery of the retention portion 130. Further, risk of injury to the tissues from pinching or contact with the drainage ports 132 can be reduced or ameliorated.

With reference to FIGS. 3C and 3D, other examples of ureteral catheters 112 having a retention portion 130 comprising a plurality of coils are illustrated. As shown in FIG. 3C, the retention portion 130 comprises three coils 184 extending about the axis A. The axis A is a curved arc extending from the central longitudinal axis L of the portion of the drainage lumen 181 proximal to the retention portion 130. The curvature imparted to the retention portion 130 can be selected to correspond to the curvature of the renal pelvis, which comprises a cornucopia-shaped cavity.

As shown in FIG. 3D, in another exemplary embodiment, the retention portion 130 can comprise two coils 184 extending about an angled axis A. The angled axis A extends at an angle from a central longitudinal axis L, and is angled, as shown by angle β, relative to an axis generally perpendicular to the central axis L of the portion of the drainage lumen. The angle β can range from about 15 to about 75 degrees (e.g., about 105 to about 165 degrees relative to the central longitudinal axis L of the drainage lumen portion of the catheter 112).

FIG. 3E shows another example of a ureteral catheter 112. The retention portion comprises three helical coils 184 extending about an axis A. The axis A is angled, as shown by angle β, relative to the horizontal. As in the previously-described examples, the angle β can range from about 15 to about 75 degrees (e.g., about 105 to about 165 degrees relative to the central longitudinal axis L of the drainage lumen portion of the catheter 112).

With reference to FIGS. 4A and 4B, in another example, a retention portion 130 of a ureteral catheter 112 comprises a catheter tube 122 having a widened and/or tapered distal end portion which, in some examples, is configured to be positioned in the patient's renal pelvis and/or kidney. For example, the retention portion 130 can be a funnel-shaped structure comprising an outer surface 185 configured to be positioned against the ureter and/or kidney wall and comprising an inner surface 186 configured to direct fluid toward a drainage lumen 124 of the catheter 112. The retention portion 130 can comprise a proximal end 188 adjacent to the distal end of the drainage lumen 124 and having a first diameter D1 and a distal end 190 having a second diameter D2 that is greater than the first diameter D1 when the retention portion 130 is in its deployed position. In some examples, the retention portion 130 is transitionable from a collapsed or compressed position to the deployed position. For example, the retention portion 130 can be biased radially outward such that when the retention portion 130 is advanced to its fluid collecting position, the retention portion 130 (e.g., the funnel portion) expands radially outward to the deployed state.

The retention portion 130 of the ureteral catheter 112 can be made from a variety of suitable materials that are capable of transitioning from the collapsed state to the deployed state. In one example, the retention portion 130 comprises a framework of tines or elongated members formed from a temperature sensitive shape memory material, such as nitinol. In some examples, the nitinol frame can be covered with a suitable waterproof material such as silicon to form a tapered portion or funnel. In that case, fluid is permitted to flow down the inner surface 186 of the retention portion 130 and into the drainage lumen 124. In other examples, the retention portion 130 is formed from various rigid or partially rigid sheets or materials bended or molded to form a funnel-shaped retention portion as illustrated in FIGS. 4A and 4B.

In some examples, the retention portion of the ureteral catheter 112 can include one or more mechanical stimulation devices 191 for providing stimulation to nerves and muscle fibers in adjacent tissues of the ureter(s) and renal pelvis. For example, the mechanical stimulation devices 191 can include linear or annular actuators embedded in or mounted adjacent to portions of the sidewall of the catheter tube 122 and configured to emit low levels of vibration. In some examples, mechanical stimulation can be provided to portions of the ureters and/or renal pelvis to supplement or modify therapeutic effects obtained by application of negative pressure. While not intending to be bound by theory, it is believed that such stimulation affects adjacent tissues by, for example, stimulating nerves and/or actuating peristaltic muscles associated with the ureter(s) and/or renal pelvis. Stimulation of nerves and activation of muscles may produce changes in pressure gradients or pressure levels in surrounding tissues and organs which may contribute to or, in some cases, enhance therapeutic benefits of negative pressure therapy.

Figure 5A:
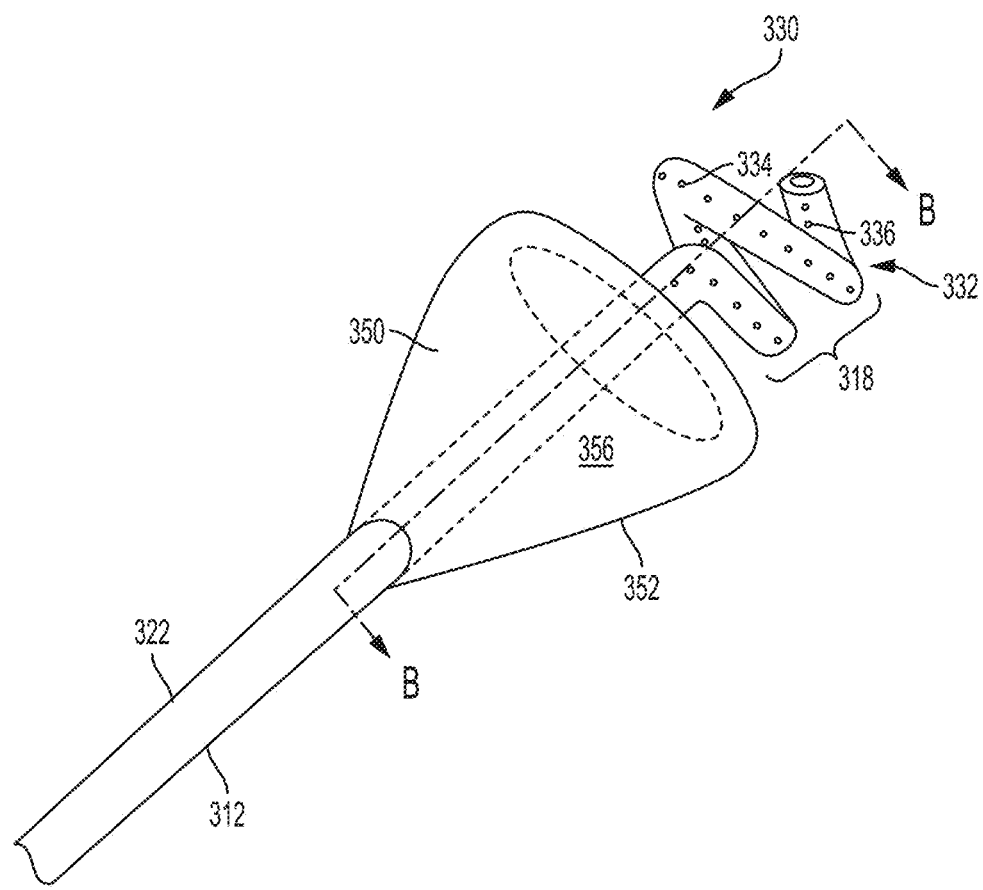
FIG. 5A is a schematic drawing of another example of a retention portion for a ureteral catheter according to an example of the present invention.
Figure 5B:
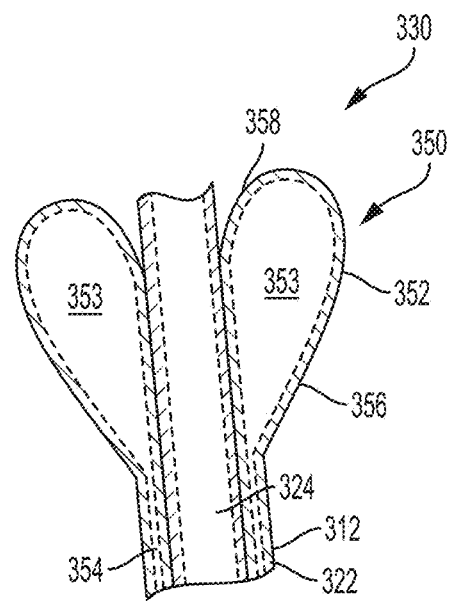
FIG. 5B is a schematic drawing of a portion of a cross-sectional view of the retention portion of FIG. 5A, taken along lines B-B of FIG. 5A.

With reference to FIGS. 5A and 5B, according to another example, a retention portion 330 of a ureteral catheter 312 comprises a catheter tube 322 having a distal portion 318 formed in a helical structure 332 and an inflatable element or balloon 350 positioned proximal to the helical structure 332 to provide an additional degree of retention in the renal pelvis and/or fluid collection location. A balloon 350 can be inflated to pressure sufficient to retain the balloon in the renal pelvis or ureter, but low enough to avoid distending or damaging these structures. Suitable inflation pressures are known to those skilled in the art and are readily discernible by trial and error. As in previously-described examples, the helical structure 332 can be imparted by bending the catheter tube 322 to form one or more coils 334. The coils 334 can have a constant or variable diameter and height as described above. The catheter tube 322 further comprises a plurality of drainage ports 336 disposed on the sidewall of the catheter tube 322 to allow urine to be drawn into the drainage lumen 324 of the catheter tube 322 and to be directed from the body through the drainage lumen 324, for example on the inwardly facing and/or outwardly facing sides of the coil 334.

As shown in FIG. 5B, the inflatable element or balloon 350 can comprise an annular balloon-like structure having, for example, a generally heart-shaped cross section and comprising a surface or cover 352 defining a cavity 353. The cavity 353 is in fluid communication with an inflation lumen 354 extending parallel to the drainage lumen 324 defined by the catheter tube 322. The balloon 350 can be configured to be inserted in the tapered portion of the renal pelvis and inflated such that an outer surface 356 thereof contacts and rests against an inner surface of the ureter and/or renal pelvis. The inflatable element or balloon 350 can comprise a tapered inner surface 358 extending longitudinally and radially inward towards the catheter tube 322. The inner surface 358 can be configured to direct urine toward the catheter tube 322 to be drawn into the drainage lumen 324. The inner surface 358 can also be positioned to prevent fluid from pooling in the ureter, such as around the periphery of the inflatable element or balloon 350. The inflatable retention portion or balloon 350 is desirably sized to fit within the renal pelvis and can have a diameter ranging from about 10 mm to about 30 mm.

Figure 6:
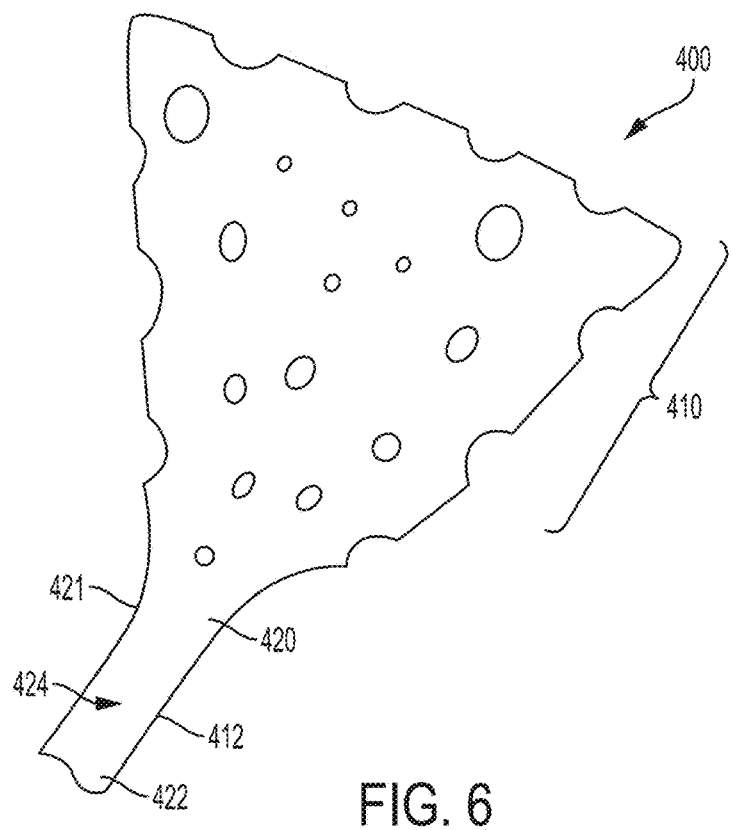
FIG. 6 is a schematic drawing of another example of a retention portion for a ureteral catheter according to an example of the present invention.
Figure 7:
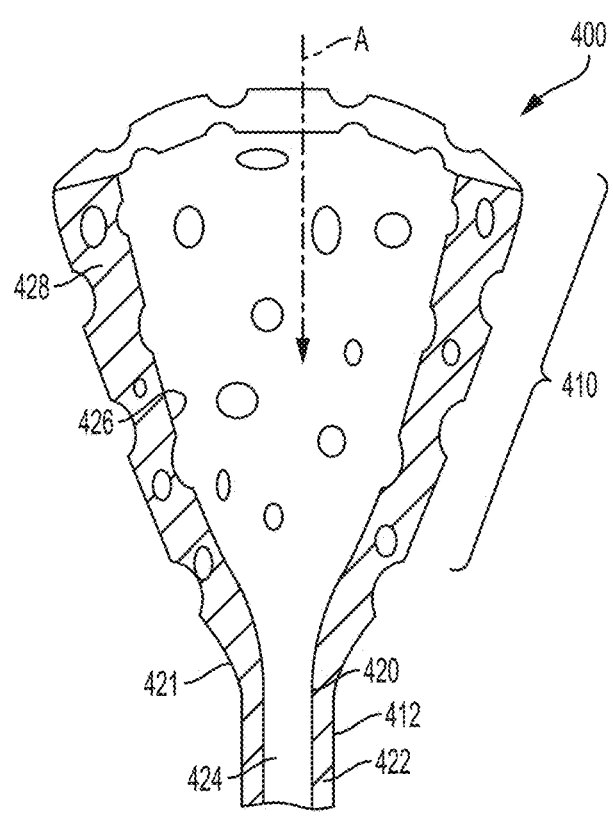
FIG. 7 is a schematic drawing of a cross section of another example of a retention portion for a ureteral catheter according to an example of the present invention.

With reference to FIGS. 6 and 7, in some examples, an assembly 400 including a ureteral catheter 412 comprising a retention portion 410 is illustrated. The retention portion 410 is formed from a porous and/or sponge-like material that is attached to a distal end 421 of a catheter tube 422. The porous material can be configured to channel and/or absorb urine and direct the urine toward a drainage lumen 424 of the catheter tube 422. As shown in FIG. 7, the retention portion 410 can be a porous wedge shaped-structure configured for insertion and retention in the patient's renal pelvis. The porous material comprises a plurality of holes and/or channels. Fluid can be drawn through the channels and holes, for example, by gravity or upon inducement of negative pressure through the catheter 412. For example, fluid can enter the wedge-shaped retention portion 410 through the holes and/or channels and is drawn toward a distal opening 420 of the drainage lumen 424, for example, by capillary action, peristalsis, or as a result of the inducement of negative pressure in the holes and/or channels. In other examples, as shown in FIG. 7, the retention portion 410 comprises a hollow, funnel structure formed from the porous sponge-like material. As shown by arrow A, fluid is directed down an inner surface 426 of the funnel structure into the drainage lumen 424 defined by the catheter tube 422. Also, fluid can enter the funnel structure of the retention portion 410 through holes and channels in the porous sponge-like material of a sidewall 428. For example, suitable porous materials can include open-celled polyurethane foams, such as polyurethane ether. Suitable porous materials can also include laminates of woven or non-woven layers comprising, for example, polyurethane, silicone, polyvinyl alcohol, cotton, or polyester, with or without antimicrobial additives such as silver, and with or without additives for modifying material properties such as hydrogels, hydrocolloids, acrylic, or silicone.

Figure 8:
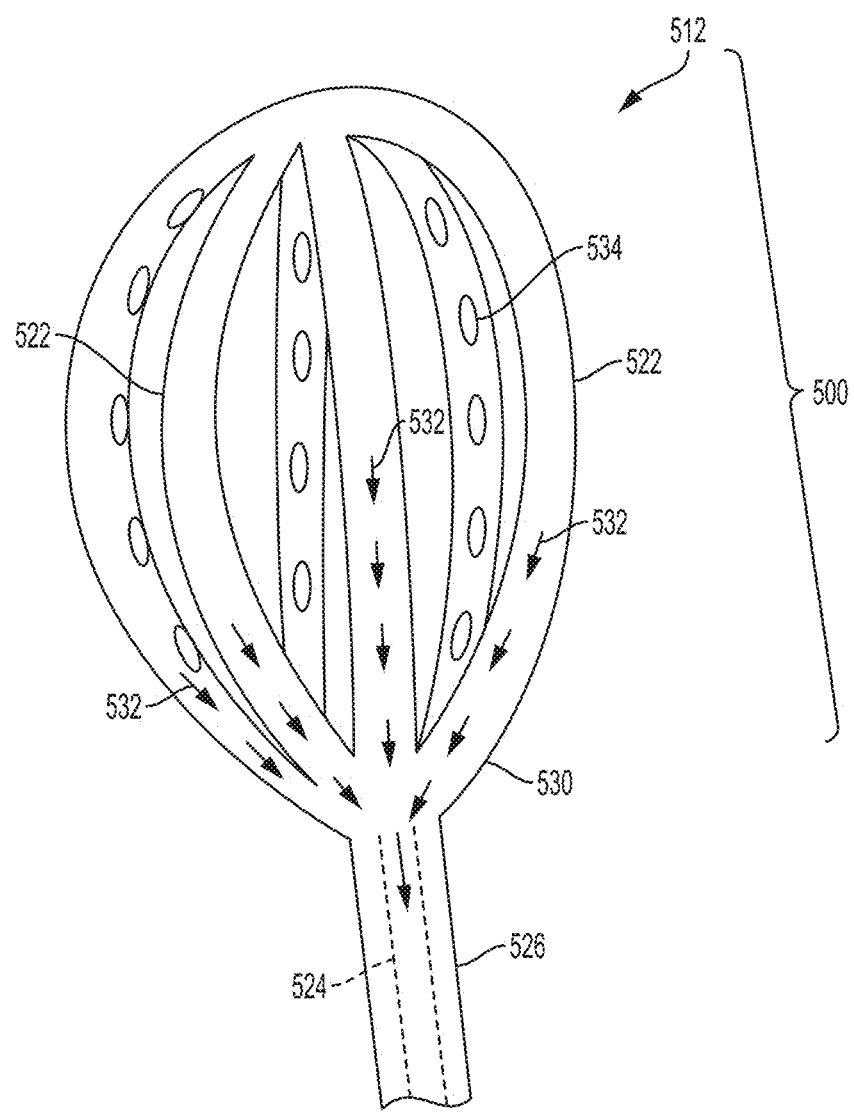
FIG. 8 is a schematic drawing of another example of a retention portion for a ureteral catheter according to an example of the present invention.

With reference to FIG. 8, according to another example, a retention portion 500 of a ureteral catheter 512 comprises an expandable cage 530. The expandable cage 530 comprises one or more longitudinally and radially extending hollow tubes 522. For example, the tubes 522 can be formed from an elastic, shape memory material such as nitinol. The cage 530 is configured to transition from a contracted state, for insertion through the patient's urinary tract, to a deployed state for positioning in the patient's ureters and/or kidney. The hollow tubes 522 comprise a plurality of drainage ports 534 which can be positioned on the tubes, for example, on radially inward facing sides thereof. The ports 534 are configured to permit fluid to flow or be drawn through the ports 534 and into the respective tubes 522. The fluid drains through the hollow tubes 522 into a drainage lumen 524 defined by a catheter body 526 of the ureteral catheter 512. For example, fluid can flow along the path indicated by the arrows 532 in FIG. 8. In some examples, when negative pressure is induced in the renal pelvis, kidneys, and/or ureters, portions of the ureter wall and/or renal pelvis may be drawn against the outward facing surfaces of the hollow tubes 522. The drainage ports 534 are positioned and configured so as not to be appreciably occluded by ureteral structures upon application of negative pressure to the ureters and/or kidney.

Figure 9A:
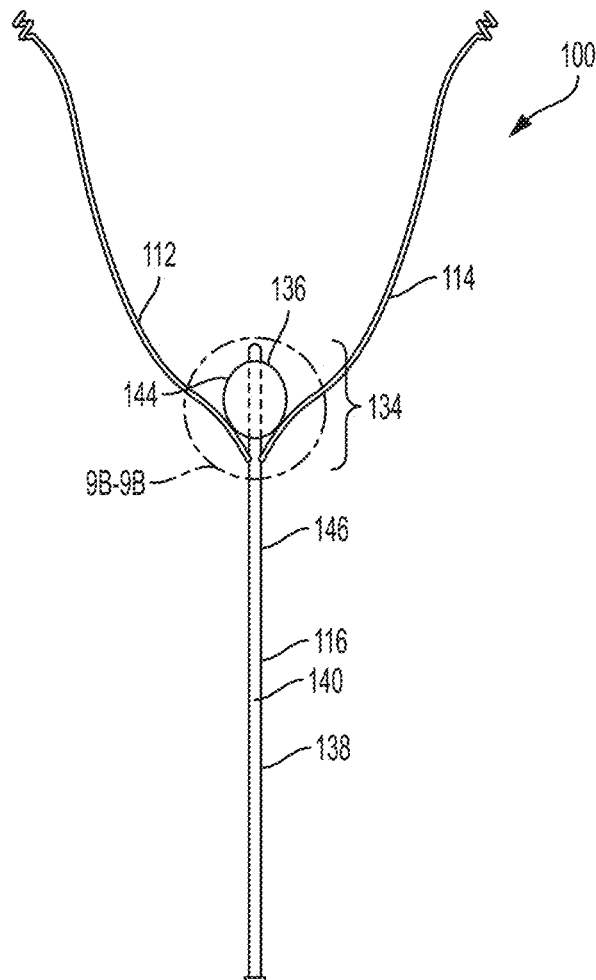
FIG. 9A is a schematic drawing of another example of a urine collection assembly according to an example of the present invention.
Figure 11A:
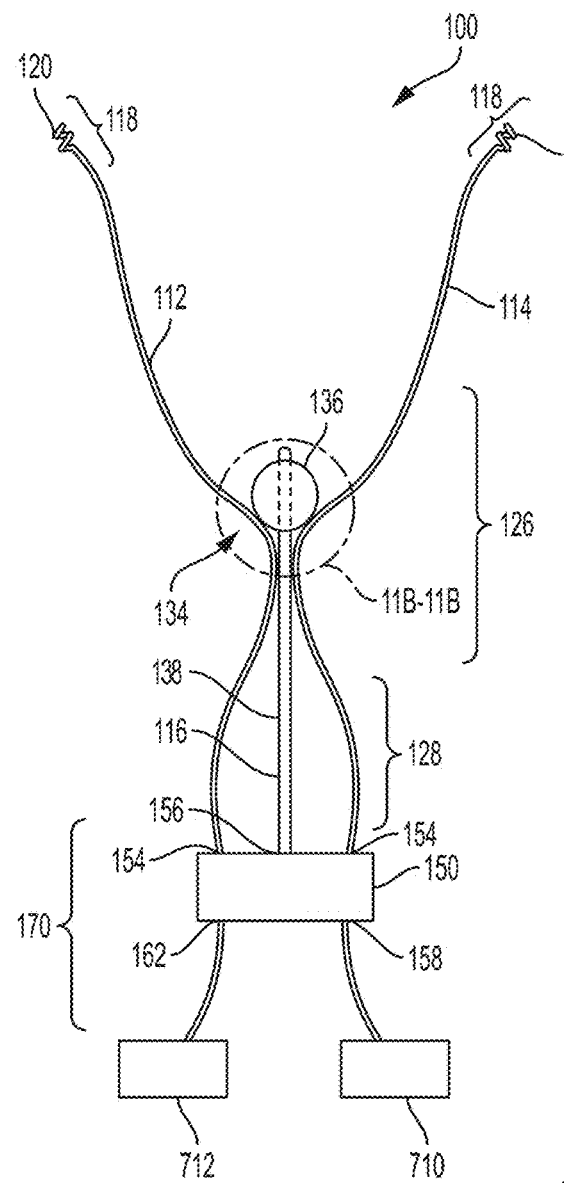
FIG. 11A is a schematic drawing of a urine collection assembly according to an example of the present invention.

Exemplary Urine Collection Assembly:

Referring now to FIGS. 1, 9A, and 11A, the urine collection assembly 100 further comprises a bladder catheter 116. The distal ends 120, 121 of the ureteral catheters 112, 114 can be connected to the bladder catheter 116 to provide a single drainage lumen for urine, or the ureteral catheter(s) can drain via separate tube(s) from the bladder catheter 116.

Exemplary Bladder Catheter

The bladder catheter 116 comprises a deployable seal and/or anchor 136 for anchoring, retaining, and/or providing passive fixation for indwelling portions of the urine collection assembly 100 and, in some examples, to prevent premature and/or untended removal of assembly components during use. The anchor 136 is configured to be located adjacent to the lower wall of the patient's bladder 10 (shown in FIG. 1) to prevent patient motion and/or forces applied to indwelling catheters 112, 114, 116 from translating to the ureters. The bladder catheter 116 comprises an interior of which defines a drainage lumen 140 configured to conduct urine from the bladder 10 to an external urine collection container 712 (shown in FIG. 19). In some examples, the bladder catheter 116 size can range from about 8 Fr to about 24 Fr. In some examples, the bladder catheter 116 can have an external diameter ranging from about 2.7 to about 8 mm. In some examples, the bladder catheter 116 can have an internal diameter ranging from about 2.16 to about 6.2 mm. The bladder catheter 116 can be available in different lengths to accommodate anatomical differences for gender and/or patient size. For example, the average female urethra length is only a few inches, so the length of a tube 138 can be rather short. The average urethra length for males is longer due to the penis and can be variable. It is possible that woman can use bladder catheters 116 with longer length tubes 138 provided that the excess tubing does not increase difficulty in manipulating and/or preventing contamination of sterile portions of the catheter 116. In some examples, a sterile and indwelling portion of the bladder catheter 116 can range from about 1 inch to 3 inches (for women) to about 20 inches for men. The total length of the bladder catheter 116 including sterile and non-sterile portions can be from one to several feet.

The catheter tube 138 can comprise one or more drainage ports 142 configured to be positioned in the bladder 10 for drawing urine into the drainage lumen 140. For example, excess urine left in the patient's bladder 10 during placement of the ureteral catheters 112, 114 is expelled from the bladder 10 through the ports 142 and drainage lumen 140. In addition, any urine that is not collected by the ureteral catheters 112, 114 accumulates in the bladder 10, and can be conducted from the urinary tract through the drainage lumen 140. The drainage lumen 140 may be pressurized to a negative pressure to assist in fluid collection or may be maintained at atmospheric pressure such that fluid is collected by gravity and/or as a result of partial contraction of the bladder 10. In some examples, the ureteral catheters 112, 114 may extend from the drainage lumen 140 of the bladder catheter 116 to facilitate and/or simplify insertion and placement of the ureteral catheters 112, 114.

With specific reference to FIG. 1, the deployable seal and/or anchor 136 is disposed at or adjacent to a distal end 148 of the bladder catheter 116. The deployable anchor 136 is configured to transition between a contracted state for insertion into the bladder 10 through the urethra 12 and urethral opening 18 and a deployed state. The anchor 136 is configured to be deployed in and seated adjacent to a lower portion of the bladder 10 and/or against the urethral opening 18. For example, the anchor 136 can be positioned adjacent to the urethral opening 18 to enhance suction of a negative pressure applied to the bladder 10 or, in the absence of negative pressure, to partially, substantially, or entirely seal the bladder 10 to ensure that urine in the bladder 10 is directed through the drainage lumen 140 and to prevent leakage to the urethra 12. For a bladder catheter 116 including an 8 Fr to 24 Fr elongated tube 138, the anchor 136 can be about 12 Fr to 32 Fr (e.g., having a diameter of about 4 mm to about 10.7 mm) in the deployed state, and preferably between about 24 Fr and 30 Fr. A 24 Fr anchor has a diameter of about 8 mm. It is believed that a 24 Fr anchor 136 would be a single size suitable for all or most patients. For a catheter 116 with a 24 Fr anchor 136, a suitable length of the anchor 136 is between about 1.0 cm and 2.3 cm, and preferably about 1.9 cm (about 0.75 in).

Figure 12A:
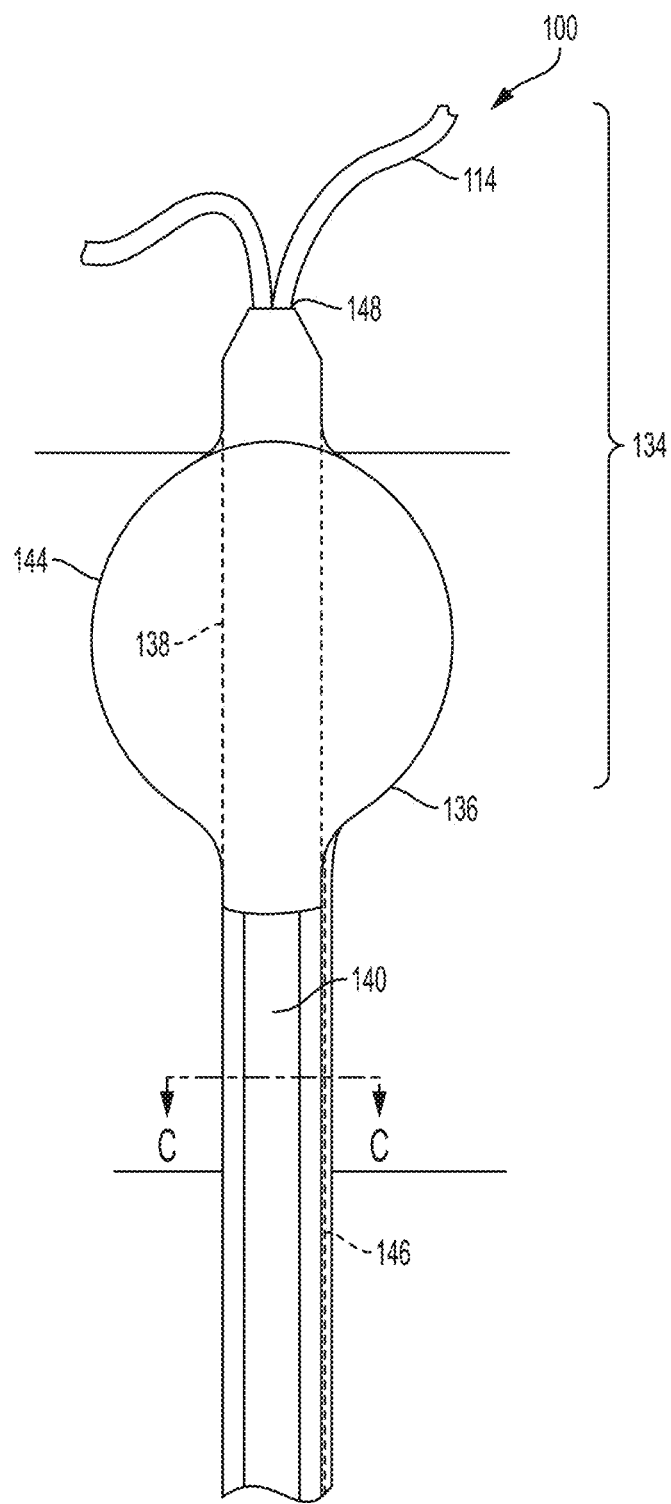
FIG. 12A is a schematic drawing of another bladder anchor portion of a urine collection assembly according to an example of the disclosure.
Figure 13:
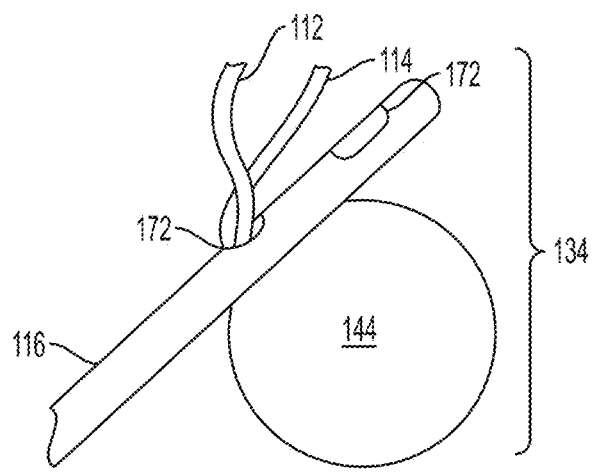
FIG. 13 is a schematic drawing of another example of a bladder anchor portion of a urine collection assembly according to an example of the present disclosure.

Exemplary Bladder Anchor Structures:

With specific reference to FIGS. 1, 12A, and 13, an exemplary bladder anchor 136 in the form of an expandable balloon 144 is illustrated. The expandable (e.g., inflatable) balloon 144 can be, for example, a spherical balloon of a Foley catheter. The balloon 144 can be about 1.0 cm to 2.3 cm in diameter, and preferably about 1.9 cm (0.75 in) in diameter. The balloon 144 is preferably formed from a flexible material including, for example, biocompatible polymers, polyvinyl chloride, polytetrafluoroethylene (PTFE) such as Teflon®, silicon coated latex, or silicon.

The balloon 144 is in fluid connection with an inflation lumen 146, and is inflated by introducing fluid into the balloon 144. In a deployed state, the balloon 144 can be a substantially spherical structure mounted to and extending radially outward from the catheter tube 138 of the bladder catheter 116 and comprising a central cavity or channel for the catheter tube 138 to pass through. In some examples, the catheter tube 138 extends through the cavity defined by the balloon 144, such that the open distal end 148 of the catheter tube 138 extends distally beyond the balloon 144 and toward the center of the bladder 10 (shown in FIG. 1). Excess urine collected in the bladder 10 can be drawn into the drainage lumen 140 through the distal open end 148 thereof.

Figure 14:
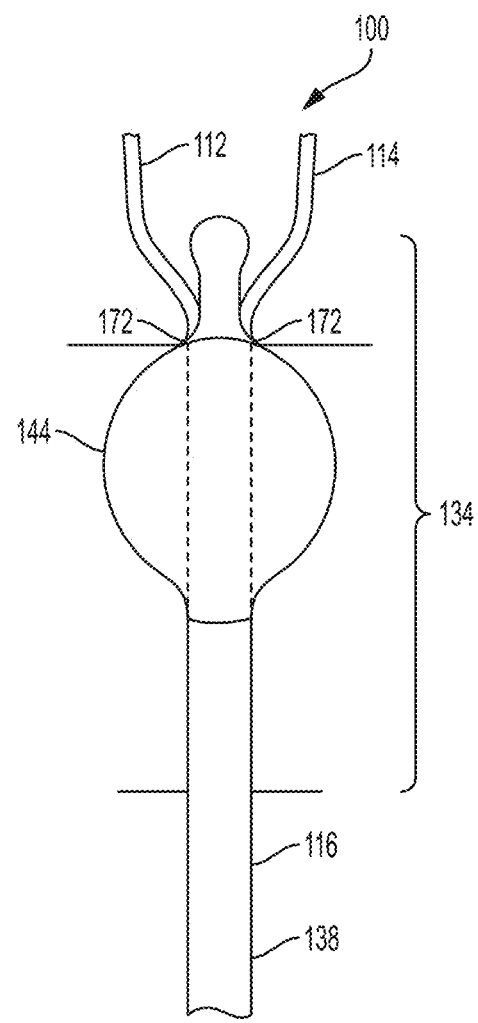
FIG. 14 is a schematic drawing of another example of a bladder anchor portion of a urine collection assembly according to an example of the present disclosure.

As shown in FIGS. 1 and 12A, in one example, the ureteral catheters 112, 114 extend from the open distal end 148 of the drainage lumen 140. In another example, as shown in FIG. 14, the ureteral catheters 112, 114 extend through ports 172 or openings disposed on a sidewall of the catheter tube 138 at a position distal to the balloon 144. The ports 172 can be circular or oval shaped. The ports 172 are sized to receive the ureteral catheters 112, 114 and, accordingly, can have a diameter ranging from about 0.33 mm to about 3 mm. As shown in FIG. 13, in another example, the bladder catheter 116 is positioned next to the balloon 144, rather than extending through a central cavity defined by the balloon 144. As in other examples, the ureteral catheters 112, 114 extend through ports 172 in the sidewall of the bladder catheter 116 and into the bladder 10.

Figure 12B:
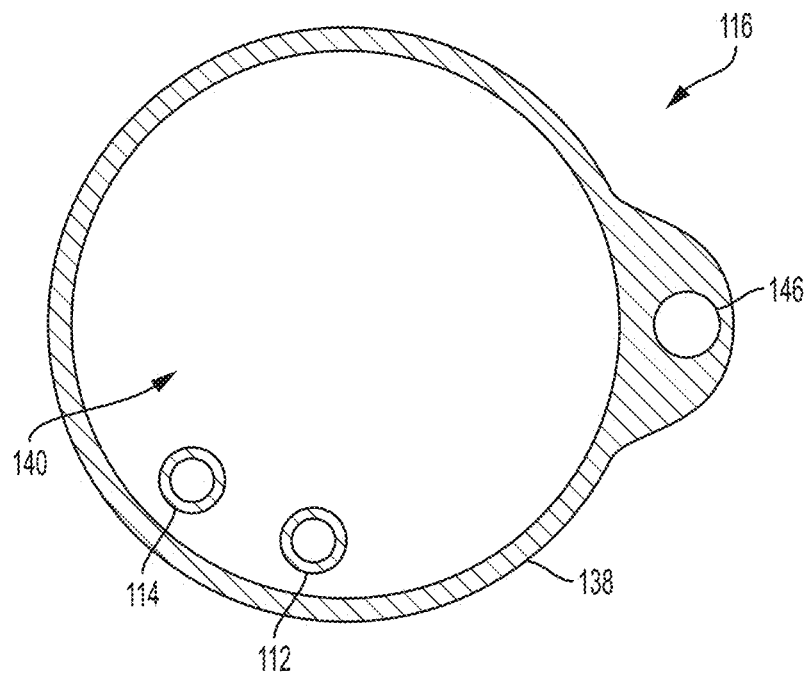
FIG. 12B is a schematic drawing of a cross section of a bladder catheter of a urine collection assembly, taken along line C-C of FIG. 12A.
Figure 12C:
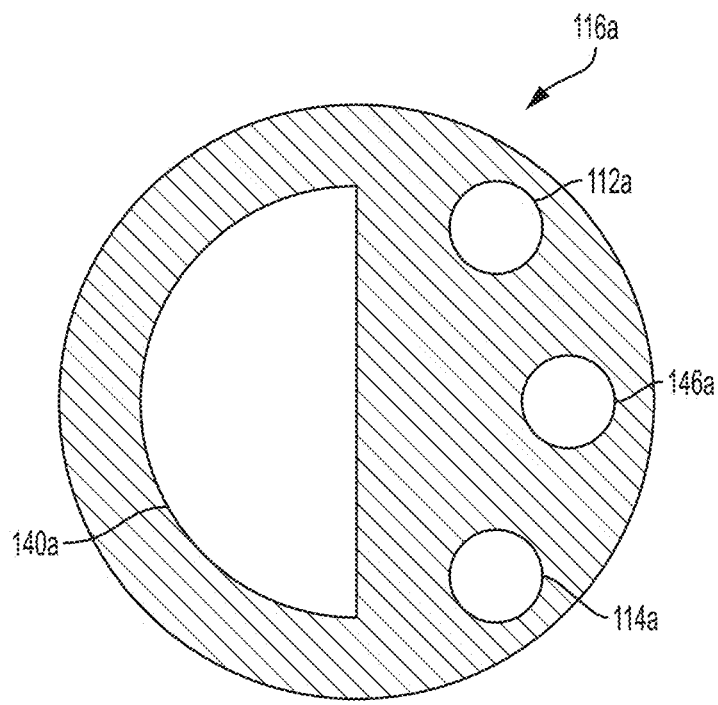
FIG. 12C is a schematic drawing of a cross section of another example of a bladder catheter of a urine collection assembly.

With reference to FIG. 12B, a cross-sectional view of the bladder catheter 116 and ureteral catheter(s) 112, 114 is shown. As shown in FIG. 12B, in one example, the bladder catheter 116 comprises a dual lumen catheter with the drainage lumen 140 at a central region thereof and a smaller inflation lumen 146 extending along the periphery of the catheter tube 138. The ureteral catheters 112, 114 are inserted or enclosed in the central drainage lumen 140. The ureteral catheters 112, 114 are single-lumen catheters having a sufficiently narrow cross section to fit within the drainage lumen 140. In some examples, as discussed above, the ureteral catheters 112, 114 extend through the entire bladder catheter 116. In other examples, the ureteral catheters 112, 114 terminate in the drainage lumen 140 of the bladder catheter 116, either at a position in the patient's ureter 12 or in an external portion of the drainage lumen 140. As shown in FIG. 12C, in another example, a bladder catheter 116a is a multi-lumen catheter that defines at least four lumens, namely a first lumen 112a for conducting fluid from the first ureteral catheter 112 (shown in FIG. 1), a second lumen 114a for conducting fluid from the second ureteral catheter 114 (shown in FIG. 1), a third lumen 140a for drainage of urine from the bladder 10 (shown in FIG. 1), and the inflation lumen 146a for conducting fluid to and from the balloon 144 (shown in FIG. 12A) for inflation and retraction thereof.

Figure 15:
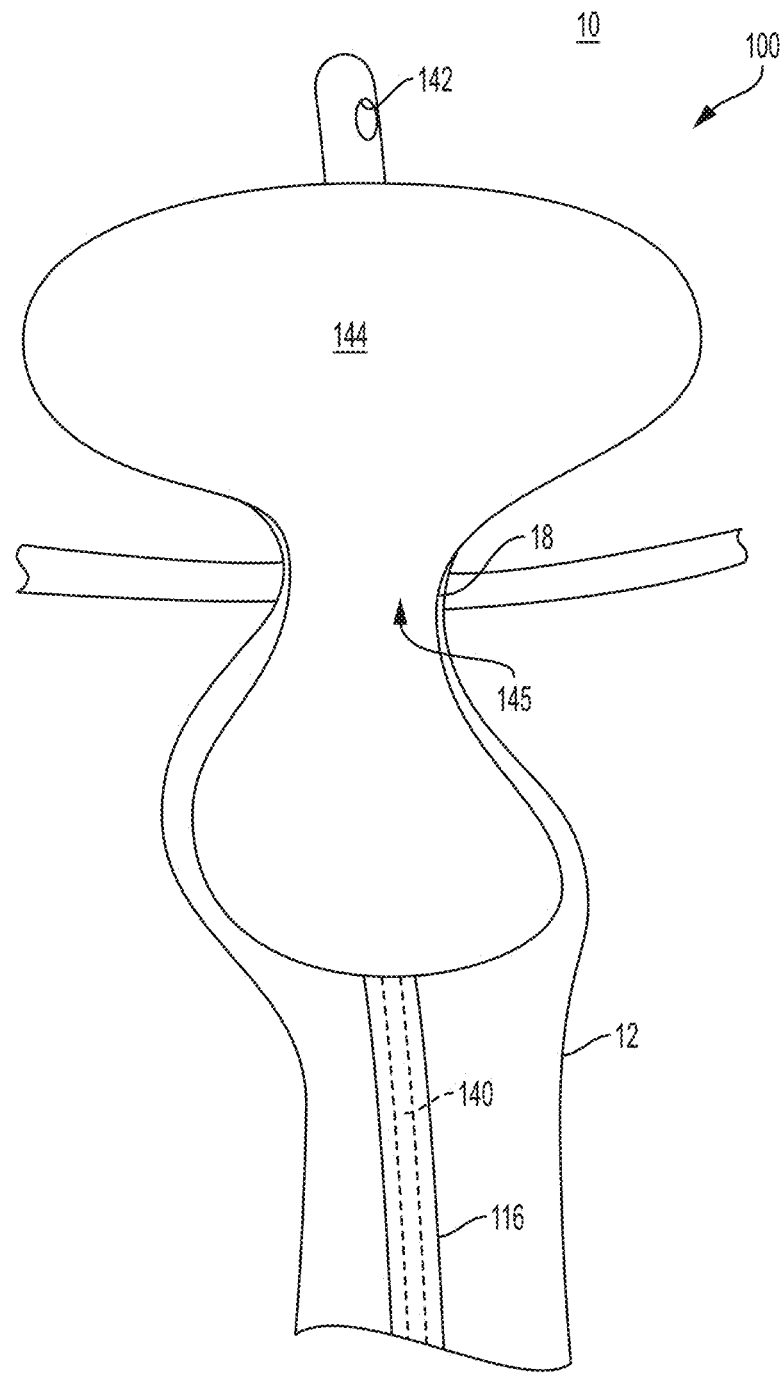
FIG. 15 is a schematic drawing of another example of a bladder anchor portion of a urine collection assembly configured to be deployed in the patient's bladder and urethra according to an example of the present invention.

As shown in FIG. 15, another example of a catheter balloon 144 for use with a urine collection assembly 100 is illustrated. In the example of FIG. 15, the balloon 144 is configured to be positioned partially within the patient's bladder 10 and partially within the urethra 12 to provide an enhanced bladder seal. A central portion 145 of the balloon 144 is configured to be radially contracted by the urethral opening 18, thereby defining a bulbous upper volume configured to be positioned in the lower portion of the bladder 10 and a bulbous lower volume configured to be position at the distal portion of the urethra 12. As in previously-described examples, the bladder catheter 116 extends through a central cavity defined by the balloon 144 and toward a central portion of the bladder 10 and includes drainage ports 142 for conducting urine from the bladder 10 through a drainage lumen 140 of the catheter 116. The drainage ports 142 can be generally circular or oval shaped and can have a diameter of about 0.005 mm to about 0.5 mm.

Figure 9B:
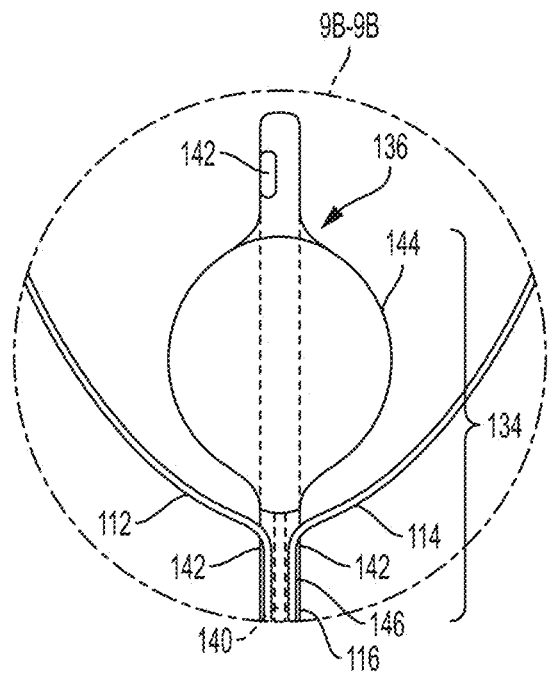
FIG. 9B is a partial schematic drawing taken along section 9B-9B of the bladder anchor portion of the assembly of FIG. 9A.

With reference again to FIGS. 9A and 9B, another example of a urine collection assembly 100 including a bladder anchor device 134 is illustrated. The bladder anchor device 134 comprises a bladder catheter 116 defining a drainage lumen 140, an inflation lumen 146, and an anchor 136, namely, another example of an expandable balloon 144, configured to be seated in a lower portion of the bladder 10. Unlike in the previously-described examples, the ports 142 configured to receive the ureteral catheters 112, 114 are disposed proximal to and/or below the balloon 144. The ureteral catheters 112, 114 extend from the ports 142 and, as in previously-described examples, extend through the ureteral orifices or openings of the bladder and into the ureters. When the anchor 136 is deployed in the bladder, the ports 142 are disposed in a lower portion of the bladder adjacent to the urethral opening. The ureteral catheters 112, 114 extend from the ports 172 and between a lower portion of the balloon 144 and the bladder wall. In some examples, the catheters 112, 114 may be positioned to prevent the balloon 144 and/or bladder wall from occluding the ports 142 so that excess urine collected in the bladder can be drawn into the ports 142 to be removed from the body.

With reference again to FIGS. 10A and 10B, in another example of a urine collection assembly 200, an expandable cage 210 anchors the assembly 200 in the bladder. The expandable cage 210 comprises a plurality of flexible members 212 or tines extending longitudinally and radially outward from a catheter body 238 of a bladder catheter 216 which, in some examples, can be similar to those discussed above with respect to the retention portion of the ureteral catheter of FIG. 8. The members 212 can be formed from a suitable elastic and shape memory material such as nitinol. In a deployed position, the members 212 or tines are imparted with a sufficient curvature to define a spherical or ellipsoid central cavity 242. The cage 210 is attached to an open distal open end 248 of the catheter tube or body 238, to allow access to a drainage lumen 240 defined by the tube or body 238. The cage 210 is sized for positioning within the lower portion of the bladder and can define a diameter and length ranging from 1.0 cm to 2.3 cm, and preferably about 1.9 cm (0.75 in).

In some examples, the cage 210 further comprises a shield or cover 214 over distal portions of the cage 210 to prevent or reduce the likelihood that tissue, namely, the distal wall of the bladder, will be caught or pinched as a result of contact with the cage 210 or member 212. More specifically, as the bladder contracts, the inner distal wall of the bladder comes into contact with the distal side of the cage 210. The cover 214 prevents the tissue from being pinched or caught, may reduce patient discomfort, and protect the device during use. The cover 214 can be formed at least in part from a porous and/or permeable biocompatible material, such as a woven polymer mesh. In some examples, the cover 214 encloses all or substantially all of the cavity 242. In that case, the cover 214 defines openings suitable for receiving the ureteral catheters 112, 114. In some examples, the cover 214 covers only about the distal ⅔, about the distal half, or about the distal third portion or any amount, of the cage 210. In that case, the ureteral catheters 112, 114 pass through the uncovered portion of the cage 210.

The cage 210 and cover 214 are transitionable from a contracted position, in which the members 212 are contracted tightly together around a central portion and/or around the bladder catheter 116 to permit insertion through a catheter or sheath to the deployed position. For example, in the case of a cage 210 constructed from a shape memory material, the cage 210 can be configured to transition to the deployed position when it is warmed to a sufficient temperature, such as body temperature (e.g., 37° C.). In the deployed position, the cage 210 has a diameter D that is preferably wider than the urethral opening, such that the cage 210 provides support for the ureteral catheters 112, 114 and prevents patient motion from translating through the ureteral catheters 112, 114 to the ureters. When the assembly 200 is deployed in the urinary tract, the ureteral catheter(s) 112, 114 extend from the open distal end 248 of the bladder catheter 216, past the longitudinally extending members 212 of the cage 210, and into the bladder. Advantageously, the open (e.g., low profile) arrangement of the members 212 or tines facilitates manipulation of the ureteral catheters 112, 114 from the bladder catheter 116 and through the bladder. Particularly, the open arrangement of the members 212 or tines does not obstruct or occlude the distal opening 248 and/or drainage ports of the bladder catheter 216, making manipulation of the catheters 112, 114 easier to perform.

Figure 16:
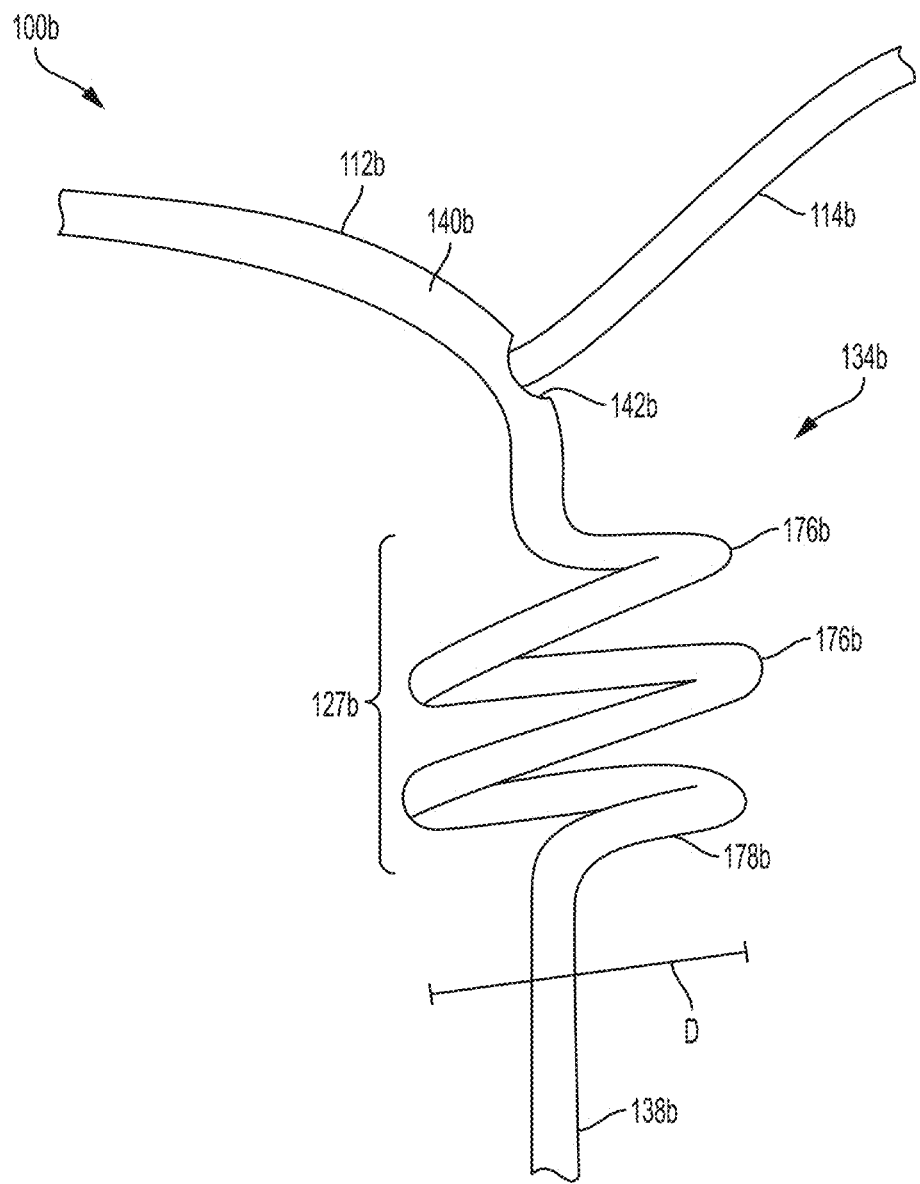
FIG. 16 is a schematic drawing of another example of a bladder anchor portion of a urine collection assembly according to an example of the present invention.

With reference to FIG. 16, a portion of another example of a urine collection assembly 100b is illustrated. The urine collection assembly 100b comprises a first ureteral catheter 112b and a second ureteral catheter 114b. The assembly 100b does not comprise a separate bladder drainage catheter as is provided in the previously-described examples. Instead, one of the ureteral catheters 112b comprises a helical portion 127b formed in the middle portion of the catheter 112b (e.g., the portion of the catheter configured to be positioned in a lower portion of the patient's bladder). The helical portion 127b comprises at least one and preferably two or more coils 176b. The coils 176b can be formed by bending a catheter tube 138b to impart a desired coil configuration. A lower coil 178b of the helical portion 127b is configured to be seated against and/or adjacent to the urethral opening. Desirably, the helical portion 127b has a diameter D that is larger than the urethral opening to prevent the helical portion 127b from being drawn into the urethra. In some examples, a port 142b or opening is disposed in the sidewall of the catheter tube 138b for connecting the first ureteral catheter 112b to the second ureteral catheter 114b. For example, the second catheter 114b can be inserted in the port 142b to form a fluid connection between the first ureteral catheter 112b and the second ureteral catheter 114b. In some examples, the second catheter 114b terminates at a position just inside a drainage lumen 140b of the first catheter 112b. In other examples, the second ureteral catheter 114b is threaded through and/or extends along the length of the drainage lumen 140b of the first catheter 112b, but is not in fluid communication with the drainage lumen 140b.

Figure 11B:
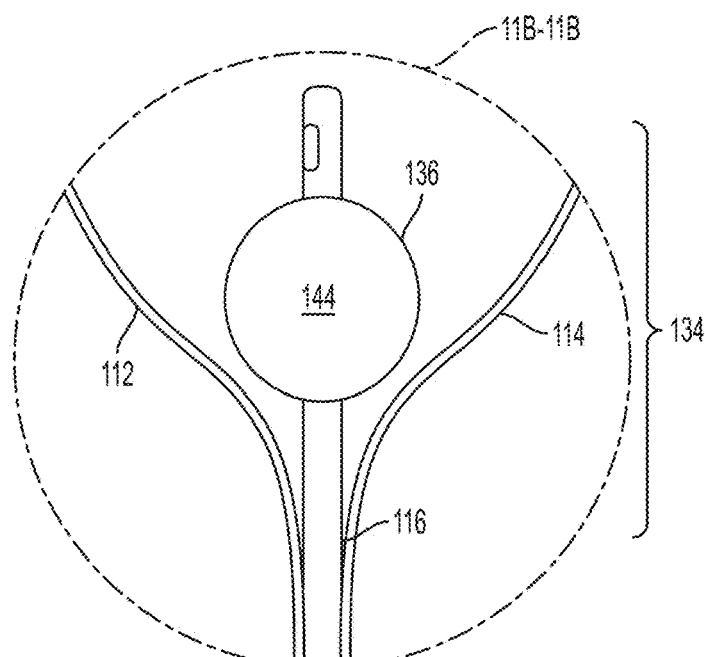
FIG. 11B is a schematic drawing taken along section 11B-11B of a bladder anchor portion of the assembly of FIG. 11A.

With reference again to FIGS. 11A and 11B, another exemplary urine collection assembly 100 comprising a bladder anchor device 134 is illustrated. The assembly 100 includes ureteral catheters 112, 114 and a separate bladder catheter 116. More specifically, as in previously-described examples, the assembly 100 includes the ureteral catheters 112, 114, each of which comprise a distal portion 118 positioned in or adjacent to the right kidney and the left kidney, respectively. The ureteral catheters 112, 114 comprise indwelling portions 118, 126, 128 extending through the ureters, bladder, and urethra. The ureteral catheters 112, 114 further comprise an external portion 170 extending from the patient's urethra 12 to a pump assembly for imparting negative pressure to the renal pelvis and/or kidneys. The assembly 100 also includes a bladder anchor device 134 comprising a bladder catheter 116 and an anchor 136 (e.g., a Foley catheter) deployed in the bladder to prevent or reduce effects of patient motion from being translated to the ureteral catheters 112, 114 and/or ureters. The bladder catheter 116 extends from the bladder 10, through the urethra, and to a fluid collection container for fluid collection by gravity or negative pressure drainage. In some examples, an external portion of the tubing extending between a collection vessel 712 and a pump 710 (shown in FIG. 19) can comprise one or more filters for preventing urine and/or particulates from entering the pump. As in previously-described examples, the bladder catheter 116 is provided to drain excess urine left in the patient's bladder during catheter placement.

Figure 17A:
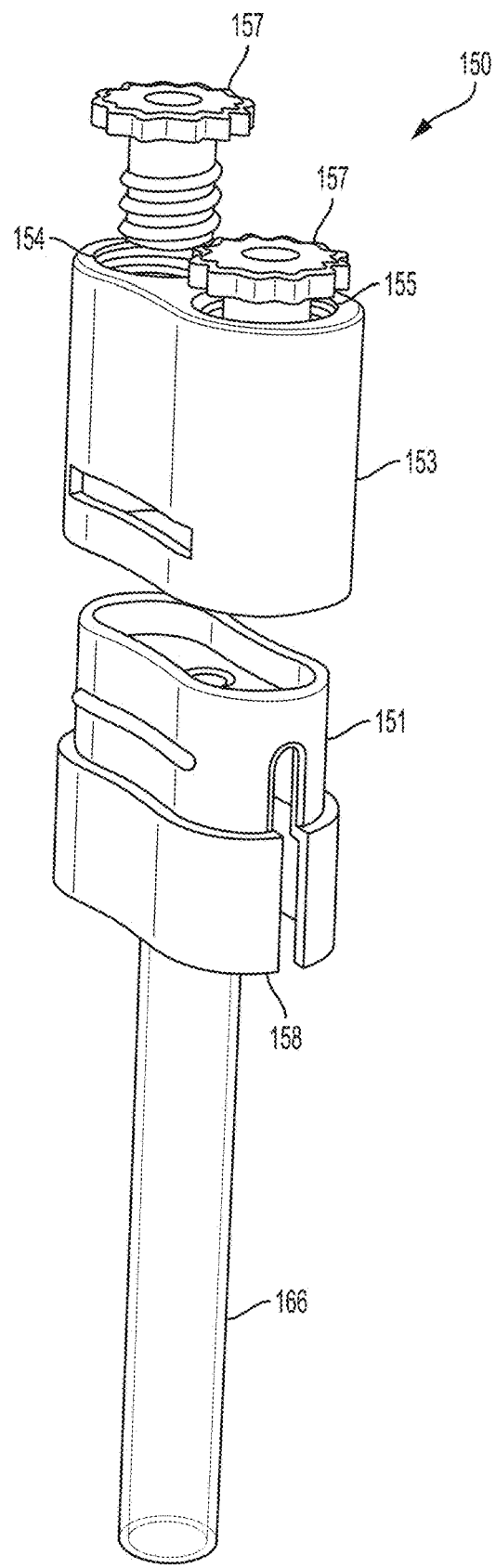
FIG. 17A is an exploded perspective view of a connector for a urine collection assembly according to an example of the disclosure.
Figure 17B:
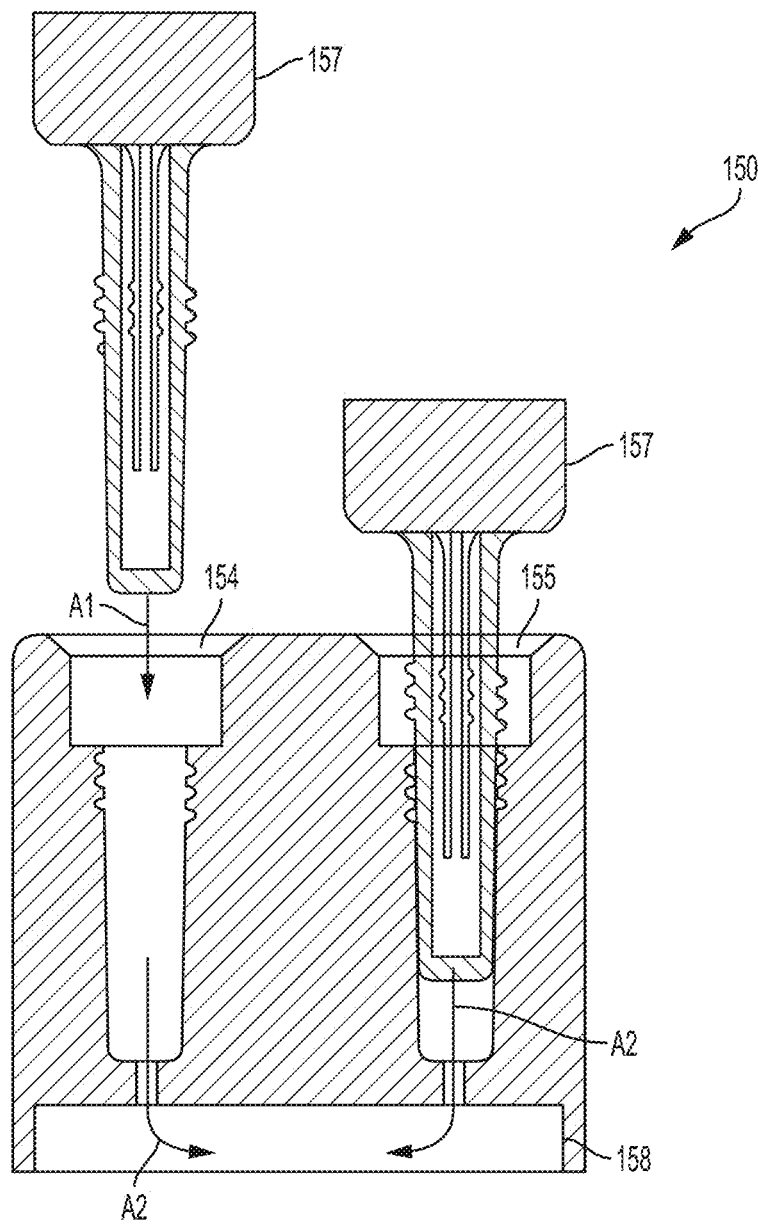
FIG. 17B is a cross-sectional view of a portion of the connector of FIG. 17A.

Exemplary Connectors and Clamps:

With reference to FIGS. 1, 11A, and 17A-17C, the assembly 100 further comprises a manifold or connector 150 for joining the two or more of the catheters 112, 114, 116 at a position outside the patient's body. In some examples, the connector 150 can be a clamp, manifold, valve, fastener, or other element of a fluid path set, as is known in the art, for joining a catheter to external flexible tubing. As shown in FIGS. 17A and 17B, the manifold or connector 150 comprises a two-piece body comprising an inner portion 151 mounted inside an outer housing 153. The inner portion 151 defines channels for conducting fluid between inflow ports 154, 155 and an outflow port 158. The inflow port(s) 154, 155 can comprise threaded sockets 157 configured to receive proximal portions of the catheters 112, 114. Desirably, the sockets 157 are a suitable size to securely receive and hold flexible tubing sized between 1 Fr and 9 Fr. Generally, a user cinches the sockets 157 around the respective catheter tubes 122 by spinning the socket 157 into the ports 154, 155 in the direction of arrow A1 (shown in FIG. 17B).

Once the catheters 112, 114 are mounted to the connector 150, urine entering the connector 150 through the vacuum inflow ports 154, 155 is directed through a fluid conduit in the direction of arrow A2 (shown in FIG. 17B) to the vacuum outflow port 158. The vacuum outflow port 158 can be connected to the fluid collection container 712 and/or pump assembly 710 (shown in FIG. 19) by, for example, flexible tubing 166 defining a fluid flow path.

Figure 17C:
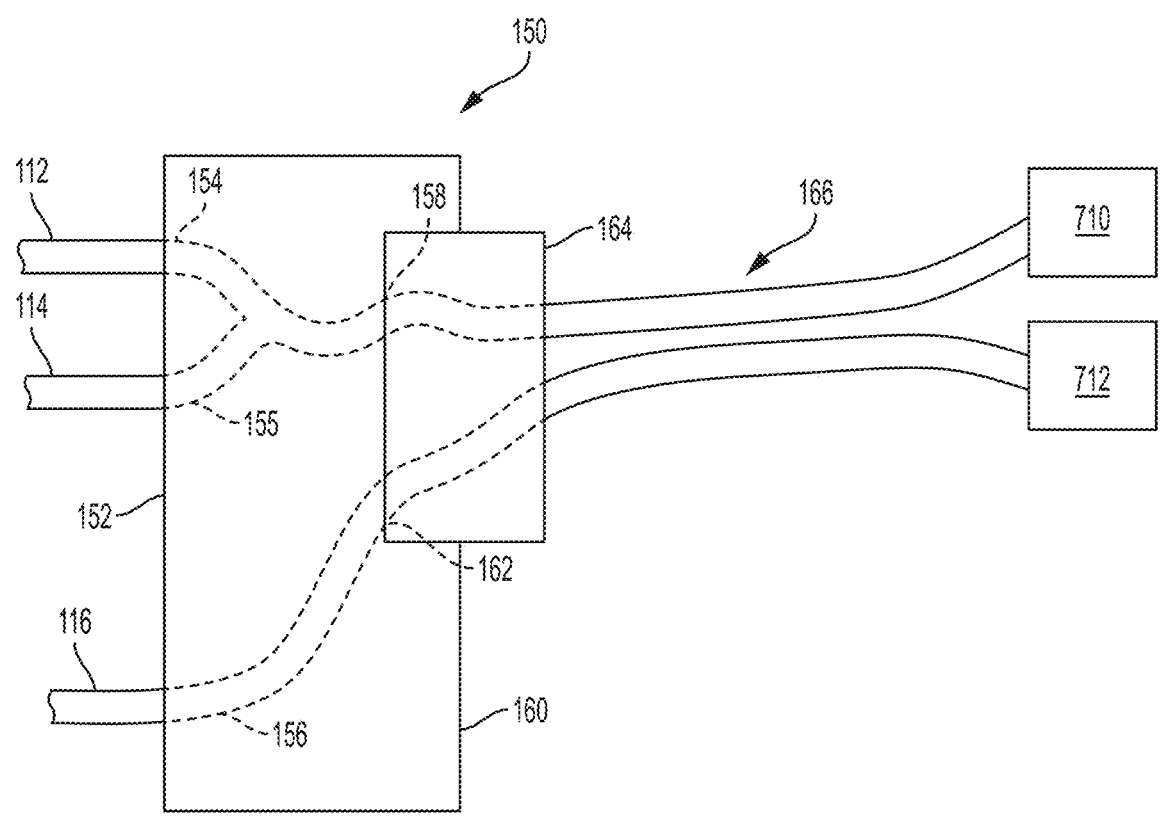
FIG. 17C is a schematic drawing of a connector for a urine collection assembly according to an example of the disclosure.

With specific reference to FIG. 17C, another exemplary connector 150 can be configured to connect three or more catheters 112, 114, 116 to outflow ports 158, 162. The connector 150 can comprise a structure or body having a distal side 152 comprising two or more vacuum inflow ports 154, 155 configured to be connected to proximal ends of the ureteral catheters 112, 114, and a separate gravity drainage port 156 configured to connect to the proximal end of the bladder catheter 116. The vacuum ports 154, 155 and/or proximal ends of the ureteral catheters 112, 114 can comprise a specific configuration to ensure that the ureteral catheters 112, 114 are connected to the vacuum source and not to some other fluid collection assembly. Similarly, the gravity drainage port 156 and/or proximal end of the bladder catheter 116 can comprise another connector configuration to ensure that the bladder catheter 116 and not one of the ureteral catheters 112, 114 is permitted to drain by gravity drainage. In other examples, the ports 154, 155, 156 and/or proximal ends of the catheters 112, 114, 116 can include visual indicia to assist in correctly setting up the fluid collection system.

In some examples, urine received in the vacuum ports 154, 155 can be directed through a Y-shaped conduit to a single vacuum outflow port 158 located on a proximal side 160 of the connector 150. As in previously-described examples, the vacuum outflow port 158 can be connected to the fluid collection container 712 and/or pump 710 by suitable flexible tubing or other conduits for drawing urine from the body and for inducing negative pressure in the ureters and/or kidneys. In some examples, the outflow port 156 and/or connector 150 can be configured to attach only to vacuum sources or pumps operating within a predetermined pressure range or power level to prevent exposing the ureteral catheters 112, 114 to elevated levels or intensity of negative pressure. The proximal side 160 of the connector 150 can also comprise a gravity outflow port 162 in fluid communication with the inflow port 156. The gravity outflow port 162 can be configured to be connected directly to the urine collection container 712 for urine collection by gravity drainage.

With continued reference to FIG. 17C, in some examples, in order to facilitate system setup and implementation, the vacuum outflow port 158 and the gravity outflow port 162 are disposed in close proximity so that a single socket 164, bracket, or connector can be coupled to the connector 150 to establish fluid communication with each port 158, 162. The single socket or connector can be coupled to a multi-conduit hose or tube (e.g., flexible tubing 166) having a first conduit in fluid communication with the pump 710 and a second conduit in fluid communication with the collection container 712. Accordingly, a user can easily set up the external fluid collection system by inserting the single socket 164 in the connector 150 and connecting the respective conduits to one of the fluid collection container 712 and pump 710 (shown in FIG. 19). In other examples, a length of flexible tubing 166 is connected between the urine collection container 712 and the gravity outflow port 162, and a separate length of flexible tubing is connected between the pump 710 and the vacuum outflow port 158.

Exemplary Fluid Sensors:

With reference again to FIG. 1, in some examples, the assembly 100 further comprises sensors 174 for monitoring fluid characteristics of urine being collected from the ureters 6, 8 and/or bladder 10. As discussed herein in connection with FIG. 19, information obtained from the sensors 174 can be transmitted to a central data collection module or processor and used, for example, to control operation of an external device, such as the pump 710 (shown in FIG. 19). The sensors 174 can be integrally formed with one or more of the catheters 112, 114, 116 such as, for example, embedded in a wall of the catheter body or tube and in fluid communication with drainage lumens 124, 140. In other examples, one or more of the sensors 174 can be positioned in a fluid collection container 712 (shown in FIG. 19) or in internal circuitry of an external device, such as the pump 710.

Exemplary sensors 174 that can be used with the urine collection assembly 100 can comprise one or more of the following sensor types. For example, the catheter assembly 100 can comprise a conductance sensor or electrode that samples conductivity of urine. The normal conductance of human urine is about 5-10 mS/m. Urine having a conductance outside of the expected range can indicate that the patient is experiencing a physiological problem, which requires further treatment or analysis. The catheter assembly 100 can also comprise a flow meter for measuring a flow rate of urine through the catheter(s) 112, 114, 116. Flow rate can be used to determine a total volume of fluid excreted from the body. The catheter(s) 112, 114, 116 can also comprise a thermometer for measuring urine temperature. Urine temperature can be used to collaborate the conductance sensor. Urine temperature can also be used for monitoring purposes, as urine temperature outside of a physiologically normal range can be indicative of certain physiological conditions.

Method of Insertion of a Urine Collection Assembly:

Having described the urine collection assembly 100 including the ureteral catheter retention portions and bladder anchor device (e.g., a standard or modified Foley-type catheter), methods for insertion and deployment of the assemblies will now be discussed in detail.

Figure 18A:
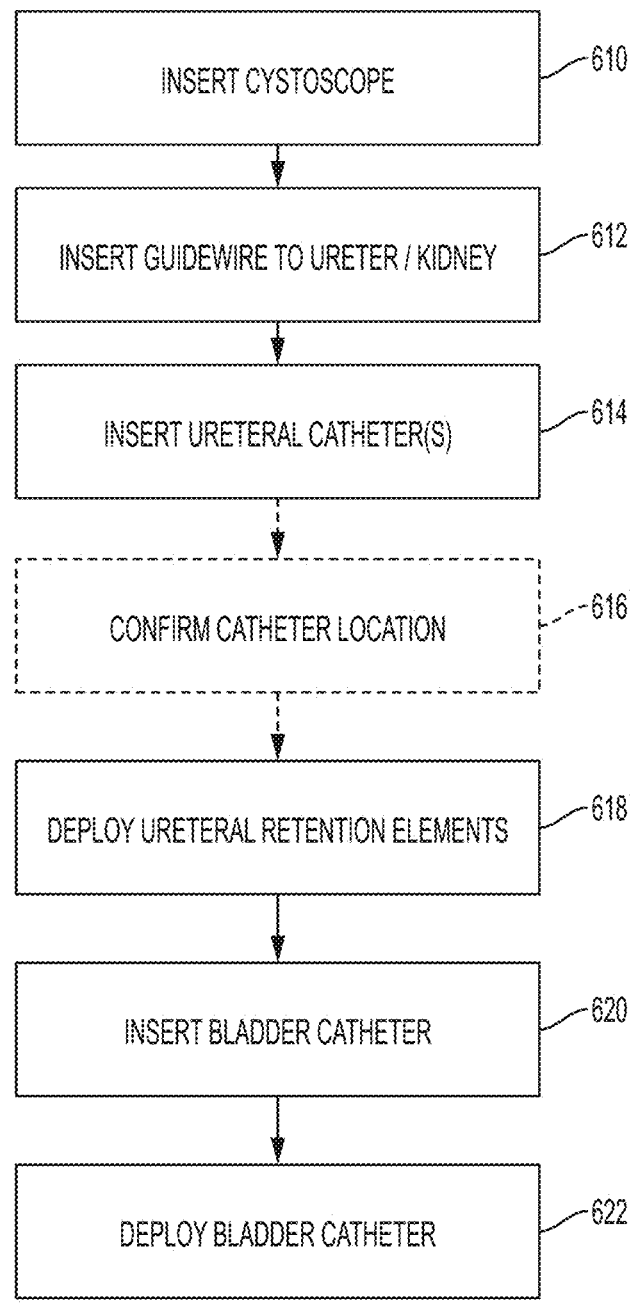
FIG. 18A is a flow chart illustrating a process for insertion and deployment of a ureteral catheter or urine collection assembly according to an example of the present invention.

With reference to FIG. 18A, steps for positioning a fluid collection assembly in a patient's body and, optionally, for inducing negative pressure in a patient's ureter and/or kidneys are illustrated. As shown at box 610, a medical professional or caregiver inserts a flexible or rigid cystoscope through the patient's urethra and into the bladder to obtain visualization of the ureteral orifices or openings. Once suitable visualization is obtained, as shown at box 612, a guidewire is advanced through the urethra, bladder, ureteral opening, ureter, and to a desired fluid collection position, such as the renal pelvis of the kidney. Once the guidewire is advanced to the desired fluid collection position, a ureteral catheter of the present invention (examples of which are discussed in detail above) is inserted over the guidewire to the fluid collection position, as shown at box 614. In some examples, the location of the ureteral catheter can be confirmed by fluoroscopy, as shown at box 616. Once the position of the distal end of the catheter is confirmed, as shown at box 618, the retention portion of the ureteral catheter can be deployed. For example, the guidewire can be removed from the catheter, thereby allowing the distal end and/or retention portion to transition to a deployed position. In some examples, the deployed distal end portion of the catheter does not entirely occlude the ureter and/or renal pelvis, such that urine is permitted to pass outside the catheter and through the ureters into the bladder. Since moving the catheter can exert forces against urinary tract tissues, avoiding complete blockage of the ureters avoids application of force to the ureter sidewalls, which may cause injury.

After the ureteral catheter is in place and deployed, the same guidewire can be used to position a second ureteral catheter in the other ureter and/or kidney using the same insertion and positioning methods described herein. For example, the cystoscope can be used to obtain visualization of the other ureteral opening in the bladder, and the guidewire can be advanced through the visualized ureteral opening to a fluid collection position in the other ureter. A catheter can be drawn alongside the guidewire and deployed in the manner described herein. Alternatively, the cystoscope and guidewire can be removed from the body. The cystoscope can be reinserted into the bladder over the first ureteral catheter. The cystoscope is used, in the manner described above, to obtain visualization of the ureteral opening and to assist in advancing a second guidewire to the second ureter and/or kidney for positioning of the second ureteral catheter. Once the ureteral catheters are in place, in some examples, the guidewire and cystoscope are removed. In other examples, the cystoscope and/or guidewire can remain in the bladder to assist with placement of the bladder catheter.

Optionally, a bladder catheter can also be used. Once the ureteral catheters are in place, as shown at box 620, the medical professional or caregiver can insert a distal end of a bladder catheter in a collapsed or contracted state through the urethra of the patient and into the bladder. The bladder catheter can be a conventional Foley bladder catheter or a bladder catheter of the present invention as discussed in detail above. Once inserted in the bladder, as shown at box 622, an anchor connected to and/or associated with the bladder catheter is expanded to a deployed position. For example, when an expandable or inflatable catheter is used, fluid may be directed through an inflation lumen of the bladder catheter to expand a balloon structure located in the patient's bladder. In some examples, the bladder catheter is inserted through the urethra and into the bladder without using a guidewire and/or cystoscope. In other examples, the bladder catheter is inserted over the same guidewire used to position the ureteral catheters. Accordingly, when inserted in this manner, the ureteral catheters can be arranged to extend from the distal end of the bladder catheter and, optionally, proximal ends of the ureteral catheters can be arranged to terminate in a drainage lumen of the bladder catheter.

In some examples, the urine is permitted to drain by gravity from the urethra. In other examples, a negative pressure is induced in the ureteral catheter and/or bladder catheter to facilitate drainage of the urine.

Figure 18B:
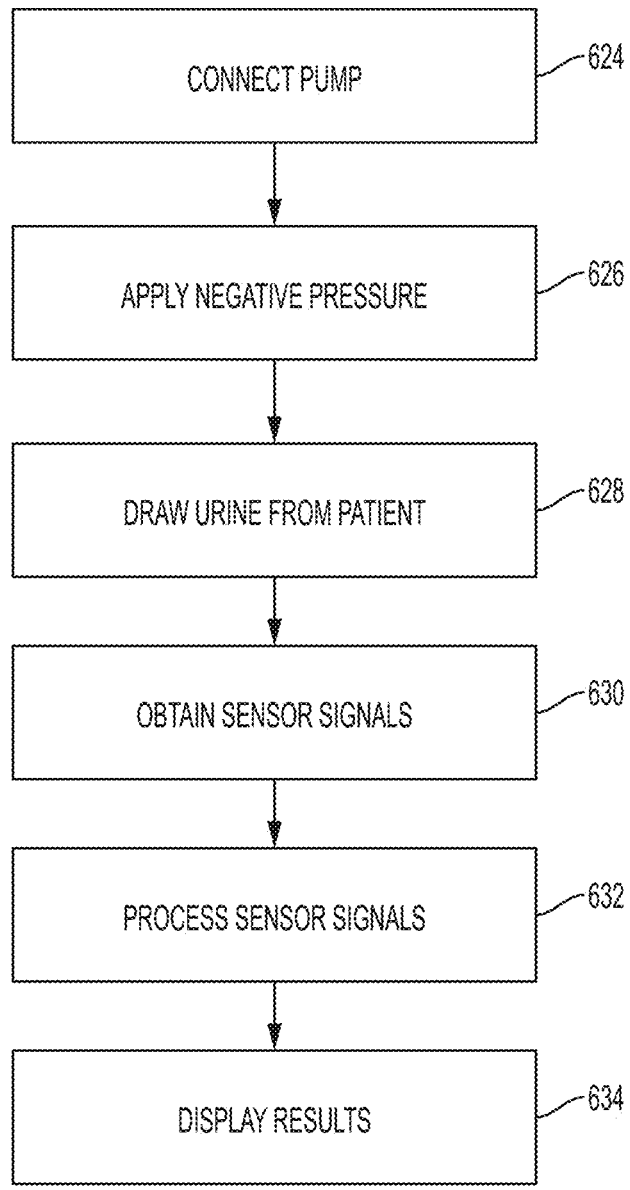
FIG. 18B is a flow chart illustrating a process for applying negative pressure using a ureteral catheter or urine collection assembly according to an example of the present invention.

With reference to FIG. 18B, steps for using the urine collection assembly for inducement of negative pressure in the ureter(s) and/or kidney(s) are illustrated. As shown at box 624, after the indwelling portions of the bladder and/or ureteral catheters are correctly positioned and anchoring/retention structures are deployed, the external proximal ends of the catheter(s) are connected to fluid collection or pump assemblies. For example, the ureteral catheter(s) can be connected to a pump for inducing negative pressure at the patient's renal pelvis and/or kidney. In a similar manner, the bladder catheter can be connected directly to a urine collection container for gravity drainage of urine from the bladder or connected to a pump for inducing negative pressure at the bladder.

Once the catheter(s) and pump assembly are connected, negative pressure is applied to the renal pelvis and/or kidney and/or bladder through the drainage lumens of the ureteral catheters and/or bladder catheter, as shown at box 626. The negative pressure is intended to counter congestion mediated interstitial hydrostatic pressures due to elevated intra-abdominal pressure and consequential or elevated renal venous pressure or renal lymphatic pressure. The applied negative pressure is therefore capable of increasing flow of filtrate through the medullary tubules and of decreasing water and sodium re-absorption.

In some examples, mechanical stimulation can be provided to portions of the ureters and/or renal pelvis to supplement or modify therapeutic affects obtained by application of negative pressure. For example, mechanical stimulation devices, such as linear actuators and other known devices for providing, for example, vibration waves, disposed in distal portions of the ureteral catheter(s) can be actuated. While not intending to be bound by theory, it is believed that such stimulation effects adjacent tissues by, for example, stimulating nerves and/or actuating peristaltic muscles associated with the ureter(s) and/or renal pelvis. Stimulation of nerves and activation of muscles may produce changes in pressure gradients or pressure levels in surrounding tissues and organs which may contribute to or, in some cases, enhance therapeutic benefits of negative pressure therapy. In some examples, the mechanical stimulation can comprise pulsating stimulation. In other examples, low levels of mechanical stimulation can be provided continuously as negative pressure is being provided through the ureteral catheter(s). In other examples, inflatable portions of the ureteral catheter could be inflated and deflated in a pulsating manner to stimulate adjacent nerve and muscle tissue, in a similar manner to actuation of the mechanical stimulation devices described herein.

As a result of the applied negative pressure, as shown at box 628, urine is drawn into the catheter at the plurality of drainage ports at the distal end thereof, through the drainage lumen of the catheter, and to a fluid collection container for disposal. As the urine is being drawn to the collection container, at box 630, sensors disposed in the fluid collection system provide a number of measurements about the urine that can be used to assess the volume of urine collected, as well as information about the physical condition of the patient and composition of the urine produced. In some examples, the information obtained by the sensors is processed, as shown at box 632, by a processor associated with the pump and/or with another patient monitoring device and, at box 634, is displayed to the user via a visual display of an associated feedback device.

Figure 19:
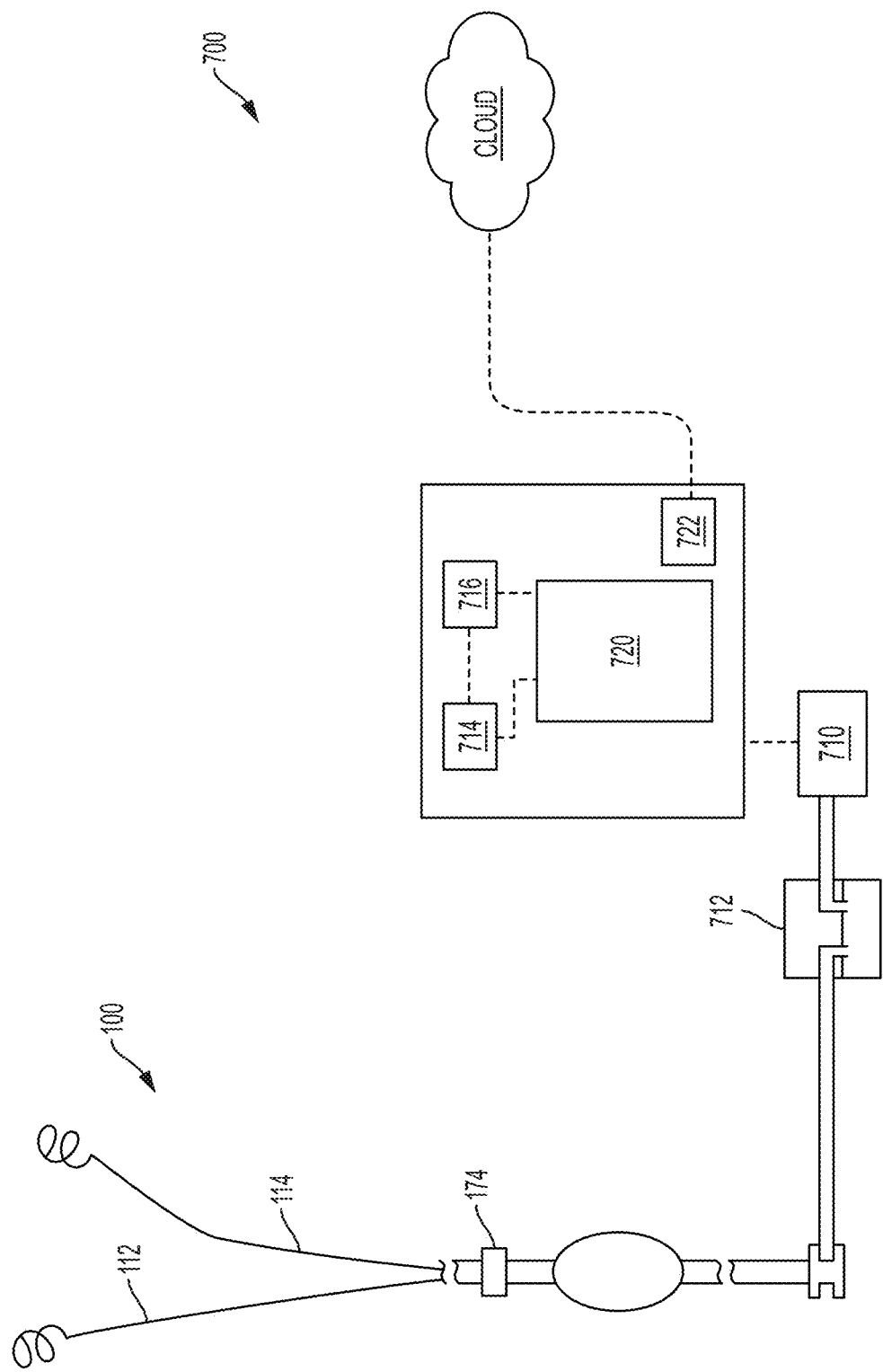
FIG. 19 is a schematic drawing of a system for inducing negative pressure to the urinary tract of a patient according to an example of the present invention.

Exemplary Fluid Collection System:

Having described an exemplary urine collection assembly and method of positioning such an assembly in the patient's body, with reference to FIG. 19, a system 700 for inducing negative pressure to a patient's ureter(s) and/or kidney(s) will now be described. The system 700 can comprise the ureteral catheter(s), bladder catheter or the urine collection assembly 100 described hereinabove. As shown in FIG. 19, ureteral catheters 112, 114 and/or the bladder catheter 116 of the assembly 100 are connected to one or more fluid collection containers 712 for collecting urine drawn from the renal pelvis and/or bladder. In some examples, the bladder catheter 116 and the ureteral catheters 112, 114 are connected to different fluid collection containers 712. The fluid collection container 712 connected to the ureteral catheter(s) 112, 114 can be in fluid communication with an external fluid pump 710 for generating negative pressure in the ureter(s) and kidney(s) through the ureteral catheter(s) 112, 114. As discussed herein, such negative pressure can be provided for overcoming interstitial pressure and forming urine in the kidney or nephron. In some examples, a connection between the fluid collection container 712 and pump 710 can comprise a fluid lock or fluid barrier to prevent air from entering the renal pelvis or kidney in case of incidental therapeutic or non-therapeutic pressure changes. For example, inflow and outflow ports of the fluid container can be positioned below a fluid level in the container. Accordingly, air is prevented from entering medical tubing or the catheter through either the inflow or outflow ports of the fluid container 712. As discussed previously, external portions of the tubing extending between the fluid collection container 712 and the pump 710 can include one or more filters to prevent urine and/or particulates from entering the pump 710.

As shown in FIG. 19, the system 700 further comprises a controller 714, such as a microprocessor, electronically coupled to the pump 710 and having or associated with computer readable memory 716. In some examples, the memory 716 comprises instructions that, when executed, cause the controller 714 to receive information from sensors 174 located on or associated with portions of the assembly 100. Information about a condition of the patient can be determined based on information from the sensors 174. Information from the sensors 174 can also be used to determine and implement operating parameters for the pump 710.

In some examples, the controller 714 is incorporated in a separate and remote electronic device in communication with the pump 710, such as a dedicated electronic device, computer, tablet PC, or smart phone. Alternatively, the controller 714 can be included in the pump 710 and, for example, can control both a user interface for manually operating the pump 710, as well as system functions such as receiving and processing information from the sensors 174.

The controller 714 is configured to receive information from the one or more sensors 174 and to store the information in the associated computer-readable memory 716. For example, the controller 714 can be configured to receive information from the sensor 174 at a predetermined rate, such as once every second, and to determine a conductance based on the received information. In some examples, the algorithm for calculating conductance can also include other sensor measurements, such as urine temperature, to obtain a more robust determination of conductance.

The controller 714 can also be configured to calculate patient physical statistics or diagnostic indicators that illustrate changes in the patient's condition over time. For example, the system 700 can be configured to identify an amount of total sodium excreted. The total sodium excreted may be based, for example, on a combination of flow rate and conductance over a period of time.

With continued reference to FIG. 19, the system 700 can further comprise a feedback device 720, such as a visual display or audio system, for providing information to the user. In some examples, the feedback device 720 can be integrally formed with the pump 710. Alternatively, the feedback device 720 can be a separate dedicated or a multipurpose electronic device, such as a computer, laptop computer, tablet PC, smart phone, or other handheld electronic devices. The feedback device 720 is configured to receive the calculated or determined measurements from the controller 714 and to present the received information to a user via the feedback device 720. For example, the feedback device 720 may be configured to display current negative pressure (in mmHg) being applied to the urinary tract. In other examples, the feedback device 720 is configured to display current flow rate of urine, temperature, current conductance in mS/m of urine, total urine produced during the session, total sodium excreted during the session, other physical parameters, or any combination thereof.

In some examples, the feedback device 720 further comprises a user interface module or component that allows the user to control operation of the pump 710. For example, the user can engage or turn off the pump 710 via the user interface. The user can also adjust pressure applied by the pump 710 to achieve a greater magnitude or rate of sodium excretion and fluid removal.

Optionally, the feedback device 720 and/or pump 710 further comprise a data transmitter 722 for sending information from the device 720 and/or pump 710 to other electronic devices or computer networks. The data transmitter 722 can utilize a short-range or long-range data communications protocol. An example of a short-range data transmission protocol is Bluetooth®. Long-range data transmission networks include, for example, Wi-Fi or cellular networks. The data transmitter 722 can send information to a patient's physician or caregiver to inform the physician or caregiver about the patient's current condition. Alternatively, or in addition, information can be sent from the data transmitter 722 to existing databases or information storage locations, such as, for example, to include the recorded information in a patient's electronic health record (EHR).

Figure 20A:
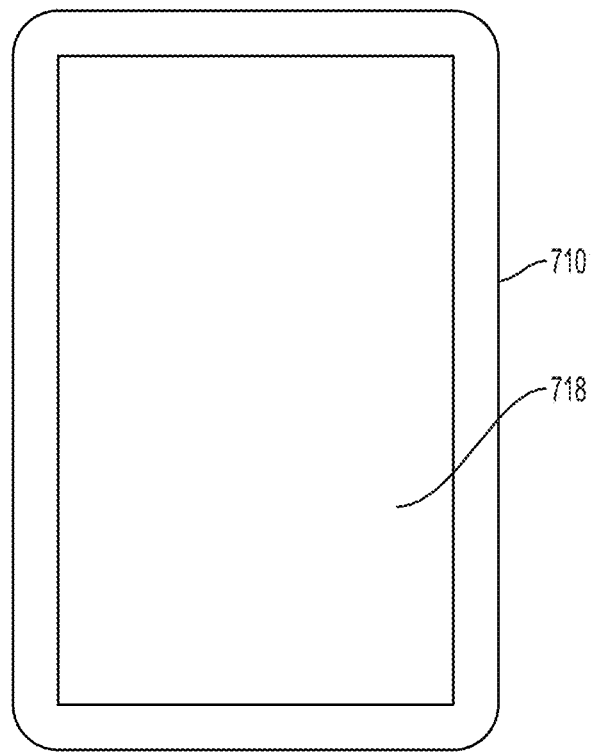
FIG. 20A is a plan view of a pump for use with the system of FIG. 19 according to an example of the present invention.
Figure 20B:
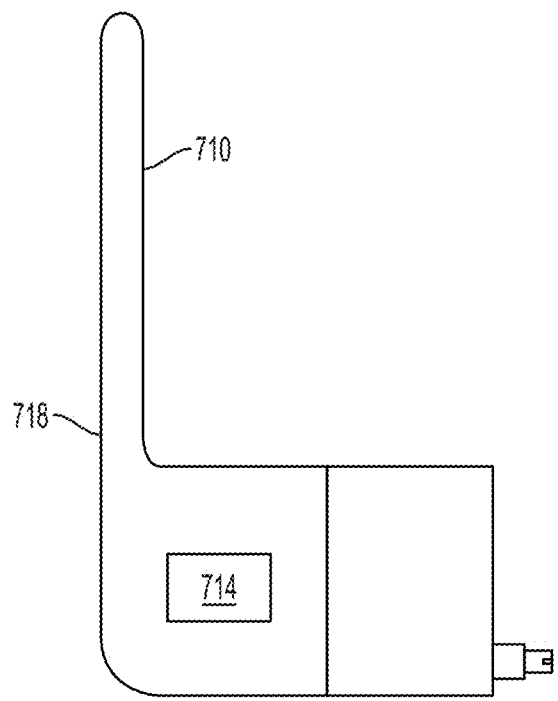
FIG. 20B is a side elevation view of the pump of FIG. 20A.

With reference to FIGS. 20A and 20B, an exemplary pump 710 for use with the system is illustrated. In some examples, the pump 710 is a micro-pump configured to draw fluid from the catheter(s) 112, 114 (shown, for example, in FIG. 1) and having a sensitivity or accuracy of about 10 mmHg or less. Desirably, the pump 710 is capable of providing a range of flow of urine between 0.05 ml/min and 3 ml/min for extended periods of time, for example, for about 8 hours to about 24 hours per day, for one (1) to about 30 days or longer. At 0.2 ml/min, it is anticipated that about 300 mL of urine per day is collected by the system 700. The pump 710 can be configured to provide a negative pressure to the bladder of the patient, the negative pressure ranging between about 0.1 mmHg and 50 mmHg or about 5 mmHg to about 20 mmHg (gauge pressure at the pump 710). For example, a micro-pump manufactured by Langer Inc. (Model BT100-2J) can be used with the presently disclosed system 700. Diaphragm aspirator pumps, as well as other types of commercially available pumps, can also be used for this purpose. Peristaltic pumps can also be used with the system 700. In other examples, a piston pump, vacuum bottle, or manual vacuum source can be used for providing negative pressure. In other examples, the system can be connected to a wall suction source, as is available in a hospital, through a vacuum regulator for reducing negative pressure to therapeutically appropriate levels.

In some examples, the pump 710 is configured for extended use and, thus, is capable of maintaining precise suction for extended periods of time, for example, for about 8 hours to about 24 hours per day, for 1 to about 30 days or longer. Further, in some examples, the pump 710 is configured to be manually operated and, in that case, includes a control panel 718 that allows a user to set a desired suction value. The pump 710 can also include a controller or processor, which can be the same controller that operates the system 700 or can be a separate processor dedicated for operation of the pump 710. In either case, the processor is configured for both receiving instructions for manual operation of the pump and for automatically operating the pump 710 according to predetermined operating parameters. Alternatively, or in addition, operation of the pump 710 can be controlled by the processor based on feedback received from the plurality of sensors associated with the catheter.

In some examples, the processor is configured to cause the pump 710 to operate intermittently. For example, the pump 710 may be configured to emit pulses of negative pressure followed by periods in which no negative pressure is provided. In other examples, the pump 710 can be configured to alternate between providing negative pressure and positive pressure to produce an alternating flush and pump effect. For example, a positive pressure of about 0.1 mmHg to 20 mmHg, and preferably about 5 mmHg to 20 mmHg can be provided followed by a negative pressure ranging from about 0.1 mmHg to 50 mmHg.

EXPERIMENTAL EXAMPLES

Inducement of negative pressure within the renal pelvis of farm swine was performed for the purpose of evaluating effects of negative pressure therapy on renal congestion in the kidney. An objective of these studies was to demonstrate whether a negative pressure delivered into the renal pelvis significantly increases urine output in a swine model of renal congestion. In Example 1, a pediatric Fogarty catheter, normally used in embolectomy or bronchoscopy applications, was used in the swine model solely for proof of principle for inducement of negative pressure in the renal pelvis. It is not suggested that a Fogarty catheter be used in humans in clinical settings to avoid injury of urinary tract tissues. In Example 2, the ureteral catheter 112 shown in FIGS. 2A and 2B, and including a helical retention portion for mounting or maintaining a distal portion of the catheter in the renal pelvis or kidney, was used.

Example 1

Method

Figure 21:
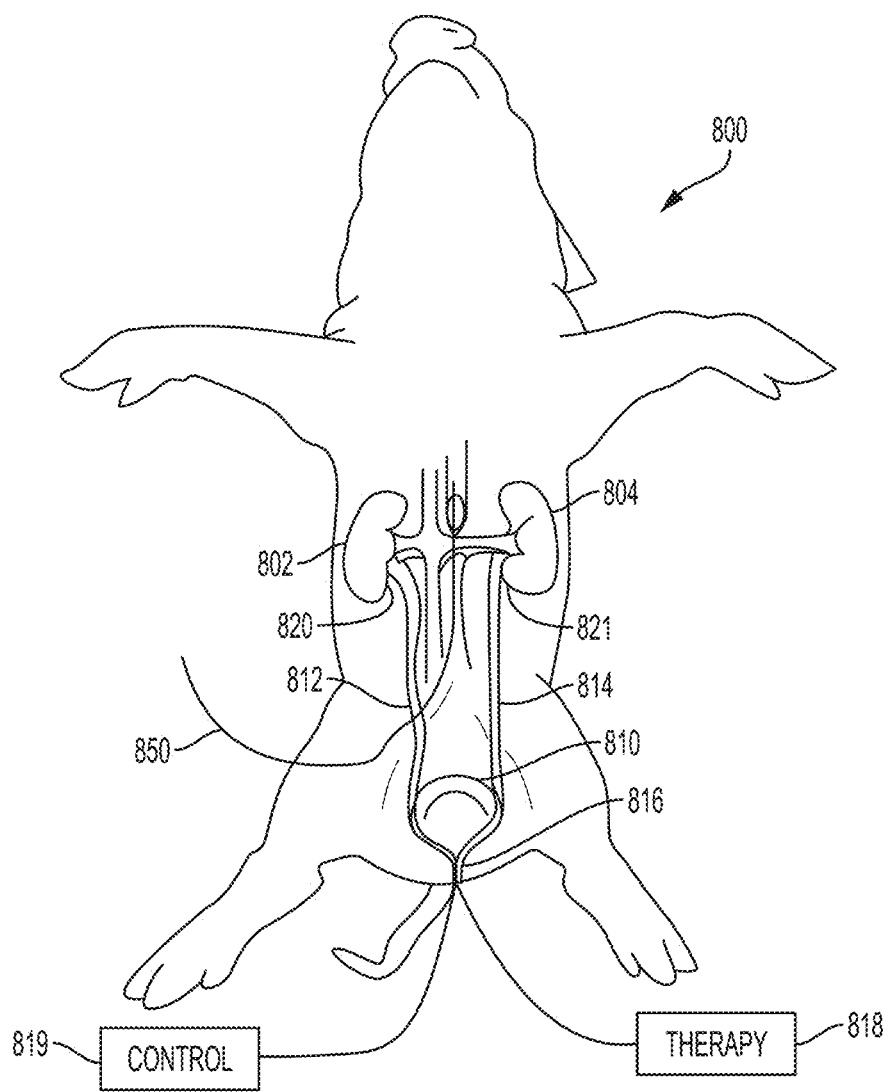
FIG. 21 is a schematic drawing of an experimental set-up for evaluating negative pressure therapy in a swine model.

Four farm swine 800 were used for purposes of evaluating effects of negative pressure therapy on renal congestion in the kidney. As shown in FIG. 21, pediatric Fogarty catheters 812, 814 were inserted to the renal pelvis region 820, 821 of each kidney 802, 804 of the four swine 800. The catheters 812, 814 were deployed within the renal pelvis region by inflating an expandable balloon to a size sufficient to seal the renal pelvis and to maintain the position of the balloon within the renal pelvis. The catheters 812, 814 extend from the renal pelvis 802, 804, through a bladder 810 and urethra 816, and to fluid collection containers external to the swine.

Urine output of two animals was collected for a 15 minute period to establish a baseline for urine output volume and rate. Urine output of the right kidney 802 and the left kidney 804 were measured individually and found to vary considerably. Creatinine clearance values were also determined.

Renal congestion (e.g., congestion or reduced blood flow in the veins of the kidney) was induced in the right kidney 802 and the left kidney 804 of the animal 800 by partially occluding the inferior vena cava (IVC) with an inflatable balloon catheter 850 just above to the renal vein outflow. Pressure sensors were used to measure IVC pressure. Normal IVC pressures were 1-4 mmHg. By inflating the balloon of the catheter 850 to approximately three quarters of the IVC diameter, the IVC pressures were elevated to between 15-25 mmHg. Inflation of the balloon to approximately three quarters of IVC diameter resulted in a 50-85% reduction in urine output. Full occlusion generated IVC pressures above 28 mmHg and was associated with at least a 95% reduction in urine output.

One kidney of each animal 800 was not treated and served as a control ("the control kidney 802"). The ureteral catheter 812 extending from the control kidney was connected to a fluid collection container 819 for determining fluid levels. One kidney ("the treated kidney 804") of each animal was treated with negative pressure from a negative pressure source (e.g., a therapy pump 818 in combination with a regulator designed to more accurately control the low magnitude of negative pressures) connected to the ureteral catheter 814. The pump 818 was an Air Cadet Vacuum Pump from Cole-Parmer Instrument Company (Model No. EW-07530-85). The pump 818 was connected in series to the regulator. The regulator was an V-800 Series Miniature Precision Vacuum Regulator—⅛ NPT Ports (Model No. V-800-10-W/K), manufactured by Airtrol Components Inc.

The pump 818 was actuated to induce negative pressure within the renal pelvis 820, 821 of the treated kidney according to the following protocol. First, the effect of negative pressure was investigated in the normal state (e.g., without inflating the IVC balloon). Four different pressure levels (−2, −10, −15, and −20 mmHg) were applied for 15 minutes each and the rate of urine produced and creatinine clearance were determined. Pressure levels were controlled and determined at the regulator. Following the −20 mmHg therapy, the IVC balloon was inflated to increase the pressure by 15-20 mmHg. The same four negative pressure levels were applied. Urine output rate and creatinine clearance rate for the congested control kidney 802 and treated kidney 804 were obtained. The animals 800 were subject to congestion by partial occlusion of the IVC for 90 minutes. Treatment was provided for 60 minutes of the 90 minute congestion period.

Following collection of urine output and creatinine clearance data, kidneys from one animal were subjected to gross examination then fixed in a 10% neutral buffered formalin. Following gross examination, histological sections were obtained, examined, and magnified images of the sections were captured. The sections were examined using an upright Olympus BX41 light microscope and images were captured using an Olympus DP25 digital camera. Specifically, photomicrograph images of the sampled tissues were obtained at low magnification (20× original magnification) and high magnification (100× original magnification). The obtained images were subjected to histological evaluation. The purpose of the evaluation was to examine the tissue histologically and to qualitatively characterize congestion and tubular degeneration for the obtained samples.

Surface mapping analysis was also performed on obtained slides of the kidney tissue. Specifically, the samples were stained and analyzed to evaluate differences in size of tubules for treated and untreated kidneys. Image processing techniques calculated a number and/or relative percentage of pixels with different coloration in the stained images. Calculated measurement data was used to determine volumes of different anatomical structures.

Results

Urine Output and Creatinine Clearance

Urine output rates were highly variable. Three sources of variation in urine output rate were observed during the study.

The inter-individual and hemodynamic variability were anticipated sources of variability known in the art. A third source of variation in urine output, upon information and belief believed to be previously unknown, was identified in the experiments discussed herein, namely, contralateral intra-individual variability in urine output.

Baseline urine output rates were 0.79 ml/min for one kidney and 1.07 ml/min for the other kidney (e.g., a 26% difference). The urine output rate is a mean rate calculated from urine output rates for each animal.

When congestion was provided by inflating the IVC balloon, the treated kidney urine output dropped from 0.79 ml/min to 0.12 ml/min (15.2% of baseline). In comparison, the control kidney urine output rate during congestion dropped from 1.07 ml/min to 0.09 ml/min (8.4% of baseline). Based on urine output rates, a relative increase in treated kidney urine output compared to control kidney urine output was calculated, according to the following equation:

(Therapy Treated/Baseline Treated)/(Therapy Control/Baseline Control)=Relative increase (0.12 ml/min/0.79 ml/min)/(0.09 ml/min/1.07 ml/min)=180.6%

Thus, the relative increase in treated kidney urine output rate was 180.6% compared to control. This result shows a greater magnitude of decrease in urine production caused by congestion on the control side when compared to the treatment side. Presenting results as a relative percentage difference in urine output adjusts for differences in urine output between kidneys.

Figure 22:
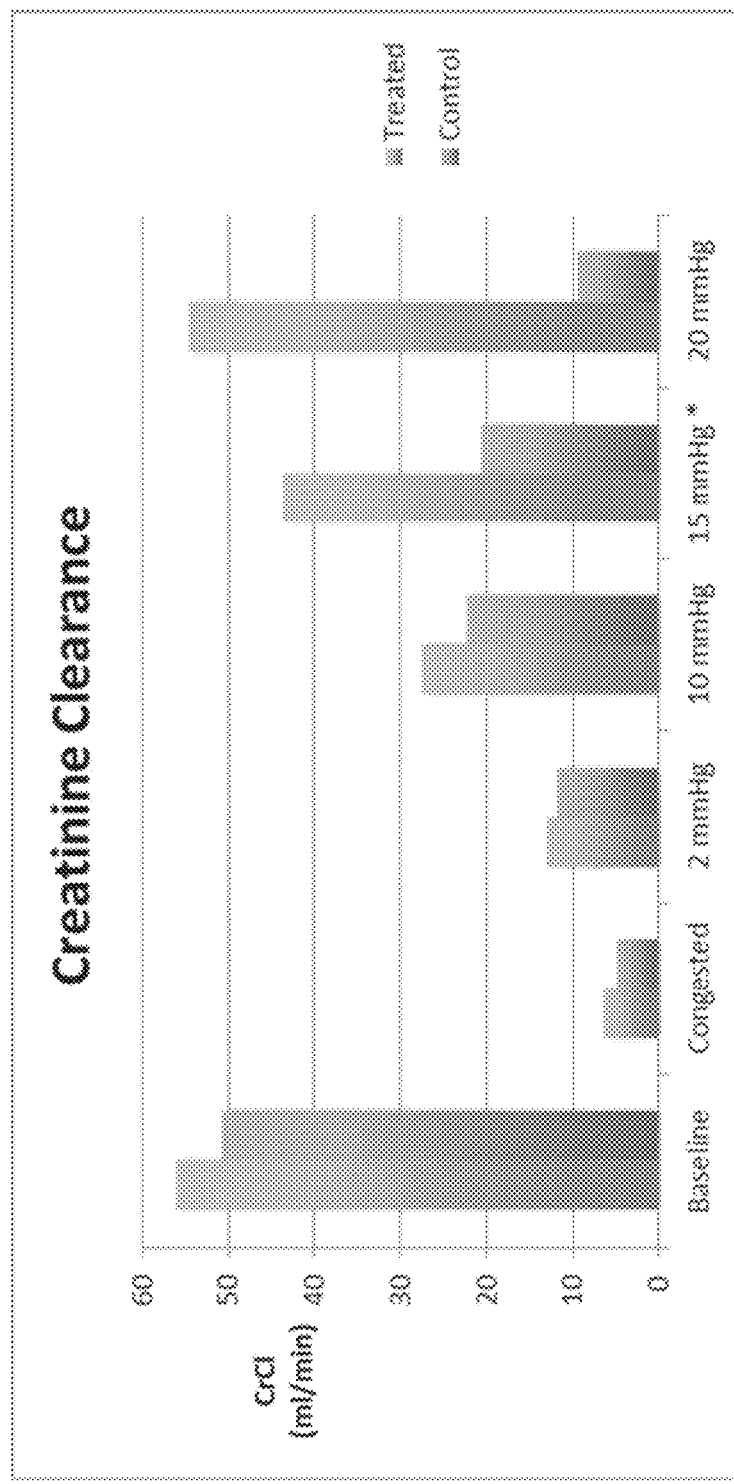
FIG. 22 is a graph of creatinine clearance rates for tests conducted using the experimental set-up shown in FIG. 21.

Creatinine clearance measurements for baseline, congested, and treated portions for one of the animals are shown in FIG. 22.

Gross Examination and Histological Evaluation

Based on gross examination of the control kidney (right kidney) and treated kidney (left kidney), it was determined that the control kidney had a uniformly dark red-brown color, which corresponds with more congestion in the control kidney compared to the treated kidney. Qualitative evaluation of the magnified section images also noted increased congestion in the control kidney compared to the treated kidney. Specifically, as shown in Table 1, the treated kidney exhibited lower levels of congestion and tubular degeneration compared to the control kidney. The following qualitative scale was used for evaluation of the obtained slides.

Congestion

| Lesion | Score |
| --- | --- |
| None: | 0 |
| Mild: | 1 |
| Moderate: | 2 |
| Marked: | 3 |
| Severe: | 4 |

Tubular Degeneration

| Lesion | Score |
| --- | --- |
| None: | 0 |
| Mild: | 1 |
| Moderate: | 2 |
| Marked: | 3 |
| Severe: | 4 |

TABLE 1

TABULATED RESULTS

| Animal ID/Organ/Gross lesion | Slide number | Histologic lesions | | |
| --- | --- | --- | --- | --- |
| | | Congestion | Tubular hyaline casts | Granulomas |
| 6343/Left Kidney/Normal | R16-513-1 | 1 | 1 | 0 |
| 6343/Left Kidney/Normal with hemorrhagic streak | R16-513-2 | 1 | 1 | 0 |
| 6343/Right Kidney/Congestion | R16-513-3 | 2 | 2 | 1 |
| 6343/Right Kidney/Congestion | R16-513-4 | 2 | 1 | 1 |

As shown in Table 1, the treated kidney (left kidney) exhibited only mild congestion and tubular degeneration. In contrast, the control kidney (right kidney) exhibited moderate congestion and tubular degeneration. These results were obtained by analysis of the slides discussed below.

Figure 23A:
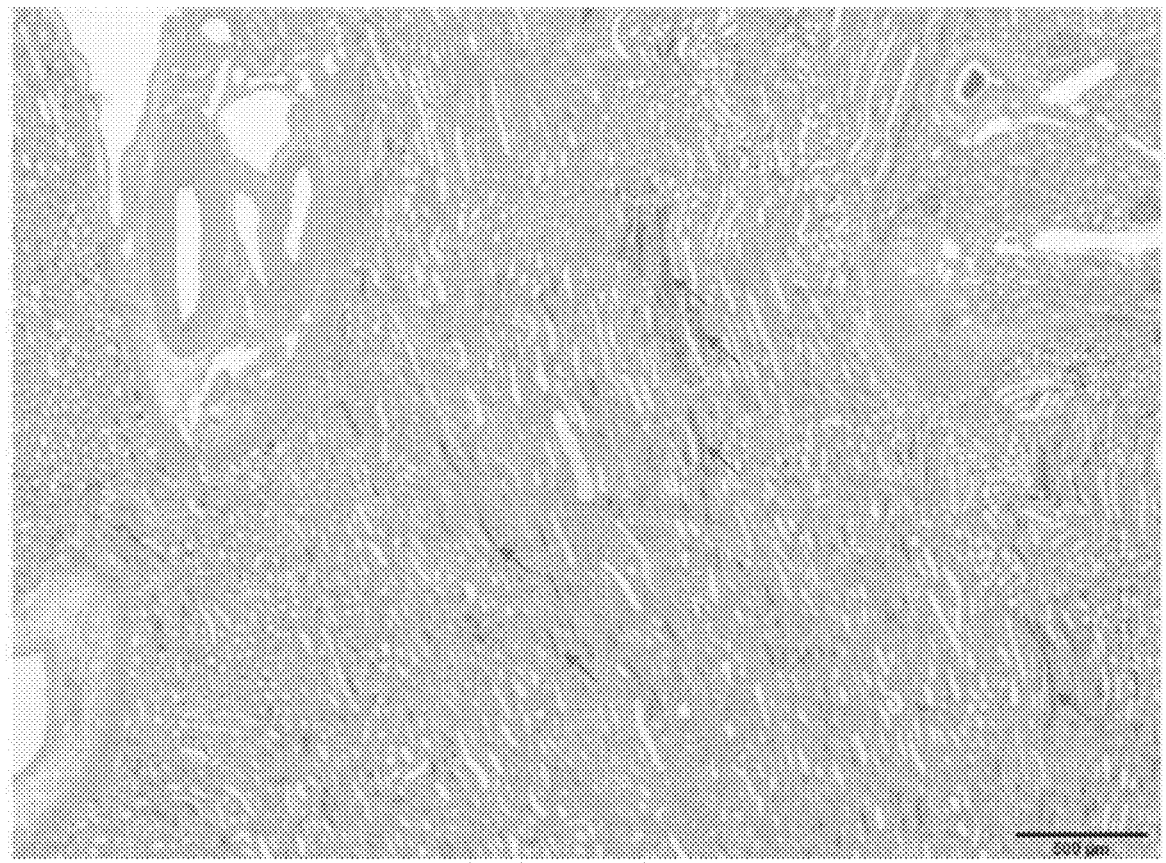
FIG. 23A is a low magnification photomicrograph of kidney tissue from a congested kidney treated with negative pressure therapy.
Figure 23B:
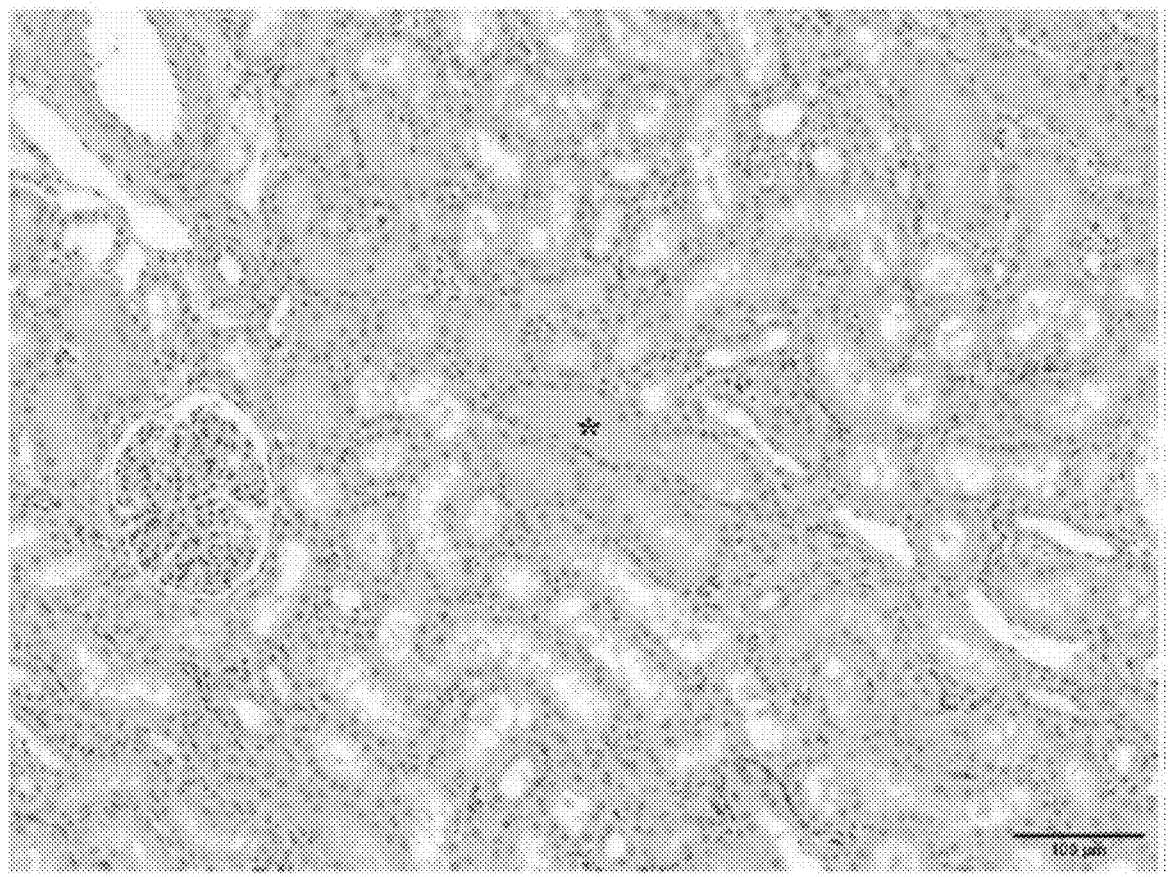
FIG. 23B is a high magnification photomicrograph of the kidney tissue shown in FIG. 23A.

FIGS. 23A and 23B are low and high magnification photomicrographs of the left kidney (treated with negative pressure) of the animal. Based on the histological review, mild congestion in the blood vessels at the corticomedullary junction was identified, as indicated by the arrows. As shown in FIG. 23B, a single tubule with a hyaline cast (as identified by the asterisk) was identified.

Figure 23C:
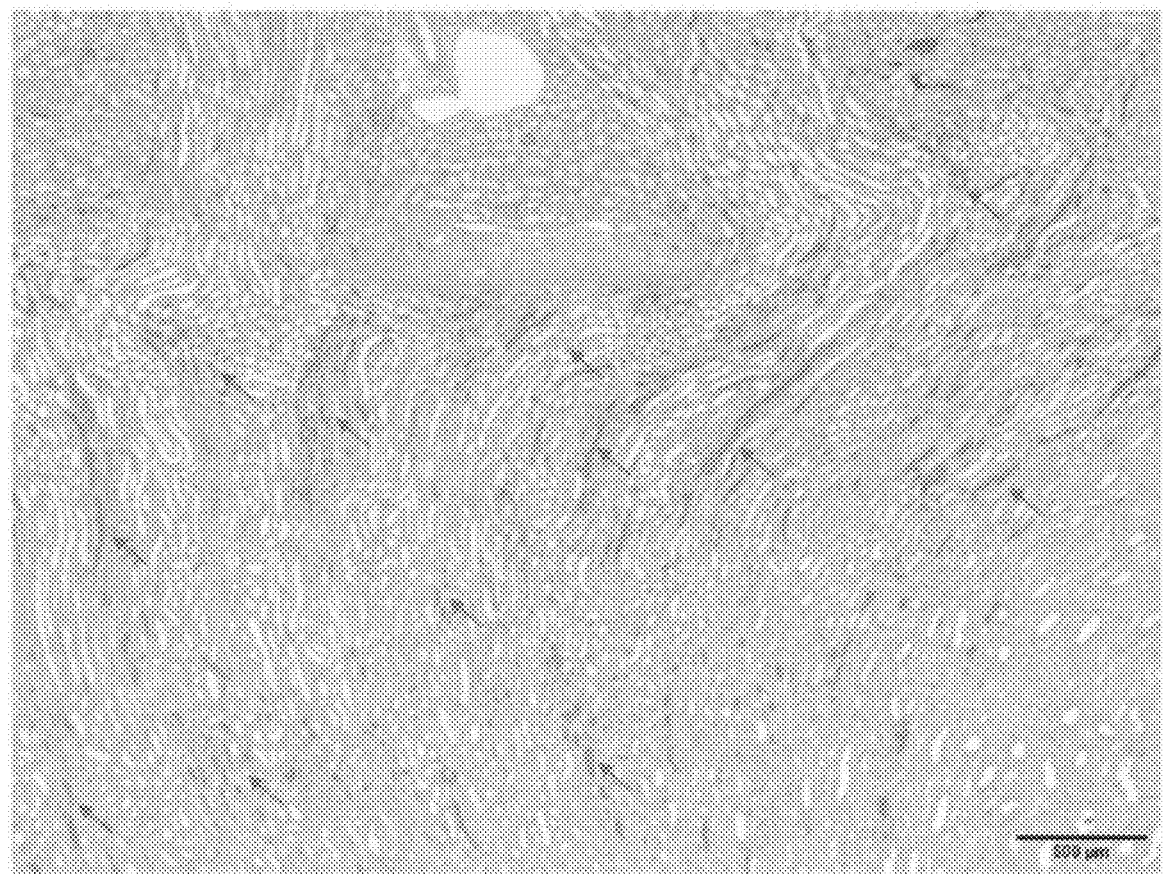
FIG. 23C is a low magnification photomicrograph of kidney tissue from a congested and untreated (e.g., control) kidney.
Figure 23D:
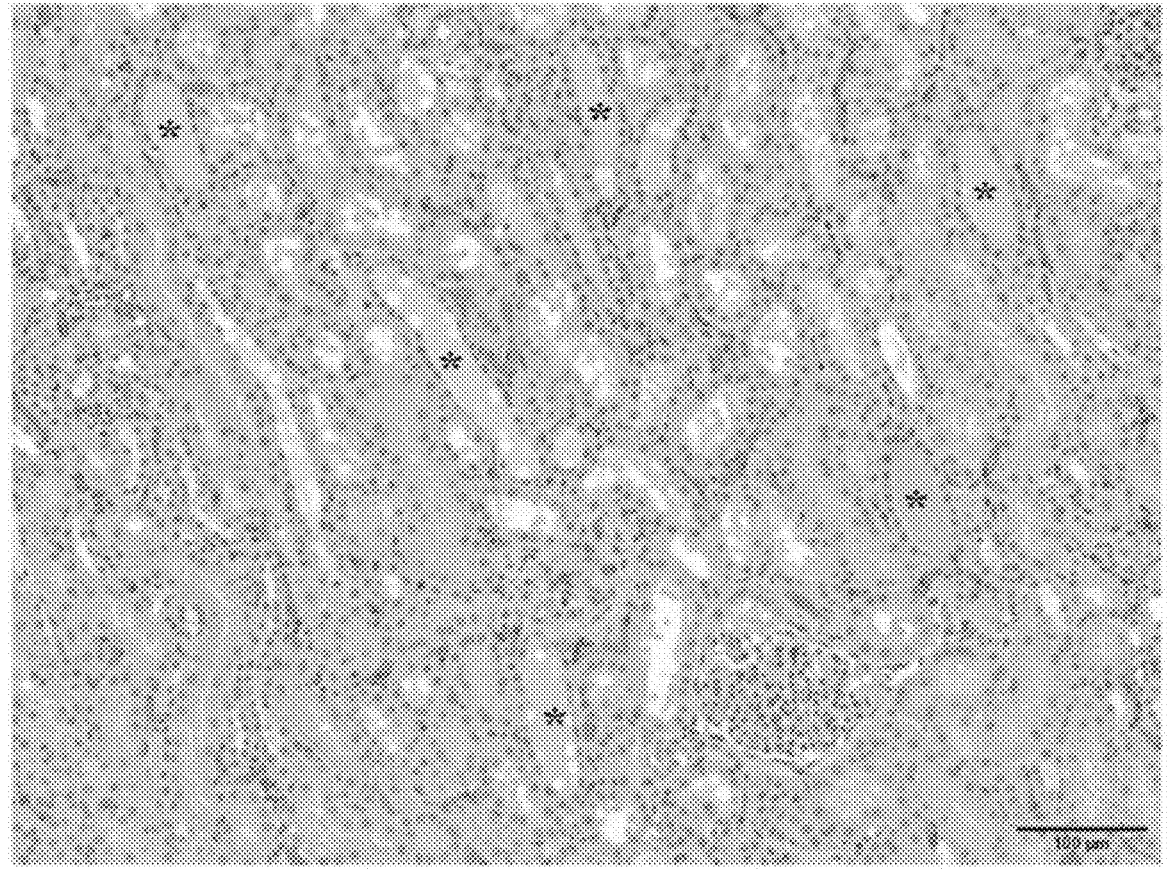
FIG. 23D is a high magnification photomicrograph of the kidney tissue shown in FIG. 23C.

FIGS. 23C and 23D are low and high resolution photomicrographs of the control kidney (right kidney). Based on the histological review, moderate congestion in the blood vessel at the corticomedullary junction was identified, as shown by the arrows in FIG. 23C. As shown in FIG. 23D, several tubules with hyaline casts were present in the tissue sample (as identified by asterisks in the image). Presence of a substantial number of hyaline casts is evidence of hypoxia.

Surface mapping analysis provided the following results. The treated kidney was determined to have 1.5 times greater fluid volume in Bowman's space and 2 times greater fluid volume in tubule lumen. Increased fluid volume in Bowman's space and the tubule lumen corresponds to increased urine output. In addition, the treated kidney was determined to have 5 times less blood volume in capillaries compared to the control kidney. The increased volume in the treated kidney appears to be a result of (1) a decrease in individual capillary size compared to the control and (2) an increase in the number of capillaries without visible red blood cells in the treated kidney compared to the control kidney, an indicator of less congestion in the treated organ.

Summary

These results indicate that the control kidney had more congestion and more tubules with intraluminal hyaline casts, which represent protein-rich intraluminal material, compared to the treated kidney. Accordingly, the treated kidney exhibits a lower degree of loss of renal function. While not intending to be bound by theory, it is believed that as severe congestion develops in the kidney, hypoxemia of the organ follows. Hypoxemia interferes with oxidative phosphorylation within the organ (e.g., ATP production). Loss of ATP and/or a decrease in ATP production inhibits the active transport of proteins causing intraluminal protein content to increase, which manifests as hyaline casts. The number of renal tubules with intraluminal hyaline casts correlates with the degree of loss of renal function. Accordingly, the reduced number of tubules in the treated left kidney is believed to be physiologically significant. While not intending to be bound by theory, it is believed that these results show that damage to the kidney can be prevented or inhibited by applying negative pressure to a catheter inserted into the renal pelvis to facilitate urine output.

Example 2

Method

Four (4) farm swine (A, B, C, D) were sedated and anesthetized. Vitals for each of the swine were monitored throughout the experiment and cardiac output was measured at the end of each 30-minute phase of the study. Ureteral catheters, such as the ureteral catheter 112 shown in FIGS. 2A and 2B, were deployed in the renal pelvis region of the kidneys of each of the swine. The deployed catheters were a 6 Fr catheter having an outer diameter of 2.0±0.1 mm. The catheters were 54±2 cm in length, not including the distal retention portion. The retention portion was 16±2 mm in length. As shown in the catheter 112 in FIGS. 2A and 2B, the retention portion included two full coils and one proximal half coil. The outer diameter of the full coils, shown by line D1 in FIGS. 2A and 2B, was 18±2 mm. The half coil diameter D2 was about 14 mm. The retention portion of the deployed ureteral catheters included six drainage holes, plus an additional hole at the distal end of the catheter tube. The diameter of each of the drainage holes was 0.83±0.01 mm. The distance between adjacent drainage holes 132, specifically the linear distance between drainage holes when the coils were straightened, was 22.5±2.5 mm.

The ureteral catheters were positioned to extend from the renal pelvis of the swine, through the bladder, and urethra, and to fluid collection containers external to each swine. Following placement of the ureteral catheters, pressure sensors for measuring IVC pressure were placed in the IVC at a position distal to the renal veins. An inflatable balloon catheter, specifically a PTS® percutaneous balloon catheter (30 mm diameter by 5 cm length), manufactured by NuMED Inc. of Hopkinton, NY, was expanded in the IVC at a position proximal to the renal veins. A thermodilution catheter, specifically a Swan-Ganz thermodilution pulmonary artery catheter manufactured by Edwards Lifesciences Corp. of Irvine, CA, was then placed in the pulmonary artery for the purpose of measuring cardiac output.

Initially, baseline urine output was measured for 30 minutes, and blood and urine samples were collected for biochemical analysis. Following the 30-minute baseline period, the balloon catheter was inflated to increase IVC pressure from a baseline pressure of 1-4 mmHg to an elevated congested pressure of about 20 mmHg (+/−5 mmHg). A congestion baseline was then collected for 30 minutes with corresponding blood and urine analysis.

At the end of the congestion period, the elevated congested IVC pressure was maintained and negative pressure diuresis treatment was provided for swine A and swine C. Specifically, the swine (A, C) were treated by applying a negative pressure of −25 mmHg through the ureteral catheters with a pump. As in previously-discussed examples, the pump was an Air Cadet Vacuum Pump from Cole-Parmer Instrument Company (Model No. EW-07530-85). The pump was connected in series to a regulator. The regulator was a V-800 Series Miniature Precision Vacuum Regulator—⅛ NPT Ports (Model No. V-800-10-W/K), manufactured by Airtrol Components Inc. The swine were observed for 120 minutes, as treatment was provided. Blood and urine collection were performed every 30 minutes, during the treatment period. Two of the swine (B, D) were treated as congested controls (e.g., negative pressure was not applied to the renal pelvis through the ureteral catheters), meaning that the two swine (B, D) did not receive negative pressure diuresis therapy.

Following collection of urine output and creatinine clearance data for the 120-minute treatment period, the animals were sacrificed and kidneys from each animal were subjected to gross examination. Following gross examination, histological sections were obtained and examined, and magnified images of the sections were captured.

Results

Measurements collected during the Baseline, Congestion, and Treatment periods are provided in Table 2. Specifically, urine output, serum creatinine, and urinary creatinine measurements were obtained for each time period. These values allow for the calculation of a measured creatinine clearance as follows:

$$\text{Creatinine Clearance: } CrCl = \text{Urine Output (ml/min)} * \frac{\text{Urinary Creatinine (mg/dl)}}{\text{Serum Creatinine (mg/dl)}}$$

In addition, Neutrophil gelatinase-associated lipocalin (NGAL) values were measured from serum samples obtained for each time period and Kidney Injury Molecule 1 (KIM-1) values were measured from the urine samples obtained for each time period. Qualitative histological findings determined from review of the obtained histological sections are also included in Table 2.

TABLE 2

| Animal<br>Treatment assignment | A<br>Treatment | B<br>Control | C<br>Treatment | D<br>Control |
|---|---|---|---|---|
| Baseline: | | | | |
| Urine output (ml/min) | 3.01 | 2.63 | 0.47 | 0.98 |
| Serum creatinine (mg/dl) | 0.8 | 0.9 | 3.2 | 1.0 |
| Creatinine clearance (ml/min) | 261 | 172 | 5.4 | 46.8 |

TABLE 2-continued

| Animal<br>Treatment assignment | A<br>Treatment | B<br>Control | C<br>Treatment | D<br>Control |
|---|---|---|---|---|
| Serum NGAL (ng/ml) | 169 | * | 963 | 99 |
| Urinary KIM-1 (ng/ml) | 4.11 | * | 3.59 | 1.16 |
| Congestion: | | | | |
| Urine output (ml/min) | 0.06 (2%) | 0.53 (20%) | 0.12 (25%) | 0.24 (25%) |
| Serum creatinine (mg/dl) | 1.2 (150%) | 1.1 (122%) | 3.1 (97%) | 1.2 (120%) |
| Creatinine clearance (ml/min) | 1.0 (0.4%) | 30.8 (18%) | 1.6 (21%) | 16.2 (35%) |
| Serum NGAL (ng/ml) | 102 (60%) | * | 809 (84%) | 126 (127%) |
| Urinary KIM-1 (ng/ml) | 24.3 (591%) | * | 2.2 (61%) | 1.39 (120%) |
| Treatment: | | | | |
| Urine output (ml/min) | 0.54 (17%) | ** | 0.47 (101%) | 0.35 (36%) |
| Serum creatinine (mg/dl) | 1.3 (163%) | | 3.1 (97%) | 1.7 (170%) |
| Creatinine clearance (ml/min) | 30.6 (12%) | | 18.3 (341%) | 13.6 (29%) |
| Serum NGAL (ng/ml) | 197 (117%) | | 1104 (115%) | 208 (209%) |
| Urinary KIM-1 (ng/ml) | 260 (6326%) | | 28.7 (799%) | 233 (20000%) |
| Histological findings: | | | | |
| Blood volume in capillary space | 2.4% | ** | 0.9% | 4.0% |
| Hyaline casts | Mild/Mod | | None | Mod |
| Degranulation | Mild/Mod | | None | Mod |

Data are raw values (% baseline)
* not measured
** confounded by phenylephrine

Animal A:

The animal weighed 50.6 kg and had a baseline urine output rate of 3.01 ml/min, a baseline serum creatinine of 0.8 mg/dl, and a measured CrCl of 261 ml/min. It is noted that these measurements, aside from serum creatinine, were uncharacteristically high relative to other animals studied. Congestion was associated with a 98% reduction in urine output rate (0.06 ml/min) and a >99% reduction in CrCl (1.0 ml/min). Treatment with negative pressure applied through the ureteral catheters was associated with urine output and CrCl of 17% and 12%, respectively, of baseline values, and 9× and >10×, respectively, of congestion values. Levels of NGAL changed throughout the experiment, ranging from 68% of baseline during congestion to 258% of baseline after 90 minutes of therapy. The final value was 130% of baseline. Levels of KIM-1 were 6 times and 4 times of baseline for the first two 30-minute windows after baseline assessment, before increasing to 68×, 52×, and 63× of baseline values, respectively, for the last three collection periods. The 2-hour serum creatinine was 1.3 mg/dl. Histological examination revealed an overall congestion level, measured by blood volume in capillary space, of 2.4%. Histological examination also noted several tubules with intraluminal hyaline casts and some degree of tubular epithelial degeneration, a finding consistent with cellular damage.

Animal B:

The animal weighed 50.2 kg and had a baseline urine output rate of 2.62 ml/min and a measured CrCl of 172 ml/min (also higher than anticipated). Congestion was associated with an 80% reduction in urine output rate (0.5 ml/min) and an 83% reduction in CrCl (30 ml/min). At 50 minutes into the congestion (20 minutes after the congestion baseline period), the animal experienced an abrupt drop in mean arterial pressure and respiration rate, followed by tachycardia. The anesthesiologist administered a dose of phenylephrine (75 mg) to avert cardiogenic shock. Phenylephrine is indicated for intravenous administration when blood pressure drops below safe levels during anesthesia. However, since the experiment was testing the impact of congestion on renal physiology, administration of phenylephrine confounded the remainder of the experiment.

Animal C:

The animal weighed 39.8 kg and had a baseline urine output rate of 0.47 ml/min, a baseline serum creatinine of 3.2 mg/dl, and a measured CrCl of 5.4 ml/min. Congestion was associated with a 75% reduction in urine output (0.12 ml/min) and a 79% reduction in CrCl (1.6 ml/min). It was determined that baseline NGAL levels were >5× the upper limit of normal (ULN). Treatment with negative pressure applied to the renal pelvis through the ureteral catheters was associated with a normalization of urine output (101% of baseline) and a 341% improvement in CrCl (18.2 ml/min). Levels of NGAL changed throughout the experiment, ranging from 84% of baseline during congestion to 47% to 84% of baseline between 30 and 90 minutes. The final value was 115% of baseline. Levels of KIM-1 decreased 40% from baseline within the first 30 minutes of congestion, before increasing to 8.7×, 6.7×, 6.6×, and 8× of baseline values, respectively, for the remaining 30-minute windows. Serum creatinine level at 2 hours was 3.1 mg/dl. Histological examination revealed an overall congestion level, measured by blood volume in capillary space, of 0.9%. The tubules were noted to be histologically normal.

Animal D:

The animal weighed 38.2 kg and had a baseline urine output of 0.98 ml/min, a baseline serum creatinine of 1.0 mg/dl, and a measured CrCl of 46.8 ml/min. Congestion was associated with a 75% reduction in urine output rate (0.24 ml/min) and a 65% reduction in Cr Cl (16.2 ml/min). Continued congestion was associated with a 66% to 91% reduction of urine output and 89% to 71% reduction in CrCl. Levels of NGAL changed throughout the experiment, ranging from 127% of baseline during congestion to a final value of 209% of baseline. Levels of KIM-1 remained between 1× and 2× of baseline for the first two 30-minute windows after baseline assessment, before increasing to 190×, 219×, and 201× of baseline values for the last three 30-minute periods. The 2-hour serum creatinine level was 1.7 mg/dl. Histological examination revealed an overall congestion level 2.44× greater than that observed in tissue samples for the treated animals (A, C) with an average capillary size 2.33 times greater than that observed in either of the treated animals.

The histological evaluation also noted several tubules with intraluminal hyaline casts as well as tubular epithelial degeneration, indicating substantial cellular damage.

Summary

While not intending to be bound by theory, it is believed that the collected data supports the hypothesis that venous congestion creates a physiologically significant impact on renal function. In particular, it was observed that elevation of the renal vein pressure reduced urine output by 75% to 98% within seconds. The association between elevations in biomarkers of tubular injury and histological damage is consistent with the degree of venous congestion generated, both in terms of magnitude and duration of the injury.

The data also appears to support the hypothesis that venous congestion decreases the filtration gradients in the medullary nephrons by altering the interstitial pressures. The change appears to directly contribute to the hypoxia and cellular injury within medullary nephrons. While this model does not mimic the clinical condition of AKI, it does provide insight into the mechanical sustaining injury.

The data also appears to support the hypothesis that applying negative pressure to the renal pelvis through ureteral catheters can increase urine output in a venous congestion model. In particular, negative pressure treatment was associated with increases in urine output and creatinine clearance that would be clinically significant. Physiologically meaningful decreases in medullary capillary volume and smaller elevations in biomarkers of tubular injury were also observed. Thus, it appears that by increasing urine output rate and decreasing interstitial pressures in medullary nephrons, negative pressure therapy may directly decrease congestion. While not intending to be bound by theory, by decreasing congestion, it may be concluded that negative pressure therapy reduces hypoxia and its downstream effects within the kidney in a venous congestion mediated AKI.

The experimental results appear to support the hypothesis that the degree of congestion, both in terms of the magnitude of pressure and duration, is associated with the degree of cellular injury observed. Specifically, an association between the degree of urine output reduction and the histological damage was observed. For example, treated Swine A, which had a 98% reduction in urine output, experienced more damage than treated Swine C, which had a 75% reduction in urine output. As would be expected, control Swine D, which was subjected to a 75% reduction in urine output without benefit of therapy for two and a half hours, exhibited the most histological damage. These findings are broadly consistent with human data demonstrating an increased risk for AKI onset with greater venous congestion. See e.g., Legrand, M. et al., *Association between systemic hemodynamics and septic acute kidney injury in critically ill patients: a retrospective observational study. Critical Care* 17:R278-86, 2013.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. A negative pressure therapy system for increasing urine production, the negative pressure therapy system comprising:
   (a) a pump assembly, the pump assembly comprising:
      (i) a pump configured to provide negative pressure to a kidney, and
      (ii) a controller configured to regulate the negative pressure provided by the pump within a pressure range of about 5 mm Hg to about 25 mm Hg to increase urine output from the kidney.

2. The negative pressure therapy system of claim 1, wherein the controller regulates the negative pressure provided by the pump based upon changes in physiological condition.

3. The negative pressure therapy system of claim 2, further comprising one or more sensors that detect change(s) in the physiological condition, wherein the controller regulates the negative pressure provided by the pump based upon information measured by the one or more sensors.

4. The negative pressure therapy system of claim 1, wherein the controller is integrated into the pump.

5. The negative pressure therapy system of claim 1, wherein the controller is located outside of a body.

6. The negative pressure therapy system of claim 1, wherein the pump is located outside of a body.

7. The negative pressure therapy system of claim 1, further comprising a catheter having (i) a proximal portion comprising a drainage lumen and (ii) a distal portion comprising a retention portion configured to be positioned in a urinary tract, the retention portion comprising one or more drainage ports that permit fluid flow into the drainage lumen.

8. The negative pressure therapy system of claim 7, wherein the proximal portion of the catheter is configured to be connected to the pump to provide negative pressure through the catheter to the kidney.

9. The negative pressure therapy system of claim 8, wherein the retention portion is configured such that, when the pump provides negative pressure through the catheter, fluid is drawn into the one or more drainage ports while mucosal tissue is prevented from appreciably occluding the one or more drainage ports.

10. The negative pressure therapy system of claim 9, wherein the one or more drainage ports are located on a radially inwardly facing side of the retention portion and, when the pump provides negative pressure through the catheter, a radially outwardly facing side of the retention portion inhibits mucosal tissue from contacting the one or more drainage ports.

11. The negative pressure therapy system of claim 10, wherein the radially outwardly facing side of the retention portion is essentially free of drainage ports.

12. A negative pressure therapy system for increasing urine production, the negative pressure therapy system comprising:
   (a) a pump assembly, the pump assembly comprising:
      (i) a pump configured to provide negative pressure to a kidney, and
      (ii) a controller configured to regulate the negative pressure of about 5 mm Hg to about 25 mm Hg provided by the pump, based upon changes in physiological condition, so as to increase urine output from the kidney.

13. The negative pressure therapy system of claim 12, further comprising one or more sensors that detect change(s) in the physiological condition, wherein the controller regulates the negative pressure provided by the pump based upon information measured by the one or more sensors.

14. The negative pressure therapy system of claim 13, wherein the controller is integrated into the pump.

15. The negative pressure therapy system of claim 13, wherein the controller is located outside of a body.

16. The negative pressure therapy system of claim 13, wherein the pump is located outside of a body.

17. The negative pressure therapy system of claim 13, further comprising a catheter having (i) a proximal portion comprising a drainage lumen and (ii) a distal portion comprising a retention portion configured to be positioned in a urinary tract, the retention portion comprising one or more drainage ports that permit fluid flow into the drainage lumen.

18. The negative pressure therapy system of claim 17, wherein the proximal portion of the catheter is configured to be connected to the pump to provide negative pressure through the catheter to the kidney.

19. The negative pressure therapy system of claim 18, wherein the retention portion is configured such that, when the pump provides negative pressure through the catheter, fluid is drawn into the one or more drainage ports while mucosal tissue is prevented from appreciably occluding the one or more drainage ports.

20. The negative pressure therapy system of claim 19, wherein the one or more drainage ports are located on a radially inwardly facing side of the retention portion and, when the pump provides negative pressure through the catheter, a radially outwardly facing side of the retention portion inhibits mucosal tissue from contacting the one or more drainage ports.

21. The negative pressure therapy system of claim 20, wherein the radially outwardly facing side of the retention portion is essentially free of drainage ports.

* * * * *